(12) United States Patent
Ahrens et al.

(10) Patent No.: US 8,114,991 B2
(45) Date of Patent: Feb. 14, 2012

(54) AMINO-1,3,5-TRIAZINES N-SUBSTITUTED WITH CHIRAL BICYCLIC RADICALS, PROCESS FOR THEIR PREPARATION, COMPOSITIONS THEREOF, AND THEIR USE AS HERBICIDES AND PLANT GROWTH REGULATORS

(75) Inventors: Hartmut Ahrens, Frankfurt (DE); Hansjörg Dietrich, Hofheim (DE); Klemens Minn, Hattersheim (DE); Thomas Auler, Bad Soden (DE); Hermann Bieringer, Eppstein (DE); Martin Hills, Idstein (DE); Heinz Kehne, Hofheim (DE); Hubert Menne, Hofheim (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 10/771,649

(22) Filed: Feb. 3, 2004

(65) Prior Publication Data
US 2004/0157739 A1 Aug. 12, 2004

(30) Foreign Application Priority Data

Feb. 5, 2003 (EP) .................................... 03002438
Aug. 1, 2003 (EP) .................................... 03016680

(51) Int. Cl.
C07D 251/48 (2006.01)
A01N 43/68 (2006.01)
(52) U.S. Cl. ....................................... 544/208; 504/232
(58) Field of Classification Search .................. 544/208; 504/232; 514/232
See application file for complete search history.

(56) References Cited

U.S. PATENT DOCUMENTS

| 4,948,395 A | 8/1990 | Armstrong |
| 6,069,114 A * | 5/2000 | Lorenz et al. .................. 504/232 |

FOREIGN PATENT DOCUMENTS

| EP | 0 864 567 A1 | 9/1998 |
| WO | WO 96/21640 | 7/1996 |
| WO | WO 97/29095 | 8/1997 |
| WO | WO 97/31904 | 9/1997 |
| WO | WO 98/47877 | 10/1998 |
| WO | WO 03/099266 A2 | 12/2003 |

OTHER PUBLICATIONS

Balkenhohl et al., "Optisch active Amine durch Lipase-katalysierte Methoxyacetylierung", J. Prakt., Chem., vol. 339, pp. 381-384, 1997.
Houben Weyl, "Methods of Organic Chemistry", vol. 21 B, pp. 1833-1847, 1995.
Houben Weyl, "Methods of Organic Chemistry", vol. 21e, pp. 5133-5157, 1995.
Choi et al., "Lipase/Palladium-Catalyzed Asymmetric Transformations of Ketoximes to Optically Active Amines", Organic Letters, vol. 3, No. 25, pp. 4099-4101, 2001.
Hyun et al., "Liquid chromatographic resolution of racemic amines, amino alcohols and related compounds on a chiral crown ether stationary phase", Journal of Chromatography A, vol. 959, No. 1-2, pp. 75-83, 2002.
Database Accession No. Beilstein Registry No. 7854896.
Database Accession No. Beilstein Registry No. 7855080.
Database Accession No. Beilstein Registry No. 7855360.
Database Accession No. Beilstein Registry No. 8202654.
Database Accession No. Beilstein Registry No. 6582921.
Database Accession No. Beilstein Registry No. 7122876.
Database Accession No. Beilstein Registry No. 8111842.
Database Accession No. Beilstein Registry No. 9264314.
Database Accession No. Beilstein Registry No. 8201255.
Database Accession No. 109:189967.
Zhang et al., "Highly Enantioselective Hydrogenation of Cyclic Enamides Catalydes by a Rh-PennPhos Catalyst", 3. Org. Chem., vol. 64, pp. 1774-1775, 1999.
Lawson, "Specificity in the Alkylation of Serine at the Active Site of α-Chymotrypsin by Aromatic α-Bromo Amides", Rinehemistry, vol. 19, pp. 7140-2144, 1980.
Perrone et al, J.Med. Chem., vol. 42, 1999, pp. 490-496, XP002282274.
Database Beilstein, Beilstein Institute for Organic Chemistry, XP 002283375, Accession No. BRN 5267406, Kitaguchi et al, J. Amer. Chem. Soc., vol. 111, No. 8, 1989, pp. 3094-3095.

* cited by examiner

*Primary Examiner* — Venkataraman Balasubramanian
(74) *Attorney, Agent, or Firm* — Frommer Lawrence & Haug

(57) ABSTRACT

Amino-1,3,5-triazines N-substituted with chiral bicyclic radicals, process for their preparation, compositions thereof, and their use as herbicides and plant growth regulators.
The invention relates to an optically active compound of formula (I) or a salt thereof:

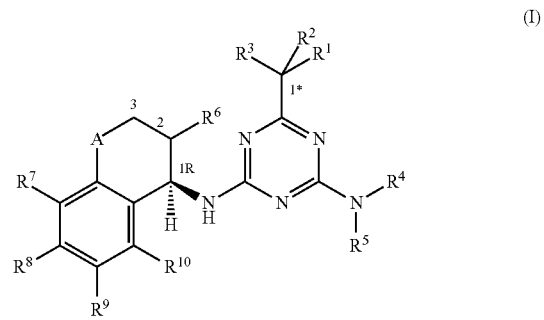

wherein the various symbols are as defined in the description, to processes for their preparation, to compositions thereof, and to their use as herbicides or plant growth regulators. The invention also relates to novel intermediates of formula (III), (V) and (XIII) as defined in the description.

13 Claims, No Drawings

AMINO-1,3,5-TRIAZINES N-SUBSTITUTED WITH CHIRAL BICYCLIC RADICALS, PROCESS FOR THEIR PREPARATION, COMPOSITIONS THEREOF, AND THEIR USE AS HERBICIDES AND PLANT GROWTH REGULATORS

Amino-1,3,5-triazines N-substituted with chiral bicyclic radicals, process for their preparation, compositions thereof, and their use as herbicides and plant growth regulators.

The invention relates to optically active isomers of some 2-amino-4-(bicyclyl)amino-6-(substituted alkyl)-1,3,5-triazine derivatives, processes for their preparation, to compositions and intermediates thereof, and to their use as herbicides or plant growth regulators for the control of undesired plants or vegetation.

BACKGROUND OF THE INVENTION

WO 97/31904 and EP-A-0864567 describe the preparation of 2-amino-4-bicyclyl-amino-1,3,5-triazines and their use as herbicides and plant growth regulators. The reference generically describes various amino-1,3,5-triazine derivatives which are substituted with some radicals comprising one or more centres of chirality in principle. The specifically disclosed derivatives, however, were described as mixtures of stereoisomers only, such as racemic mixtures of enantiomers or mixtures of diastereomers in their racemic forms. In some cases, the known active substances have disadvantages when used, for example have an insufficient herbicidal action against harmful plants, too rigid applicational limitations related to weather, climate and/or soil conditions, too narrow a spectrum against weeds or too little crop selectivity.

It has now been found that surprisingly specific optically active isomers of certain substituted 2-amino-1,3,5-triazine derivatives possess advantageous applicational properties compared with the prior art compounds or corresponding racemic compounds or other optical isomers thereof.

For instance they are very active herbicides which can be used for the control of a range of harmful weeds, having surprisingly more potent herbicidal efficacy than stereoisomers thereof or racemic mixtures thereof.

DETAILED DESCRIPTION OF THE INVENTION

The present invention relates to a compound which is an optically active compound of formula (I):

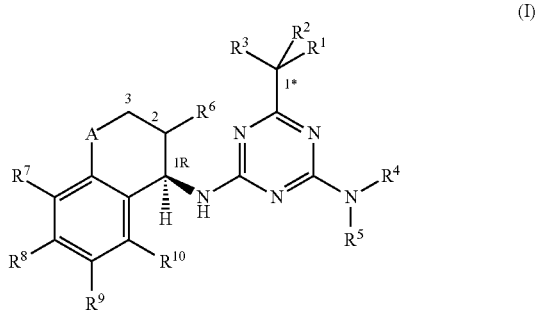

in which:
$R^1$ is H, halogen, $(C_1-C_6)$alkyl, $(C_1-C_6)$haloalkyl, $[(C_1-C_4)$alkoxy]$(C_1-C_6)$alkyl, $(C_3-C_6)$cycloalkyl which is unsubstituted or substituted by one or more radicals selected from the group consisting of halogen, $(C_1-C_4)$alkyl and $(C_1-C_4)$haloalkyl, or is $(C_2-C_6)$alkenyl, $(C_2-C_6)$alkynyl, $(C_2-C_6)$haloalkenyl, $(C_4-C_6)$cycloalkenyl, $(C_4-C_6)$halocycloalkenyl, $(C_1-C_6)$alkoxy or $(C_1-C_6)$haloalkoxy;
$R^2$ is H, halogen, $(C_1-C_6)$alkyl or $(C_1-C_4)$alkoxy; or
$R^1$ and $R^2$ can together with the attached carbon atom form a $(C_3-C_6)$cycloalkyl or $(C_4-C_6)$cycloalkenyl ring;
$R^3$ is H, $(C_1-C_6)$alkyl, $(C_1-C_4)$alkoxy or halogen;
$R^4$ and $R^5$ are each independently H, $(C_1-C_4)$alkyl, $(C_1-C_4)$haloalkyl, $(C_3-C_4)$alkenyl, $(C_3-C_4)$haloalkenyl, $(C_3-C_4)$alkynyl, $(C_3-C_4)$haloalkynyl or an acyl radical;
$R^5$ is H, $(C_1-C_6)$alkyl or $(C_1-C_6)$alkoxy;
$R^7$, $R^8$, $R^9$ and $R^{10}$ are each independently H, $(C_1-C_4)$alkyl, $(C_1-C_3)$haloalkyl, halogen, $(C_1-C_3)$alkoxy, $(C_1-C_3)$haloalkoxy or CN;
A is $CH_2$, O or a direct bond;
and the stereochemical configuration at the marked 1 position is (R) having a stereochemical purity of from 60 to 100% (R), preferably 70-100% (R), in particular 80-100% (R), based on the content of stereoisomers having (R)- and (S)-configurations at this position;
or an agriculturally acceptable salt thereof.

For reference purposes in formula (I) certain ring carbon atoms are marked from 1 to 3, whilst the carbon atom bonded to the triazine ring is marked 1*.

In the present invention the stereochemical configuration at the marked 1 position is fixed as being predominantly (R) according to the Cahn-Ingold-Prelog system, however is the subject matter of the invention is also directed to all stereoisomers at other locants which are encompassed by formula (I), and their mixtures. Such compounds of the formula (I) contain, e.g. one or more additional asymmetric carbon atoms or else double bonds which are not stated specifically in the formula (I). It will be understood that the present invention embraces both the pure isomers and more or less enriched mixtures thereof, where the asymmetric carbon atom in marked 1 position is in the R-configuration or, in mixtures, a compound or compounds of same chemical constitution have the R-configuration in marked 1 position or are present in a ratio that compounds having the R-configuration are predominantly present (at least 60% R-configuration) whilst the other asymmetric carbon atom(s) may be present in racemic form or are more or less resolved too. Provided the condition for the stereochemical configuration at marked 1 position is met, the possible stereoisomers which are defined by their specific spatial form, such as enantiomers, diastereomers, Z- and E-isomers, are all encompassed by formula (I) and can be obtained by customary methods from mixtures of the stereoisomers, or else be prepared by stereoselective reactions in combination with the use of stereochemically pure starting materials.

Dependent on the definition of the radicals $R^1$, $R^2$ and $R^3$ one possible additional centre of asymmetry referred to above is the carbon atom marked 1* in formula (I), in which case the compound of formula (I) according to the invention can exist as at least two pure stereoisomeric forms, i.e. (1R,1*R) and (1R,1*S) selected from the four pure stereoisomers which exist in principle. A further centre of asymmetry may also be present at the carbon atom marked 2 in formula (I), in which case the compound of the invention can exist as at least four pure stereoisomeric forms, each of these additional asymmetric carbon atoms having (R) or (S) configuration according to the Cahn-Ingold-Prelog system, i.e. pure isomers having the configuration (1R,1*R,2R), (1R,1*R,2S), (1R,1*S,2R) and (1R,1*S,2S), selected from the eight pure stereoisomers which exist in principle. Moreover depending on the nature of the groups $R^1$, $R^2$, $R^3$, $R^4$, $R^5$, $R^6$, $R^7$, $R^8$, $R^9$ and $R^{10}$, further asymmetric carbon atoms may be present.

Where in the formulae shown hereinafter, a specific stereochemical configuration is defined at any position, for example at the carbon atom marked 1, 2 or 1*, unless otherwise defined, it means that the stereochemical purity at the marked position is 60 to 100%, preferably 70-100%, in particular 80-100%, most preferably 100%. "Stereochemical purity" means the amount of the stated stereoisomer expressed as a percentage of the total amount of stereoisomers having the given chiral centre.

The invention also encompasses any keto and enol tautomer forms and mixtures and salts thereof, if respective functional groups are present.

The compounds of the formula (I) can form salts by addition of a suitable inorganic or organic acid such as, for example, HCl, HBr, $H_2SO_4$ or $HNO_3$, or a mono- or bifunctional carboxylic acid or sulfonic acid, to a basic group such as, for example, amino or alkylamino.

Some compounds of the formula (I) can form salts by addition of a suitable inorganic or organic base. Such compounds (I) have a functional group which contain an "acidic hydrogen atom", such as the carboxyl or the sulfonyl group, which may be a substituent in the definition of the acyl group. Examples of these salts are metal salts, particularly alkaline metal salts or alkaline earth metal salts, preferably, sodium- or potassium salts, or unsubstituted or substituted ammonium salts, such as ammonium salts or salts of organic amines, or quaternary ammonium salts.

In the present patent specification, including the accompanying claims, the aforementioned substituents have the following meanings:

Halogen means fluorine, chlorine, bromine or iodine.

The term "halo" before the name of a radical means that this radical is partially or completely halogenated, that is to say, substituted by F, Cl, Br, or 1, in any combination. The expression "$(C_1-C_6)$alkyl" means an unbranched or branched non-cyclic saturated hydrocarbon radical having 1, 2, 3, 4, 5 or 6 carbon atoms (indicated by a range of C-atoms in the parenthesis), such as, for example a methyl, ethyl, propyl, isopropyl, 1-butyl, 2-butyl, 2-methylpropyl or tert-butyl radical. The same applies to alkyl groups in composite radicals such as "alkoxyalkyl".

Alkyl radicals and also in composite groups, unless otherwise defined, preferably have 1 to 4 carbon atoms.

"$(C_1-C_6)$Haloalkyl" means an alkyl group mentioned under the expression "$(C_1-C_6)$alkyl" in which one or more hydrogen atoms are replaced by the same number of identical or different halogen atoms, such as monohaloalkyl, e.g. $CH_2F$, $CH_2Cl$, $CH_2Br$, $CH_2I$, $CH_2CH_2F$, $CH_2CH_2Cl$, $CH_2CH_2Br$, $CH_2CH_2I$, $CHFCH_3$, or perhaloalkyl, such as $CF_3$, $CCl_3$, $CF_2CF_3$, $CCl_2CCl_3$, $CF_2CCl_3$ and $CCl_2CClF_2$, or $CHF_2$, $CF_3CH_2$, $CHF_2CF_2$, $CH_2FCHCl$ or $CHCl_2$. "$(C_1-C_4)$ Haloalkyl" is preferred, particularly monohaloalkyl, perhaloalkyl, $CF_3$, $CHF_2$, $CH_2F$, $CHFCH_3$, $CF_2CF_3$, $CH_2FCHCl$, $CH_2Cl$, $CCl_3$, $CHCl_2$ or $CH_2CH_2Cl$;

"$[(C_1-C_4)Alkoxy](C_1-C_6)alkyl$" means $(C_1-C_6)$alkyl which is substituted by $(C_1-C_4)$alkoxy. "$(C_1-C_6)$Alkoxy" means an alkoxy group whose carbon chain has the meaning given under the expression "$(C_1-C_6)$alkyl". "Haloalkoxy" is, for example, $OCF_3$, $OCHF_2$, $OCH_2F$, $CF_3CF_2O$, $OCH_2CF_3$ or $OCH_2CH_2Cl$.

"$(C_2-C_6)$Alkenyl" means an unbranched or branched non-cyclic carbon chain having a number of carbon atoms which corresponds to this stated range and which contains at least one double bond which can be located in any position of the respective unsaturated radical. "$(C_2-C_6)$Alkenyl" accordingly denotes, for example, the vinyl, allyl, 2-methyl-2-propenyl, 2-butenyl, pentenyl, 2-methylpentenyl or the hexenyl group.

"$(C_2-C_6)$Alkynyl" means an unbranched or branched non-cyclic carbon chain having a number of carbon atoms which corresponds to this stated range and which contains one triple bond which can be located in any position of the respective unsaturated radical.

"$(C_2-C_6)$Alkynyl" accordingly denotes, for example, the propargyl, 1-methyl-2-propynyl, 2-butynyl or 3-butynyl group.

"$(C_3-C_6)$Cycloalkyl" denotes monocyclic alkyl radicals, such as the cyclopropyl, cyclobutyl, cyclopentyl or cyclohexyl radical.

"$(C_4-C_6)$Cycloalkenyl" denotes a carbocyclic, nonaromatic, partially unsaturated ring having 4 to 6 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl.

An acyl radical is, in a broad sense, the radical of an organic acid which is formed formally by removing an OH group, for example the radical of a carboxylic acid and radicals of acids derived therefrom, such as thiocarboxylic acid, unsubstituted or N-substituted iminocarboxylic acids or the radical of carbonic monoesters, unsubstituted or N-substituted carbamic acid, unsubstituted or N-substituted thiocarbamic acid, sulfonic acids, sulfinic acids, phosphonic acids, and phosphinic acids. Acyl is, for example, formyl, alkylcarbonyl such as [$(C_1-C_4)$alkyl]carbonyl, phenylcarbonyl, alkyloxycarbonyl, phenyloxycarbonyl, benzyloxycarbonyl, alkylsulfonyl, alkylsulfinyl, phenylsulfonyl, N-alkyl-1-iminoalkyl and other radicals of organic acids. In this context, the radicals can be even further substituted in each of the alkyl or phenyl moieties, for example in the alkyl moiety by one or more radicals selected from the group consisting of halogen, alkoxy, phenyl and phenoxy; examples of substituents in the phenyl moiety are mono- or polysubstituted, preferably up to trisubstituted, identical or different radicals selected from the group consisting of halogen, $(C_1-C_4)$alkyl, $(C_1-C_4)$alkoxy, $(C_1-C_4)$haloalkyl, $(C_1-C_4)$haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

The acyl radical usually has 1 to 24 carbon atoms, preferably 1 to 18, more preferably 1 to 12, most preferably 1 to 7, in particular 1 to 4.

Acyl in the narrower sense is, for example, the radical of an alkanoic acid, alkenoic acid, alkynoic acid or arylcarboxylic acid (for example benzoyl), or is for example alkoxycarbonyl, alkenyloxycarbonyl, alkynyloxycarbonyl, aryloxycarbonyl, alkylsulfonyl, alkylsulfinyl or phenylsulfonyl; in an even narrower sense, acyl is a radical of an alkanoic acid, for example a $(C_1-C_{24})$alkanoic acid, preferably $(C_1-C_{18})$alkanoic acid, in particular $(C_1-C_{12})$alkanoic acid, very especially $(C_1-C_6)$alkanoic acid such as formyl, acetyl or propionyl.

The expression "one or more radicals selected from the group consisting of" in the definition is to be understood as meaning in each case one or more identical or different radicals selected from the stated group of radicals, unless specific limitations are defined expressly.

By combination of variables the generic formulae may formally define unstable functional groups, e.g. the carbamyl radical or the hydroxy carbonyloxy radical, which are unstable in neutral or acidic aqueous medium and which thus are not preferred or are used by way of their stable salts or degradation products only, respectively.

Compounds of the stated formula (I) according to the invention or their salts in which individual radicals have one of the preferred meanings which have already been stated or are stated hereinbelow and particularly those shown in the Table examples, or in particular those in which two or more of the preferred meanings which have already been stated or which are stated hereinbelow are combined, are of particular interest, mainly because of the more potent herbicidal action, better selectivity and/or greater ease of preparation.

Of particular interest are compounds of formula (I) where a radical selected from the group of radicals $R^1$, $R^2$, $R^3$, $R^4$, $R^5$, $R^6$, $R^7$, $R^8$, $R^9$, $R^{10}$ and A is preferably defined as set forth below, wherein the definition of the radical is independent from the definitions of the other radicals of said group. Preferred compounds of formula (I) contain a combination of radicals of said group which comprise two or more preferred meanings set forth below.

In the following preferred definitions it is generally to be understood that where symbols are not specifically defined they are to be as previously defined in the description.

Preferably $R^1$ is H, halogen, $(C_1-C_4)$alkyl, $(C_1-C_4)$haloalkyl, $[(C_1-C_4)$alkoxy$](C_1-C_4)$alkyl, $(C_3-C_6)$cycloalkyl which is unsubstituted or substituted by one or more, preferably one or two $(C_1-C_4)$alkyl groups, or is $(C_3-C_4)$halocycloalkyl, $(C_2-C_4)$alkenyl, $(C_2-C_4)$alkynyl, $(C_2-C_4)$haloalkenyl, $(C_1-C_4)$alkoxy or $(C_1-C_4)$haloalkoxy; more preferably $R^1$ is H, halogen, $(C_1-C_4)$alkyl, $(C_3-C_6)$cycloalkyl or $(C_1-C_4)$alkoxy; yet more preferably $R^1$ is H or $(C_1-C_4)$alkyl; most preferably $R^1$ is H or $(C_1-C_3)$alkyl, in particular H, methyl or ethyl.

Preferably $R^2$ is H or $(C_1-C_4)$alkyl; more preferably $R^2$ is H.

Preferably $R^1$ and $R^2$ together with the attached carbon atom form a $(C_3-C_6)$cycloalkyl ring, in particular $(C_3-C_4)$cycloalkyl.

Preferably $R^3$ is H, $(C_1-C_4)$alkyl, $(C_1-C_4)$alkoxy or halogen; more preferably $R^3$ is H, $(C_1-C_3)$alkyl, $(C_1-C_4)$alkoxy, Cl or F; yet more preferably $R^3$ is H, $(C_1-C_2)$alkyl, methoxy, chloro or fluoro.

Preferably $R^4$ is H, $(C_1-C_4)$alkyl, $(C_1-C_4)$haloalkyl, $(C_3-C_4)$alkenyl, $(C_3-C_4)$alkynyl or an acyl radical having 1 to 12 carbon atoms, the acyl radical is preferably selected from the group consisting of CHO, —CO$(C_1-C_6)$alkyl, —CO$(C_1-C_6)$haloalkyl, —CO$_2(C_1-C_6)$alkyl, —SO$_2(C_1-C_6)$alkyl, —CO$_2$-phenyl or —CO-phenyl wherein each phenyl is unsubstituted or substituted by one or more radicals selected from the group consisting of halogen, $(C_1-C_2)$alkyl, $(C_1-C_2)$haloalkyl, $(C_1-C_2)$alkoxy, $(C_1-C_2)$haloalkoxy and NO$_2$; more preferably $R^4$ is H, $(C_1-C_3)$alkyl, $(C_1-C_3)$haloalkyl, allyl, propargyl, CHO, —CO$(C_1-C_3)$alkyl or —CO$(C_1-C_3)$haloalkyl; yet more preferably $R^4$ is H, CHO, COCH$_3$, COCH$_2$Cl, COCH(CH$_3$)Cl or COCF$_3$; most preferably $R^4$ is H.

Preferably $R^5$ is H, $(C_1-C_4)$alkyl or $(C_1-C_4)$haloalkyl; more preferably $R^5$ is H or $(C_1-C_2)$alkyl; most preferably $R^5$ is H.

Preferably $R^6$ is H, $(C_1-C_3)$alkyl or $(C_1-C_3)$alkoxy; more preferably $R^6$ is H, methyl or ethyl.

Preferably $R^7$, $R^8$, $R^9$ and $R^{10}$ are each independently H, $(C_1-C_3)$alkyl, halogen or $(C_1-C_3)$alkoxy; more preferably $R^7$, $R^8$, $R^9$ and $R^{10}$ are each independently H, methyl, F or Cl.

Preferably A is CH$_2$ or a direct bond.

Preferred compounds of formula (I) are those in which:
$R^1$ is H, halogen, $(C_1-C_4)$alkyl, such as methyl, ethyl, n-propyl or iso-propyl, or is $(C_1-C_4)$haloalkyl, $[(C_1-C_4)$alkoxy]$(C_1-C_4)$alkyl, $(C_3-C_6)$cycloalkyl which is unsubstituted or substituted by one or two $(C_1-C_4)$alkyl groups, or is $(C_3-C_4)$halocycloalkyl, $(C_2-C_4)$alkenyl, $(C_2-C_4)$haloalkenyl, $(C_2-C_4)$alkynyl, $(C_1-C_4)$alkoxy or $(C_1-C_4)$haloalkoxy;

$R^2$ is H or $(C_1-C_4)$alkyl; or $R^1$ and $R^2$ together with the attached carbon atom form a $(C_3-C_6)$cycloalkyl ring;

$R^3$ is H, $(C_1-C_4)$alkyl, $(C_1-C_2)$alkoxy or halogen (more preferably H, $(C_1-C_3)$alkyl, methoxy, Cl or F);

$R^4$ is H, $(C_1-C_4)$alkyl, $(C_1-C_4)$haloalkyl, $(C_3-C_4)$alkenyl, $(C_3-C_4)$alkynyl or an acyl radical having 1 to 12 carbon atoms (preferably CHO, —CO$(C_1-C_6)$alkyl, —CO$(C_1-C_6)$haloalkyl, —CO$_2(C_1-C_6)$alkyl, —SO$_2(C_1-C_6)$alkyl, —CO$_2$-phenyl or —CO-phenyl wherein each phenyl is unsubstituted or substituted by one or more radicals selected from the group consisting of halogen, $(C_1-C_2)$alkyl, $(C_1-C_2)$haloalkyl, $(C_1-C_2)$alkoxy, $(C_1-C_2)$haloalkoxy and NO$_2$);

$R^5$ is H, $(C_1-C_4)$alkyl or $(C_1-C_4)$haloalkyl;

$R^6$ is H, $(C_1-C_3)$alkyl or $(C_1-C_3)$alkoxy;

$R^7$, $R^8$, $R^9$ and $R^{10}$ are each independently H, $(C_1-C_3)$alkyl, halogen or $(C_1-C_3)$alkoxy; and A is CH$_2$, O or a direct bond (preferably A is CH$_2$ or a direct bond, in particular a direct bond).

More preferred compounds of formula (I) are those in which:
$R^1$ is H or $(C_1-C_3)$alkyl;
$R^2$ is H or $(C_1-C_3)$alkyl; or
$R^1$ and $R^2$ together with the attached carbon atom form a $(C_3-C_4)$cycloalkyl ring;
$R^3$ is H, $(C_1-C_2)$alkyl, methoxy, Cl or F;
$R^4$ is H, $(C_1-C_3)$alkyl, $(C_1-C_3)$haloalkyl, allyl, propargyl, CHO, —CO$(C_1-C_3)$alkyl or —CO$(C_1-C_3)$haloalkyl;
$R^5$ is H or $(C_1-C_2)$alkyl;
$R^6$ is H, $(C_1-C_3)$alkyl or $(C_1-C_3)$alkoxy;
$R^7$, $R^8$, $R^9$ and $R^{10}$ are each independently H, methyl, F and Cl; and
A is CH$_2$, O or a direct bond (preferably A is CH$_2$ or a direct bond, in particular a direct bond).

Especially preferred compounds of formula (I) are those in which:
$R^1$ is H or $(C_1-C_2)$alkyl;
$R^2$ is H or $(C_1-C_2)$alkyl; or
$R^1$ and $R^2$ together with the attached carbon atom form a cyclopropyl ring;
$R^3$ is H, $(C_1-C_2)$alkyl, Cl or F;
$R^4$ is H;
$R^5$ is H;
$R^6$ is H or $(C_1-C_3)$alkyl;
$R^7$, $R^8$, $R^9$ and $R^{10}$ are each independently selected from the group consisting of H, methyl, F and Cl; and
A is CH$_2$, O or a direct bond.

Preferably the radical of the formula CR$^1$R$^2$R$^3$ in formula (I) is a radical selected from the group consisting of $(C_1-C_4)$alkyl, $(C_1-C_4)$haloalkyl, $(C_3-C_4)$cycloalkyl, 1-$(C_1-C_3)$alkyl-$(C_3-C_4)$-cycloalkyl and $(C_3-C_4)$halocycloalkyl, more preferably $(C_1-C_3)$alkyl, $(C_1-C_4)$fluoroalkyl, $(C_1-C_4)$chloroalkyl, $(C_3-C_4)$cycloalkyl, 1-$(C_1-C_3)$alkyl-$(C_3-C_4)$-cycloalkyl, $(C_3-C_4)$-fluorocycloalkyl or $(C_3-C_4)$chlorocycloalkyl, for example radicals such as methyl, ethyl, n-propyl, i-propyl, n-butyl, 2-butyl, i-butyl, tert-butyl, 1-fluoro-ethyl, 1-fluoro-propyl, 1-fluoro-isopropyl, 1-fluoro-n-butyl, 1-chloro-ethyl, 1-chloro-propyl, 1-chloro-isopropyl, 1-chloro-n-butyl, 1-methyl-cyclopropyl, 1-chloro-cyclopropyl or 1-fluoro-cyclopropyl.

A preferred embodiment of the invention relates to optically active compounds of formula (Ia) in which the carbon atoms marked 1 and 1* are both chiral and the carbon atom marked 2 is a chiral:

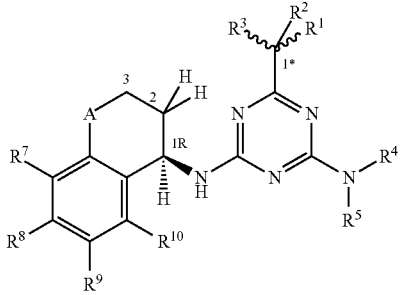

(Ia)

wherein:

$R^1$, $R^2$ and $R^3$ are as defined in formula (I) provided that $R^1$, $R^2$ and $R^3$ are structurally different;

the various other symbols are as defined in formula (I), and the stereochemical configuration at the marked 1 carbon atom is as defined in formula (I), and the stereochemistry at the marked 1* carbon atom is (R) or (S) configuration or a mixture thereof, also including the racemic mixture (R,S), preferably the racemic configuration or an excess of the (R) or (S) configuration from 60 to 100%, especially from 70 to 100%, most preferably from 80 to 100%, based on the total amount of (R) and (S) configuration;

or a salt thereof.

More preferred are compounds of formula (Ia) wherein:

$R^1$ is H, $(C_1\text{-}C_6)$alkyl or $(C_1\text{-}C_6)$alkoxy;

$R^2$ is H or $(C_1\text{-}C_4)$alkyl;

$R^3$ is H, $(C_1\text{-}C_4)$alkyl or halogen;

$R^4$ and $R^5$ are each H;

$R^6$ is H;

$R^7$, $R^8$, $R^9$ and $R^{10}$ are each independently H, $(C_1\text{-}C_6)$alkyl or halogen; and A is $CH_2$, O or a direct bond (more preferably A is $CH_2$ or a direct bond, in particular a direct bond); provided that $R^1$, $R^2$ and $R^3$ are structurally different.

Yet more preferred are compounds of formula (Ia) wherein:

$R^1$ is H, methyl or ethyl;

$R^2$ is H;

$R^3$ is H, F, Cl, methyl or ethyl;

$R^4$ and $R^5$ are each H;

$R^6$ is H;

$R^7$, $R^8$, $R^9$ and $R^{10}$ are each independently selected from the group consisting of H, methyl, Br, Cl or F; and A is $CH_2$, O or a direct bond (more preferably A is $CH_2$ or a direct bond, in particular a direct bond); provided that $R^1$, $R^2$ and $R^3$ are structurally different.

A second preferred embodiment of the invention relates to optically active compounds of formula (Ib) in which the carbon atoms marked 1 and 2 are both chiral and the carbon atom marked 1* is achiral:

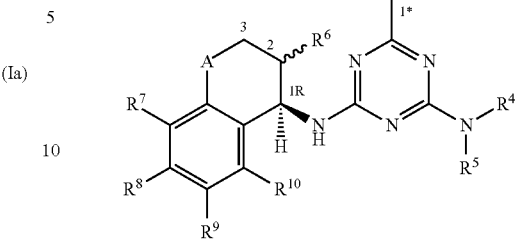

(Ib)

wherein:

$R^1$, $R^2$ and $R^3$ are as defined in formula (I) provided that at least two of $R^1$, $R^2$ and $R^3$ are structurally identical;

$R^6$ is $(C_1\text{-}C_6)$alkyl;

the various other symbols are as defined in formula (I);

and the stereochemical configuration at the marked 1 carbon atom is as defined for formula (I);

and the stereochemistry at the marked 2 carbon atom is (R) or (S) configuration or a mixture thereof, also including the racemic configuration (R,S), preferably the racemic configuration or an excess of the (R) or (S) configuration from 60 to 100%, especially from 70 to 100%, most preferably from 80 to 100%, based on the total amount of (R) and (S) configuration;

or a salt thereof.

Also preferred are compounds of formula (Ib) wherein:

$R^1$ is H, $(C_1\text{-}C_6)$alkyl or $(C_1\text{-}C_6)$alkoxy;

$R^2$ is H or $(C_1\text{-}C_4)$alkyl; or $R^1$ and $R^2$ can together with the attached carbon atom form a $(C_3\text{-}C_6)$cycloalkyl ring;

$R^3$ is H, $(C_1\text{-}C_4)$alkyl or halogen;

$R^4$ and $R^5$ are each H;

$R^6$ is $(C_1\text{-}C_6)$alkyl;

$R^7$, $R^8$, $R^9$ and $R^{10}$ are each independently H, $(C_1\text{-}C_6)$alkyl or halogen; and A is $CH_2$, O or a direct bond (more preferably A is $CH_2$ or a direct bond, in particular a direct bond); provided that at least two of $R^1$, $R^2$ and $R^3$ are structurally identical.

Yet more preferred are compounds of formula (Ib) wherein:

$R^1$ is H, methyl or ethyl;

$R^2$ is H;

$R^3$ is H, F, Cl, methyl or ethyl;

$R^4$ and $R^5$ are each H;

$R^6$ is $(C_1\text{-}C_4)$alkyl;

$R^7$, $R^8$, $R^9$ and $R^{10}$ are each independently selected from the group consisting of H, methyl, Br, Cl or F; and A is $CH_2$, O or a direct bond (more preferably A is $CH_2$ or a direct bond, in particular a direct bond); provided that at least two of $R^1$, $R^2$ and $R^3$ are structurally identical.

A third preferred embodiment of the invention relates to optically active compounds of formula (Ic) in which the carbon atoms marked 1, 2 and 1* are all chiral:

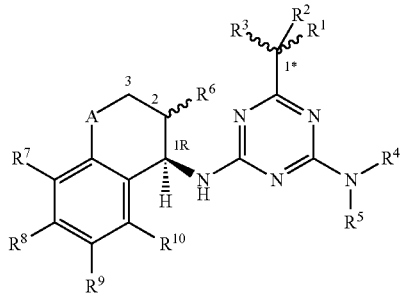

(Ic)

wherein:

$R^1$, $R^2$ and $R^3$ are as defined in formula (I) provided that $R^1$, $R^2$ and $R^3$ are structurally different;

$R^6$ is $(C_1-C_6)$alkyl, preferably $(C_1-C_4)$alkyl;

the various other symbols are as defined in formula (I);

and the stereochemical configuration at the marked 1 carbon atom is as defined for formula (I);

and the stereochemistry at each of the marked 2 and 1* carbon atoms is (R) or (S) configuration or a mixture thereof, also including the racemic configuration (R,S), preferably the racemic configuration or an excess of the (R) or (S) configuration from 60 to 100%, especially from 70 to 100%, most preferably from 80 to 100%, based on the total amount of (R) and (S) configuration;

or a salt thereof.

A fourth preferred embodiment of the invention relates to optically active compounds of formula (I) in which the carbon atom marked 1 is chiral, and the carbon atoms marked 2 and 1* are both achiral:

wherein:

$R^1$, $R^2$ and $R^3$ are as defined in formula (I) provided that at least two of $R^1$, $R^2$ and $R^3$ are structurally identical;

$R^6$ is H;

the various other symbols are as defined in formula (I);

and the stereochemical configuration at the marked 1 position is as defined for formula (I);

or a salt thereof.

Also preferred are compounds of general formula (Id) and (Ie) which are stereoisomers of the compounds of general formula (Ia) wherein the configuration at the carbon atom marked 1* is specifically defined (R) or (S):

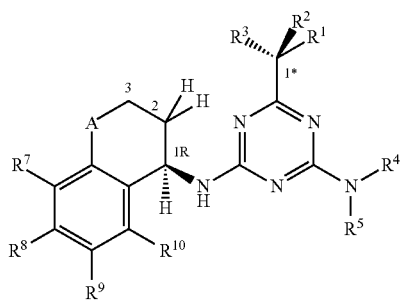

(Id)

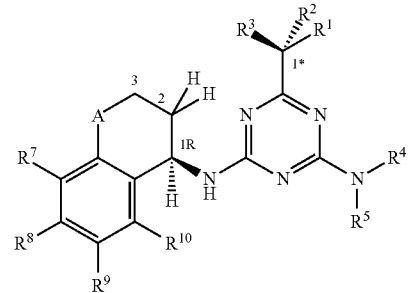

(Ie)

wherein:

$R^1$ is $(C_1-C_6)$alkyl, $(C_1-C_6)$haloalkyl or $(C_3-C_6)$cycloalkyl, preferably $(C_1-C_4)$alkyl, $(C_1-C_4)$haloalkyl or $(C_3-C_6)$cycloalkyl;

$R^2$ is H;

$R^3$ is halogen; and the various other symbols are as defined in formula (I).

Preferred are also compounds of formulae (If), (Ig), (Ih) and (Ii) which are stereoisomers of the compounds of general formula (Ic) wherein the configurations at the carbon atoms marked 1, 2 and 1* are specifically defined:

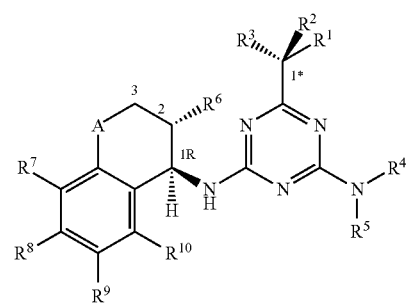

(If)

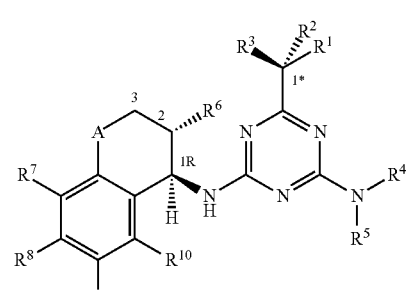

(Ig)

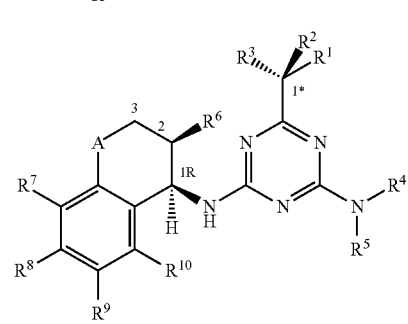

(Ih)

-continued (Ii)

and wherein:
$R^1$ is $(C_1-C_6)$alkyl, $(C_1-C_6)$haloalkyl or $(C_3-C_6)$cycloalkyl;
$R^2$ is H;
$R^3$ is $(C_1-C_4)$alkyl or halogen;
$R^6$ is $(C_1-C_6)$alkyl; and
the various other symbols are as defined in formula (I); provided that $R^1$, $R^2$ and $R^3$ are structurally different.

More preferred are compounds of formula (If), (Ig), (Ih) and (Ii) wherein:
$R^1$ is methyl or ethyl;
$R^2$ is H;
$R^3$ is methyl, ethyl, F or Cl;
$R^4$ and $R^5$ are each H;
$R^6$ is methyl or ethyl; and
$R^7$, $R^8$, $R^9$ and $R^{10}$ are each independently H, methyl, Br, Cl or F; provided that $R^1$, $R^2$ and $R^3$ are structurally different.

Also more preferred are compounds of formula (Id) and (Ie) wherein:
$R^1$ is methyl or ethyl;
$R^2$ is H;
$R^3$ is methyl, ethyl, F or Cl;
$R^4$ and $R^5$ are each H; and
$R^7$, $R^8$, $R^9$ and $R^{10}$ are each independently H, methyl, Br, Cl or F; provided that $R^1$, $R^2$ and $R^3$ are structurally different.

Preferred are also compounds of formula (Ij) which are stereoisomers of the compounds of general formula (Ib) wherein the configurations at the carbon atoms marked 1 and 2 are specifically defined:

(Ij)

wherein:
$R^1$ is H, $(C_1-C_3)$alkyl or $(C_1-C_3)$alkoxy; or
$R^1$ and $R^2$ can together with the attached carbon atom form a $(C_3-C_6)$cycloalkyl ring;
$R^2$ is H or $(C_1-C_3)$alkyl;
$R^3$ is H, halogen or $(C_1-C_3)$alkyl;
$R^6$ is $(C_1-C_6)$alkyl; and
the various other symbols are as defined in formula (I); provided that at least two of $R^1$, $R^2$ and $R^3$ are structurally identical.

Also preferred are compounds of formula (Ij) wherein:
$R^1$ is H, methyl, ethyl, methoxy or Cl;
$R^2$ is H or methyl; or
$R^1$ and $R^2$ can together with the attached carbon atom form a cyclopropyl ring;
$R^3$ is H, methyl, F or Cl;
$R^4$ and $R^5$ are each H;
$R^6$ is methyl; and
$R^7$, $R^8$, $R^9$ and $R^{10}$ are each independently selected from the group consisting of H, methyl, Br, Cl or F.

Compounds of formula (If) and (Ih) are particularly preferred.

Compounds of formula (If) are most preferred.

A further class of preferred compounds are of formula (Ia), (Ib), (Ic), (Id), (Ie), (If), (Ig), (Ih), (Ii) or (Ij) in which the radicals $R^1$, $R^2$, $R^3$, $R^4$, $R^5$, $R^6$, $R^7$, $R^8$, $R^9$, $R^{10}$ and A are as defined in the preferred meanings for formula (I).

A particularly preferred class of compounds are those of formula (If) wherein:
$R^1$ is $(C_1-C_2)$alkyl;
$R^2$ is H;
$R^3$ is $(C_1-C_2)$alkyl, Cl or F;
$R^4$ and $R^5$ are each H;
$R^6$ is $(C_1-C_2)$alkyl;
$R^7$, $R^8$, $R^9$ and $R^{10}$ are each independently H, methyl, F or Cl; and
A is $CH_2$, O or a direct bond (more preferably A is a direct bond); provided that $R^1$, $R^2$ and $R^3$ are structurally different.

Also preferred are compounds of formula (Ia-1), (Ic-1), (Id-1), (Ie-1), (If-1), (Ig-1), (Ih-1), (Ii-1) and (Ij-1) as depicted as head formulae of the tables further below, in which $R^4$ and $R^5$ are each H, and the radicals $R^1$, $R^2$, $R^3$, $R^6$, $R^7$, $R^8$, $R^9$, $R^{10}$ and A are as defined above for the respective basic formulae (Ia), (Ic), (Id), (Ie), (If), (Ig), (Ih), (Ii) and (Ij).

More preferred are compounds of formula (Ia-1), (Id-1) and (Ie-1) as depicted as headformulae of the tables further below, in which:
$R^1$ is $(C_1-C_6)$alkyl;
$R^2$ is H;
$R^3$ is $(C_1-C_6)$alkyl or halogen;
$R^4$ and $R^5$ are each H;
$R^6$ is H; and
$R^7$, $R^8$, $R^9$ and $R^{10}$ are each independently H, $(C_1-C_6)$alkyl or halogen; provided that $R^1$, $R^2$ and $R^3$ are structurally different.

Also more preferred are compounds of formula (Ic-1), (If-1), (Ig-1), (Ih-1) and (Ii-1) as depicted as headformulae of the tables further below, in which:
$R^1$ is $(C_1-C_6)$alkyl;
$R^2$ is H;
$R^3$ is $(C_1-C_6)$alkyl or halogen;
$R^4$ and $R^5$ are each H;
$R^6$ is $(C_1-C_6)$alkyl; and
$R^7$, $R^8$, $R^9$ and $R^{10}$ are each independently H, $(C_1-C_6)$alkyl or halogen; provided that $R^1$, $R^2$ and $R^3$ are structurally different.

Also more preferred are compounds of formula (Ij-1) as depicted as headformulae of the tables further below, in which:
$R^1$ is H, methyl, ethyl, methoxy or Cl;
$R^2$ is H or methyl; or
$CR^1R^2$ is cyclopropyl;
$R^3$ is H, methyl, Cl or F;
$R^4$ and $R^5$ are each H;
$R^6$ is methyl; and
$R^7$, $R^8$, $R^9$ and $R^{10}$ are each independently H, $(C_1-C_6)$alkyl or halogen; provided that at least two of $R^1$, $R^2$ and $R^3$ are structurally identical.

Also preferred are compounds of formula (Ik), (IL), (Im), (In), and (Ip) as depicted as headformulae of the tables further below, in which the radicals $R^1$ to $R^{10}$ and A are as defined above in the preferred meanings of the corresponding general formula.

More preferred are compounds of formula (Ik) as depicted as headformulae of the tables further below, in which:
$R^1$ is H, $(C_1\text{-}C_6)$alkyl, halogen or $(C_1\text{-}C_6)$alkoxy;
$R^2$ is H or $(C_1\text{-}C_6)$alkyl; or
$CR^1R^2$ is cyclopropyl;
$R^3$ is H, $(C_1\text{-}C_6)$alkyl or halogen;
$R^4$ and $R^5$ are each H;
$R^6$ is H;
$R^7$, $R^8$, $R^9$ and $R^{10}$ are each independently H, $(C_1\text{-}C_6)$alkyl or halogen; and at least two of $R^1$, $R^2$ and $R^3$ are structurally identical.

Also more preferred are compounds of formula (IL), (Im), (In), and (Ip) as depicted as headformulae of the tables further below, in which:
$R^1$ is $(C_1\text{-}C_6)$alkyl;
$R^2$ is H;
$R^3$ is halogen;
$R^4$ and $R^5$ are each H;
$R^6$ is $(C_1\text{-}C_6)$alkyl;
$R^7$, $R^8$, $R^9$ and $R^{10}$ are each independently H, $(C_1\text{-}C_6)$alkyl or halogen.

Preferred compounds of formula (I) are optically active indanylamino-1,3,5-triazine derivatives of formula (I) (A=direct bond). Also preferred are optically active chroman-4-ylamino-1,3,5-triazine derivatives of formula (I) (A=oxygen atom) and optically active tetrahydronaphthalinylamino-1,3,5-triazine derivatives of formula (I) (A=methylene).

Compounds of formula (I) above may be prepared by the application or adaptation of known methods (i.e. methods heretofore used or described in the literature), for example as generally described in WO 97/31904 or WO 97/29095, and references cited therein, and as hereinafter described.

In the following description where symbols appearing in formulae are not specifically defined, it is to be understood that they are "as hereinbefore defined" in accordance with the first definition of each symbol in the specification, or preferably the preferred definitions mentioned.

It is to be understood that in the descriptions of the following processes the sequences may be performed in different orders, and that suitable protecting groups may be required to achieve the compounds sought.

According to a feature of the present invention compounds of formula (I) may be prepared by the reaction of a compound of general formula (II):

(II)

wherein $R^1$, $R^2$ and $R^3$ are as defined in formula (I), and Z is a functional group selected from the group consisting of carboxylic ester, carboxylic orthoester, carboxylic acid chloride, carboxamide, cyano, carboxylic anhydride or trichloromethyl, with a biguanidine compound of formula (III) or an acid addition salt thereof:

(III)

wherein $R^4$, $R^5$, $R^6$, $R^7$, $R^8$, $R^9$, $R^{10}$ and A and the configuration at the marked 1 position are as defined in formula (I). The reaction is generally performed in the presence of a base, in an inert solvent such as tetrahydrofuran, dioxan, acetonitrile, N,N-dimethylformamide, methanol or ethanol, at a temperature of from 0° C. to the reflux temperature of the solvent, preferably at 20° C. to 60° C. The base is generally an alkali metal hydroxide, alkali metal hydride, alkali metal carbonate, alkali metal alkoxide, alkaline earth metal carbonate, or an organic base such as a tertiary amine for example triethylamine, or 1,8-diazabicyclo[5.4.0]undec-7-en (DBU).

According to a further feature of the present invention said compounds of formula (I) may also be prepared by the reaction of a compound of general formula (IV):

(IV)

wherein $R^1$, $R^2$, $R^3$, $R^4$ and $R^5$ and the configuration at the marked 1* position are as defined in formula (I), and $L^1$ is a leaving group such as chlorine, trichloromethyl, $(C_1\text{-}C_4)$-alkylsulfonyl, phenylsulfonyl or $(C_1\text{-}C_4)$alkyl-phenylsulfonyl, with an amine of formula (V) or an acid addition salt thereof:

(V)

wherein $R^6$, $R^7$, $R^8$, $R^9$, $R^{10}$ and A and the configuration at the marked 1 position are as defined in formula (I). The reaction is generally performed in the presence of a base, in an inert solvent, e.g. a polar organic solvent such as tetrahydrofuran, dioxan, acetonitrile, N,N-dimethylformamide, methanol or ethanol, at a temperature of from 0° C. to the reflux temperature of the solvent, preferably at 20° C. to 100° C. The base is generally an alkali metal hydroxide, alkali metal hydride, alkali metal carbonate, alkali metal alkoxide, alkaline earth metal carbonate, or an organic base such as a tertiary amine for example triethylamine, or 1,8-diazabicyclo[5.4.0]undec-7-en (DBU).

The process is known in general terms from for example Comprehensive Heterocyclic Chemistry, A. R. Katritzky and C. W. Rees, Pergamon Press, Oxford, New York, 1984, Vol. 3; Part 2B; ISBN 0-08-030703-5, S. 482.

According to a further feature of the present invention where one of $R^4$ or $R^5$ in formula (I) is $(C_1-C_4)$alkyl, $(C_1-C_4)$haloalkyl, $(C_3-C_4)$alkenyl, $(C_3-C_4)$haloalkenyl, $(C_3-C_4)$alkynyl or $(C_3-C_4)$haloalkynyl, invention compounds of formula (I) may be prepared by the reaction of the corresponding compound of formula (I) wherein said $R^4$ or $R^5$ respectively is H, and the other radicals and the configurations are as defined in formula (I), with an alkylating agent of formula (VI) or (VII) respectively:

$R^4$-$L^2$              (VI)

$R^5$-$L^2$              (VII)

wherein $L^2$ is a leaving group, generally halogen, preferably chlorine, bromine or iodine, or an alkyl- or phenyl-sulfonyloxy moiety such as methyl sulfonyloxy or 4-toluenesulfonyloxy. The reaction is generally performed in an inert solvent such as tetrahydrofuran, dioxan, acetonitrile or N,N-dimethylformamide at a temperature of from 0° C. to the reflux temperature of the solvent, preferably at 20° C. to 100° C.

According to a further feature of the present invention compounds of formula (I), wherein one of $R^4$ or $R^5$ is an acyl radical, may be prepared by the reaction of the corresponding compound of formula (I) wherein said $R^4$ or $R^5$ respectively is H, and the other radicals and the configurations are as defined in formula (I), with an acylating agent of formula (VIII) or (IX) respectively:

$R^4$-$L^3$              (VIII)

$R^5$-$L^3$              (IX)

wherein $R^4$ and $R^5$ are each an acyl radical as defined in formula (I) and $L^3$ is a leaving group, generally halogen, preferably chlorine; or with a formylating agent such as formic acid-acetic anhydride. A base is optionally used for the acylation reaction and is generally chosen from an alkali metal hydroxide, alkali metal hydride, alkali metal carbonate, alkali metal alkoxide, alkaline earth metal carbonate, or an organic base such as a tertiary amine for example triethylamine.

The reaction is generally performed in an inert solvent such as tetrahydrofuran, dioxan, acetonitrile or N,N-dimethylformamide at a temperature of from 0° C. to the reflux temperature of the solvent, preferably at 20° C. to 100° C.

Intermediates of formula (III) may be prepared by the reaction of a compound of formula (X):

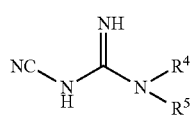

(X)

with a compound of said formula (V). The reaction is generally performed using an acid addition salt, for example the hydrochloride salt of the compound of formula (X), in a solvent such as 1,2-dichlorobenzene, decalin or white mineral oil, at a temperature of from 20° C. to the reflux temperature of the solvent, preferably at 50° C. to 200° C.

Intermediates of formula (V) may be prepared according to known methods, for example by the reductive amination, optionally asymmetric reductive amination, of ketones of formula (XI) or the corresponding oximes:

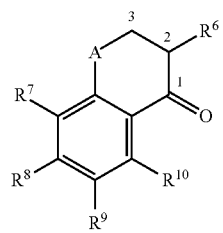

(XI)

in which $R^6$, $R^7$, $R^8$, $R^9$, $R^{10}$ and A are as defined in formula (I), or the reaction of compounds of formula (XII):

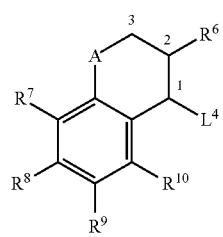

(XII)

in which
$R^6$, $R^7$, $R^8$, $R^9$, $R^{10}$ and A are as defined in formula (I) and $L^4$ is a leaving group such as halogen, hydroxy, methyl sulfonyloxy or 4-toluenesulfonyloxy, with ammonia or a salt thereof, according to known procedures for example as described in patent publication number WO 97/031904.

For the preparation of compounds of formula (I), in which one or more asymmetric carbon atoms is present as a single enantiomeric form, the above processes can be adapted by employing the appropriate enantiomeric or diastereomeric form of the compounds of formula (II), (III), (IV), (V), (VI), (VII) or (XII).

Compounds of formula (II) in an enantiomerically pure form are known or can be prepared according to known procedures, for example as described in Tetrahedron Asymmetry 1994, 5, 981, J. Chem. Soc. Perkin Trans I, 1979, 2248 and the literature cited therein.

The preparation of compounds of formula (I) in resolved form or partially resolved form may, for example, be carried out by following the above-defined processes using one or more intermediates (II), (III), (IV) or (V) whose configuration differs from the configuration as defined in the compound of formula (I) to be prepared, and resolving the mixture obtained according to known methods of resolution.

It is generally possible to use customary methods for optical resolutions (cf. Textbooks of Stereochemistry), for example following processes for separating mixtures into diastereomers, for example physical processes, such as crystallization, chromatographic processes, in particular column chromatography and high pressure liquid chromatography, distillation, if appropriate under reduced pressure, extraction and other processes, it is possible to separate the remaining mixtures of enantiomers, generally by chromatographic separation on chiral solid phases. Suitable for preparative amounts or use on an industrial scale are processes such as the crystallization of diastereomeric salts which can be obtained from the compounds (I) using optically active acids and, if appropriate, provided that acidic groups are present, using optically active bases.

Optically active acids which are suitable for optical resolution by crystallization of diastereomeric salts are, for example, camphorsulfonic acid, camphoric acid, bromocamphorsulfonic acid, quinic acid, tartaric acid, dibenzoyltartaric acid and other analogous acids; suitable optically active bases are, for example, quinine, cinchonine, quinidine, brucine, 1-phenylethylamine and other analogous bases.

The crystallizations are then in most cases carried out in aqueous or aqueous-organic solvents, where the diastereomer which is less soluble precipitates first, if appropriate after seeding. One enantiomer of the compound of the formula (I) is then liberated from the precipitated salt, or the other is liberated from the crystals, by acidification or using base.

Enantiomerically pure amine intermediates of formula (V) may be prepared using known methods, for example as described in Houben-Weyl, Methoden der Organischen Chemie, 4. Auflage, Band E 21b, 1833 ff. or Band E 21e, 5133.

One of the preferred procedures is the reductive amination of ketones of formula (XI) with asymmetric catalysis, including enzymatic transamination. Another procedure for the preparation of enantiomerically pure amines of formula (V), is the racemate cleaving method described in *J. Prakt. Chem.* 339, (1997), pages 381-384, or a procedure described in Org. Lett., Vol. 3, Nr. 25, page 4101. In this procedure the racemic amine of the general formula (V) is acylated enantioselectively with an acylating agent such as an optionally substituted fatty acid ester (preferably methyl chloroacetate or ethyl chloroacetate or methyl methoxyacetate or ethyl methoxyacetate) in the presence of a biocatalyst. The non-acylated enantiomer is then separated by simple treatment with mineral acid. The acylated amine enantiomer is then cleaved back to the corresponding amine, using a base for example an alkali metal hydroxide such as sodium hydroxide, or an acid, for example a mineral acid such as hydrogen chloride.

As biocatalysts, lipases, for example *Pseudomonas cepacia*, *Candida cylindracea* or *Candida antarctica*, are particularly suitable for this purpose. Certain of these lipases are also commercially available in immobilized form (brand name: "Novozym 435").

By analogy with said enzymatic acylation method the compounds of formula (XIII) or (XIV) can be prepared as intermediates by acylation of racemic amines corresponding to compounds of formula (V), in principle,

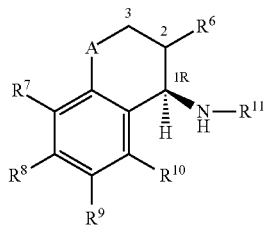

(XIII)

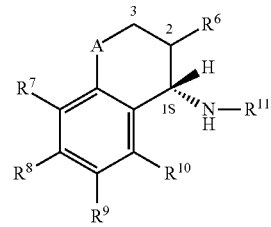

(XIV)

wherein $R^6$, $R^7$, $R^8$, $R^9$, $R^{10}$ and A are as defined in formula (I), and $R^{11}$ is acyl, preferably $(C_1-C_6)$alkanoyl which is unsubstituted or substituted by one or more radicals selected from the group consisting of halogen, $(C_1-C_4)$alkoxy and $(C_1-C_4)$alkylthio; more preferably formyl, acetyl, propionyl, haloacetyl, halopropionyl, $(C_1-C_4)$alkoxyacetyl or $(C_1-C_4)$alkoxypropionyl, most preferably chloroacetyl or methoxyacetyl;

the desired optical isomer (V) is then obtained by cleaving compound (XIII) by using mineral acid, or, in the case when acylated compound (XIV) is formed enzymatically, using the non-acylated amine (V) directly.

The following acids, for example, are suitable for preparing the acid addition salts of the compounds of the formula (I): hydrohalic acids, such as hydrochloric acid or hydrobromic acid, furthermore phosphoric acid, nitric acid, sulfuric acid, mono- or bifunctional carboxylic acids and hydroxycarboxylic acids, such as acetic acid, oxalic acid, maleic acid, succinic acid, fumaric acid, tartaric acid, citric acid, salicylic acid, sorbic acid or lactic acid, and also sulfonic acids, such as p-toluenesulfonic acid and 1,5-naphthalenedisulfonic acid. The acid addition compounds of the formula (I) can be obtained in a simple manner by the customary methods for forming salts, for example by dissolving a compound of the formula (I) in a suitable organic solvent, such as, for example, methanol, acetone, methylene chloride or benzene, and adding the acid at temperatures from 0 to 100° C., and they can be isolated in a known manner, for example by filtration, and, if appropriate, purified by washing with an inert organic solvent.

The base addition salts of the compounds of the formula (I) are preferably prepared in inert polar solvents such as, for example, water, methanol or acetone at temperature from 0 to 100° C. Examples of suitable bases for preparing the salts according to the invention are alkali metal carbonates, such as potassium carbonate, alkali metal and alkaline earth metal hydroxides, for example NaOH or KOH, alkali metal and alkaline earth metal hydrides, for example NaH, alkali metal and alkaline earth metal alkoxides, for example sodium methoxide, potassium tert-butoxide, or ammonia or ethanolamine. Quaternary ammonium salts can be obtained, for example, by salt exchange or condensation with quaternary ammonium salts of the formula [NRR'R" R'"]$^+$X$^-$ where R, R', R" and R'" independently of one another are $(C_1-C_4)$alkyl, phenyl or benzyl and X$^-$ is an anion, for example Cl$^-$ or OH$^-$.

Some of the compounds of formula (III) and (V) in which one or more asymmetric carbon atoms are present as a single or optically enriched enantiomeric form are novel and as such form a further feature of the invention, and may be prepared as described above. The following amines of formula (V) are known:
a) indanes:
- (1R)-1-amino-indane (Chem.Abstracts Registry No. 10277-744);
- (1R)-1-amino-7-methoxy-indane (Arch. Pharm. 331 (1998) 59-71);
- (1R)-1-amino-7-n-propoxy-indane (Arch. Pharm. 331 (1998) 59-71);
- (1R)-1-amino-7-cyano-indane (Arch. Pharm. 331 (1998) 59-71);

b) tetrahydonaphthalenes:
- (1R)-1-amino-1,2,3,4-tetrahydonaphthalene (Chem.Abstracts Registry No. 2335746-2);
- (1R)-1-amino-7-methyl-1,2,3,4-tetrahydonaphthalene (WO-98/47877);
- (1R)-1-amino-7-methoxy-1,2,3,4-tetrahydonaphthalene (WO-98/47877);
- (1R)-1-amino-7-isopropyl-1,2,3,4-tetrahydonaphthalene (WO-98/47877);
- (1R)-1-amino-7-t-butyl-1,2,3,4-tetrahydonaphthalene (WO-98/47877);
- hydrochloride salts of the latter two compounds (WO-98/47877);
- (1R)-1-amino-6,8-dimethyl-1,2,3,4-tetrahydonaphthalene (J. of Chromatography 959 (2002) 75-83), c) chromanes:
- (4R)₄-amino-chromane (Beilstein Registry No. 7687402 and/or 7687403);

Therefore, a further feature of the invention thus relates to compounds of formula (III) or (V), or salts thereof, wherein $R^6$ is H, ($C_1$-$C_6$)alkyl or ($C_1$-$C_6$)alkoxy;
$R^7$, $R^8$, $R^9$ and $R^{10}$ are each independently H, ($C_1$-$C_4$)alkyl, ($C_1$-$C_3$)haloalkyl, halogen, ($C_1$-$C_3$)alkoxy, ($C_1$-$C_3$)haloalkoxy or CN;
A is $CH_2$, O or a direct bond; and wherein the stereochemical configuration at the marked 1 position is as defined in formula (I),
with the exception of compounds of formula (V), or salts thereof, where:
(i) A is a direct bond, $R^6$, $R^7$, $R^8$ and $R^9$ are each hydrogen, and $R^{10}$ is hydrogen, methoxy, n-propoxy or cyano; or
(ii) A is $CH_2$, and $R^6$, $R^7$, $R^8$ and $R^{10}$ are each hydrogen, and $R^9$ is hydrogen, methyl, methoxy, isopropoxy or t-butyl; or A is $CH_2$, and $R^6$, $R^7$ and $R^9$ are each hydrogen, and $R^8$ is methyl and $R^{10}$ is methyl; or
(iii) A is an oxygen atom, and $R^6$, $R^7$, $R^8$, $R^9$ and $R^{10}$ are each H.

A preferred class of novel intermediate compounds of formula (III) and (V), or salts thereof, are those wherein:
$R^6$, $R^7$ and $R^{10}$ are each independently H or methyl;
$R^8$ is H, methyl, Cl or F;
$R^9$ is H, methyl, Cl, F or Br; and
A is a direct bond, $CH_2$ or 0; and the stereochemical configuration at the marked 1 and position is as defined in formula (I), with the exception of compounds of formula (V), or salts thereof, where:
(i) A is a direct bond, $R^6$, $R^7$, $R^8$ and $R^9$ are each hydrogen, and $R^{10}$ is hydrogen, or
(ii) A is $CH_2$, and $R^6$, $R^7$, $R^8$ and $R^{10}$ are each hydrogen, and $R^9$ is hydrogen or methyl, or
(iii) A is an oxygen atom, and $R^6$, $R^7$, $R^8$, $R^9$ and $R^{10}$ are each H.

A more preferred class of novel intermediate compounds of formula (III) and (V), or salts thereof, are those wherein:
A is a direct bond,
$R^6$ is H or methyl;
$R^7$ and $R^{10}$ are hydrogen,
$R^8$ is H, methyl, Cl or F;
$R^9$ is methyl, Cl, F or Br; and
the stereochemical configuration at the marked 1 and position is as defined in formula (I).

Further preferred classes of novel intermediate compounds of formula (Va) and (Vb), or salts thereof:

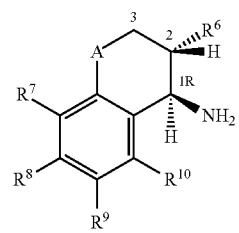

(Va)

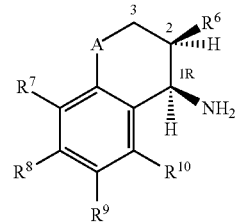

(Vb)

wherein:
$R^6$ is methyl;
$R^7$ and $R^{10}$ are each independently H or methyl;
$R^8$ is H, methyl, Cl or F;
$R^9$ is H, methyl, Cl, F or Br; and
A is a direct bond, $CH_2$ or O; and as such form a further feature of the invention.

Some of the compounds of formula (XIII) (amides) which can be used as intermediates for the preparation of the optically active aminesf formula (V) or biguanides of formula (III) in which one or more asymmetric carbon atoms are present as a single or optically enriched enantiomeric form are novel and as such form a further feature of the invention, and may be prepared as described above. The following acylated amines of formula (XIII) are already known:
a) indanes:
- (1R)-1-acetylamino-indane (Chem. Europe 6 (2000, 1840-1846);
- (1R)-1-formylamino-indane (J. Am. Chem. Soc. 88 (1966) 2233-2240)
- (1R)-1-(trifluoroacetylamino)-indane (J. Med. Chem. 45 (2002) 5260-5279 or U.S. Pat. No. 4,948,395)
- (1R)-1-(bromoacetylamino)-indane (Biochemistry 1980, 2140-2144);
- (1R)-1-acetylamino-2-methyl-indane (J. Org. Chem. 1999, 1774-1775);
- (1R)-1-acetylamino-5-fluoro-indane (J. Org. Chem. 1999, 1774-1775);

b) tetrahydonaphthalenes:
- (1R)-1-acetylamino-1,2,3,4-tetrahydonaphthalene (J. Org. Chem. 1999, 1774-1775 or Tetrahedron Left. 43 (2002) 5260);
- (1R)-1-acetylamino-6-methoxy-1,2,3,4-tetrahydonaphthalene (J. Org. Chem. 1999);
- (1R)-1-acetylamino-5,7-dimethyl-1,2,3,4-tetrahydonaphthalene (J. Org. Chem. 1999, 1774-1775);

(1R)-1-(chloroacetylamino)-1,2,3,4-tetrahydonaphthalene (Farmaco. ED. Sci. Vol. 26 (1971)474-486);
(1R)-1-(trifluoroacetylamino)-1,2,3,4-tetrahydonaphthalene (U.S. Pat. No. 4,948,395);
c) chromanes:
(4R)-4-acetylamino-chromane (Org. Left. 4 (2002) 1695-1668);

A further feature of the invention are thus novel compounds of formula (XIII) or salts thereof, wherein
$R^6$ is H, $(C_1-C_6)$alkyl or $(C_1-C_6)$alkoxy;
$R^7$, $R^8$, $R^9$ and $R^{10}$ are each independently H, $(C_1-C_4)$alkyl, $(C_1-C_3)$haloalkyl, halogen, $(C_1-C_3)$alkoxy, $(C_1-C_3)$haloalkoxy or CN;
$R^{11}$ is acyl, preferably $(C_1-C_6)$alkanoyl which is unsubstituted or substituted by one or more radicals selected from the group consisting of halogen, $(C_1-C_4)$alkoxy and $(C_1-C_4)$alkylthio; more preferably formyl, acetyl, propionyl, haloacetyl, halopropionyl, $(C_1-C_4)$alkoxyacetyl or $(C_1-C_4)$alkoxypropionyl, most preferably chloroacetyl or methoxyacetyl;
A is $CH_2$, O or a direct bond; and wherein the stereochemical configuration at the marked 1 position is as defined in formula (I),
with the exception of compounds, or salts thereof, where:
(i) A is a direct bond, $R^6$, $R^7$, $R^8$, $R^9$ and $R^{10}$ are each hydrogen, and $R^{11}$ is formyl, acetyl, trifluoroacetyl or bromoacetyl, or
A is a direct bond, $R^6$ is methyl; $R^7$, $R^8$, $R^9$ and $R^{10}$ are each hydrogen, and $R^{11}$ is acetyl, or
A is a direct bond, $R^6$; $R^7$, $R^9$ and $R^{10}$ are each hydrogen, $R^8$ is fluoro, and $R^{11}$ is acetyl, or
(ii) A is $CH_2$, and $R^6$, $R^7$, $R^8$, $R^9$ and $R^{10}$ are each hydrogen, and $R^{11}$ is acetyl, trifluoroacetyl or chloroacetyl; or
A is $CH_2$, and $R^6$, $R^7$ and $R^9$ are each hydrogen, and $R^8$ is methyl and $R^{10}$ is methyl; and $R^{11}$ is acetyl, or
A is $CH_2$, and $R^6$, $R^7$, $R^9$ and $R^{10}$ are each hydrogen, and $R^8$ is methoxy, and $R^{11}$ is acetyl, or
A is $CH_2$, and $R^6$ is methyl, $R^7$, $R^8$, $R^9$ and $R^{10}$ are each hydrogen, and $R^{11}$ is acetyl, or
(iii) A is an oxygen atom, and $R^6$, $R^7$, $R^8$, $R^9$ and $R^{10}$ are each H, and $R^{11}$ is acetyl.

Compounds of formula (II), (IV), (VI), (VII), (VIII), (IX), (X), (XI) and (XII), as well as racemic (III) and (V) are known or may be prepared analogously to known methods.

A collection of compounds of formula (I) which can be synthesized by the abovementioned processes can additionally be prepared in parallel fashion, which can be effected manually, partly automated or fully automated. In this context, it is possible to automate the procedure of the reaction, work-up or purification of the products or intermediates. In total, this is to be understood as meaning a procedure which is described, for example, by S. H. DeWitt in "Annual Reports in Combinatorial Chemistry and Molecular Diversity: Automated Synthesis", Volume 1, published by Escom, 1997, pages 69 to 77.

For carrying out the reaction and work-up in parallel fashion, a series of commercially available apparatuses can be used as they are available from, for example, Stem Corporation, Woodrolfe Road, Tollesbury, Essex, CM9 8SE, England or H+P Labortechnik GmbH, Bruckmannring 28, 85764 Oberschleissheim, Germany. To carry out the parallel purification of compounds (I) or of intermediates obtained during the preparation, there are available, inter alia, chromatographic equipment, for example from ISCO, Inc., 4700 Superior Street, Lincoln, Nebr. 68504, USA. The equipment mentioned makes possible a modular procedure, where the individual steps are automated, but manual operation has to be carried out between the steps. This can be circumvented by employing partly or fully integrated automation systems, in which the automation modules in question are operated by, for example, robots. Such automation systems can be obtained from, for example, Zymark Corporation, Zymark Center, Hopkinton, Mass. 01748, USA.

In addition to the above-described methods, compounds of formula (I) can be prepared in full or partly by solid-phase supported methods. To this end, individual intermediates or all intermediates of the synthesis or of a synthesis adapted to the procedure in question are bound to a synthesis resin. Solid-phase supported synthetic methods are described extensively in the specialist literature, for example: Barry A. Bunin in "The Combinatorial Index", published by Academic Press, 1998.

The use of solid-phase supported synthesis methods permits a series of protocols known from the literature which, in turn, can be carried out manually or in an automated fashion. For example, the "teabag method" (Houghten, U.S. Pat. No. 4,631,211; Houghten et al., Proc. Natl. Acad. Sci., 1985, 82, 5131-5135) can be partly automated with products of IRORI, 11149 North Torrey Pines Road, La Jolla, Calif. 92037, USA. Solid-phase supported parallel synthesis can be automated successfully for example using equipment by Argonaut Technologies, Inc., 887 Industrial Road, San Carlos, Calif. 94070, USA or MultiSynTech GmbH, Wullener Feld 4, 58454 Witten, Germany.

The preparation in accordance with the processes described herein yields compounds of formula (I) in the form of substance collections or substance libraries. Subject matter of the present invention are therefore also libraries of the compounds of formula (I) which contain at least two compounds of formula (I), and of their precursors.

The following non-limiting Examples illustrate the preparation of the compounds of formula (I).

A. CHEMICAL EXAMPLES

In the Examples which follow, quantities (also percentages) are weight based unless stated otherwise. Ratios of solvents are volume based.

The optical rotation is measured as specific rotation $[\alpha]$ of the polarized light of 589 nm wavelength (polarized Na-D light) under standard conditions (c=1 g/ml, t=25° C.). The solvent is chloroform unless indicated otherwise.

Example A1

2-Amino-4-[(1R)-1-indanylamino]-6-methyl-1,3,5-triazine (Table 8, Compound number 8.1)

A mixture of 2-amino-4-chloro-6-methyl-1,3,5-triazine (2.2 g, 0.015 mol), R(−)-1-aminoindane (2.0 g, 0.015 mol) and potassium carbonate (4.6 g, 2.2 mol) in N, N-dimethylformamide was stirred for 5 hours at 90-100° C. When the reaction was complete, the solvent was evaporated in vacuo below 100° C., the mixture obtained was cooled and water was added. Ethyl acetate was added and the organic layer separated, dried (sodium sulfate) and evaporated. The residue was purified by column chromatography, eluting with ethyl acetate to give 2-amino-4-[(1R)-1-indanylamino]-6-methyl-1,3,5-triazine (3.5 g, 95% yield, Compound number 8.1), mp.

94-96° C., chemical purity>95%, ee 91% by HPLC, optical rotation (CHCl$_3$, c=1): +87.4°).

Example A2

2-Amino-4-[(4R)$_4$-chromanylamino]-6-[(1R)-1-fluoroethyl]-1,3,5-triazine (Table 1, Compound number 1.20)

a. chroman-4-one oxime

A mixture of sodium acetate (41.53 g, 0.506 mol) in water at 60° C. was combined with a stirred mixture of chroman-4-one (25 g, 0.169 mol) and hydroxylamine hydrochloride (20.0 g, 0.287 mol) in ethanol at 60° C. The resulting mixture was heated at reflux for 90 minutes, cooled and filtered. The crude solid was washed with water to give chroman-4-one oxime (27.9 g, yield 96%), mp. 114-117° C., purity 95%.

b. 4-aminochromane hydrochloride

Chroman-4-one oxime (27.9 g, 0.157 mol) in ethanol was added to Raney-nickel catalyst (3.0 g) in ethanol under nitrogen. The mixture was stirred and hydrogen introduced until the theoretical amount (appoximatly 3.6 l) was adsorbed. The catalyst was filtered, the solvent evaporated and 6N ethanolic hydrochloric acid solution (25 ml) added. The solvent was evaporated and the residue washed with diethylether/acetone (10:1) and refiltered to give 4-aminochromane hydrochloride (18.3 g, yield 58%), mp. 220-226° C., purity 95%.

c. N-[(4R)-4-chromanyl]-2-methoxyacetamide

A mixture of 4-aminochromane hydrochloride (27.8 g, 0.15 mol) and aqueous sodium hydroxide (2N) was extracted with ethyl acetate and the organic layer dried (sodium sulfate) and evaporated to give racemic 4-aminochromane (14.2 g, 0.095 mol). To this was added methyl 2-methoxyacetate (10.94 g, 0.105 mol) and 2.5 g Novozym 435 (Aldrich Corp.) in tert-butyl methyl ether, and the mixture heated at reflux for 2 hours. A further addition of Novozym 435 (0.5 g) was made and heating continued until the reaction was complete as judged by hplc. Dichloromethane was added, the biocatalyst filtered off and the organic layer dried (sodium sulfate) and evaporated. The residue was dissolved in the minimum of dichloromethane, and ethanolic hydrochloric acid solution (8N) was added to give (4S)$_4$-aminochromane hydrochloride which was filtered off, and the filtrate evaporated to give N-[(4R)$_4$-chromanyl]-2-methoxyacetamide (8.2 g), mp. 109-112° C.

d. (4R)$_4$-aminochromane hydrochloride

A solution of the above N-[(4R)$_4$-chromanyl]-2-methoxyacetamide (2.2 g, 0.0325 mol) in ethanol (100 ml) and concentrated hydrochloric acid (30 ml) was heated at reflux for 12 hours, then evaporated. A small amount of ethyl acetate was added to the residue and the solid filtered off to give (4R)$_4$-aminochromane hydrochloride (2.3 g), m.p. 261-263° C., chemical purity>95%.

e. (4S)-4-(bisguanidino)chromane hydrochloride

A homogeneous mixture of (4R)-3,4-dihydro-2H-4-chromanylammonium chloride (2.3 g, 0.0124 mol) and 1-cyanoguanidine (1.04 g, 0.0124 mol) in 1,3-dichlorobenzene was heated at 140-150 CC for 150 minutes. The cooled mixture was diluted with toluene and filtered to give (4S)-4-(bisguanidino)chromane hydrochloride (3.3 g, yield 89.4%) as a solid, purity 90%.

f. 2-amino-4-[(4R)$_4$-chromanylamino]-6-[(1R)-1-fluoroethyl]-1,3,5-triazine A 30% solution of sodium methoxide in methanol (0.7 g, 0.75 ml, 0.004 mol) was added to a stirred suspension of (4S)-4-(bisguanidino)chromane hydrochloride (1.1 g, 0.004 mol) in methanol. Then methyl(2R)-2-fluoropropanoate (1.08 g, 0.01 mol) was added at room temperature, followed by an additional amount of a 30% solution of sodium methoxide (1.0 g, 1.0 ml, 0.006 mol). After 4 hours at room temperature the mixture was filtered, the filtrate evaporated and the residue dissolved in ethyl acetate. The organic phase was washed (water), dried (sodium sulfate) and evaporated. The residue was purified by column chromatography, eluting with a 7:3 mixture of ethyl acetate:heptane to give 2-amino-4-[(4R)$_4$-chromanylamino]-6-[(1R)-1-fluoroethyl]-1,3,5-triazine (0.3 g, yield 25%, Compound number 1.20), m.p. 110-112° C., optical rotation (dichloromethane, c=1): +75.4°, purity 98.35% (hplc, Chiralcel OD, 250×4.6 mm, eluent n-hexane:2-propanol 90:10, 0.6 ml/min, rt 21.4 min.).

Example A3

2-Amino-4-[(1R,2S)-2-methyl-1-indanylamino]-6-[(1R)-1-fluoroethyl]-1,3,5-triazine (Table 2, Compound number 2.1)

a. 2-methyl-indan-1-one oxime

A mixture of 2-methyl-1-indanone (10 g, 0.0684 mol) and hydroxylamine hydrochloride (9.5 g, 0.1368 mol) in ethanol was stirred at 60° C., and a solution of sodium acetate (16.8 g, 0.2052 mol) in water added. The resulting mixture was then heated at reflux for 90 minutes, then cooled and the solid filtered. The crude product was washed with water and filtered to give 2-methyl-indan-1-one oxime (9.9 g, yield 81%), mp. 82-91° C., in 90% purity.

b. 1-(RS)(+−)-1-amino-2-methylindane hydrochloride

A mixture of the above 2-methylindan-1-one oxime (9.5 g, 0.0589 mol) and palladium on charcoal catalyst (10% 1.0 g) in methanol and acetic acid was stirred under nitrogen. Hydrogen was then introduced until the theoretical amount was adsorbed. The catalyst was filtered off and the solvent evaporated in vacuo. Ethanolic hydrochloric acid solution (6N) was added, the solvent evaporated and the residue washed with a mixture of diethylether/acetone (10:1) and filtered to give 1-(RS)(+−)-1-amino-2-methylindane hydrochloride (9.7 g, yield 85%), mp. 241-242° C., purity 95%.

c. trans-1-amino-2-methylindane 1-(RS)(+−)-1-Amino-2-methylindane hydrochloride (19.7 g, 0.1073 mol) was mixed with aqueous sodium hydroxide (2N) and extracted with ethyl acetate. The organic layer is dried (sodium sulfate), evaporated and the residue purified by column chromatography, eluting with ethyl acetate/triethylamine (100:1) to give the following compounds:

i) trans-1-amino-2-methylindane (6.6 g), $^1$H-NMR (CDCl$_3$): 1.25 (3H, d), 1.90-2.05 (1H, m), 2.5 (1H, dd), 3.05 (1H, dd), 3.78 (1H, d, 8.1 Hz), 7.1-7.3 (4H, m);

ii) a mixture of trans-1-amino-2-methylindane and cis-1-amino-2-methylindane (2.7 g); and iii) cis-1-amino-2-methylindane (4.0 g), $^1$H-NMR (CDCl$_3$): 0.95 (3H, d), 2.40-2.60 (2H, m), 2.80-2.95 (1H, m), 4.20 (1H, d, 6.2 Hz), 7.1-7.3 (4H, m).

d. N-[(1R,2S)-2-methyl-1-indanyl]-2-methoxyacetamide, and (1S,2R)-1-amino-2-methylindane hydrochloride Novozym 435 (Aldrich Corp., 1.0 g) was added to a mixture of trans-1-amino-2-methylindane (6.6 g, 0.0448) and methyl 2-methoxyacetate (5.04 g 0.0484 mol) in tert-butyl methyl ether. The mixture was heated at reflux for 2 hours, a further amount of Novozym 435 (0.5 g) added and heating is continued for an additional 2 hours. Dichloromethane was added to the cooled mixture and the biocatalyst filtered off. The organic layer was dried (sodium sulfate), evaporated and the residue dissolved in the minimum of dichloromethane. A solution of ethanolic hydrochloric acid (8N) was added and the solid filtered to give (1S,2R)-1-amino-2-methylindane hydrochloride, and the filtrate evaporated to give N-[(1R,2S)-2-methyl-1-indanyl]-2-methoxyacetamide (5.9 g), m.p. 78-79° C.

e. (1R,2S)-1-amino-2-methylindane hydrochloride

Concentrated hydrochloric acid (8 ml) was added to a solution of N-[(1R,2S)-2-methyl-1-indanyl]-2-methoxyacetamide (5.9 g, 0.0269 mol) in ethanol and water, and the mixture heated for 12 hours at reflux. The solvent was evaporated and a small amount of ethyl acetate added. The undissolved solid was filtered off to give (1R,2S)-1-amino-2-methylindane hydrochloride (1.0 g) as a solid, chemical purity>95%.

f. (1R,2S)-1-(bisguanidino)-2-methylindane monohydrochloride

A homogeneous mixture of (1R,2S)-1-amino-2-methylindane hydrochloride (1.0 g, 0.0054 mol) and 1-cyanoguanidine (0.46 g, 0.0054 mol) in 1,3-dichlorobenzene was heated for 150 minutes at 140-150° C. The cooled mixture was diluted with toluene and the solid filtered off to give (1R,2S)-1-(bisguanidino)-2-methylindane monohydrochloride (1.1 g, yield 67.7%) as a solid, mp. 172-178° C., purity 90%.

g. 2-amino-4-[(1R,2S)-2-methyl-1-indanylamino]-6-[(1R)-1-fluoroethyl]-1,3,5-triazine A 30% solution of sodium methoxide (0.39 g, 0.4 ml, 0.0022 mol) in methanol was added to a stirred suspension of (1R,2S)-1-(bisguanidino)-2-methylindane monohydrochloride (0.550 g, 0.0021 mol) in methanol. Then methyl(2R)-2-fluoropropanoate (0.55 g, 0.0051 mol) was added at room temperature, followed by an additional quantity of 30% solution of sodium methoxide (0.59 g, 0.6 ml, 0.0033 mol). After 4 hours at room temperature the mixture was filtered, and the filtrate evaporated. The residue was dissolved in ethyl acetate, washed (water), dried (sodium sulfate) and evaporated. The residue was purified by column chromatography, eluting with a mixture of ethyl acetate:heptane (7:3) as eluent to give 2-amino-4-[(1R,2S)-2-methyl-1-indanylamino]-6-[(1R)-1-fluoroethyl]-1,3,5-triazine (0.09 g, yield 15%, Compound number 2.1), mp. 146-150° C., optical rotation (chloroform, c=1): +104.4°, purity 95.25% (hplc, Chiralcel OD, 250×4.6 mm, eluent n-hexane:2-propanol 90:10, 0.6 ml/min, rt 17.93 min).

The following preferred compounds of formula (I) shown in Tables 1 to 14 also form part of the present invention, and are obtained by, or analogously to, the above Examples A1, A2 and A3 or the above-described general methods.

In the Tables the structure of a compound is represented by the formula of the predominant stereochemical isomer unless defined otherwise specifically (e.g. racemic mixtrure of chiral compounds).

The following abbreviations are used in the Tables 1 to 14:

"Me" means methyl, and "Et" means ethyl, and "Pr" means n-propyl.

"Cpd" means Compound Number. Compound numbers are given for reference purposes only.

After the end of some Tables additional physical data are provided for some of the compounds in the respective Table.

Optical rotation is measured and defined as for the examples A1 to A3 above. $^1$H-NMR spectra were recorded in deuterochloroform unless otherwise stated, with chemical shifts given in ppm. The following notations are used: s=singlet, d=doublet, t=triplet, m=multiplet.

TABLE 1

Compounds of formula (Id-1):

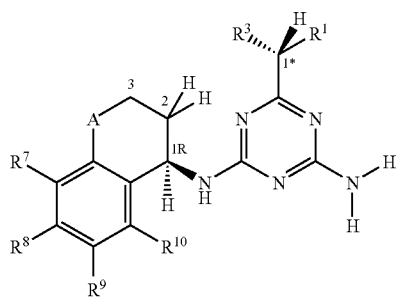

(Id-1)

| Cpd | R$^1$ | R$^3$ | R$^7$ | R$^8$ | R$^9$ | R$^{10}$ | A | Physical data |
|---|---|---|---|---|---|---|---|---|
| 1.1 | Me | F | H | H | H | H | direct bond | white solid |
| 1.2 | Me | F | H | H | Me | H | direct bond | light brown solid |
| 1.3 | Me | F | H | H | F | H | direct bond | white solid |
| 1.4 | Me | F | H | H | Cl | H | direct bond | |
| 1.5 | Me | F | H | H | Br | H | direct bond | |
| 1.6 | Me | F | Me | H | Me | H | direct bond | |
| 1.7 | Me | F | H | Me | Me | H | direct bond | waxy solid |
| 1.8 | Me | F | H | H | Me | Me | direct bond | |
| 1.9 | Me | F | H | F | Me | H | direct bond | |
| 1.10 | Me | F | H | Cl | Cl | H | direct bond | |
| 1.11 | Me | F | H | H | H | H | CH$_2$ | white solid |
| 1.12 | Me | F | H | H | Me | H | CH$_2$ | solid |
| 1.13 | Me | F | H | H | F | H | CH$_2$ | |
| 1.14 | Me | F | H | H | Cl | H | CH$_2$ | |
| 1.15 | Me | F | Me | H | Me | H | CH$_2$ | white solid |
| 1.16 | Me | F | H | Me | Me | H | CH$_2$ | |
| 1.17 | Me | F | H | H | Me | Me | CH$_2$ | |
| 1.18 | Me | F | H | F | Me | H | CH$_2$ | |
| 1.19 | Me | F | H | Cl | Cl | H | CH$_2$ | |
| 1.20 | Me | F | H | H | H | H | O | white solid |
| 1.21 | Me | F | H | H | Me | H | O | solid |
| 1.22 | Me | F | H | H | F | H | O | |
| 1.23 | Me | F | H | H | Cl | H | O | |
| 1.24 | Me | Cl | H | H | H | H | direct bond | white solid |
| 1.25 | Me | Cl | H | H | Me | H | direct bond | |
| 1.26 | Me | Cl | H | H | F | H | direct bond | |
| 1.27 | Me | Cl | H | H | Cl | H | direct bond | |
| 1.28 | Me | Cl | H | H | H | H | CH$_2$ | solid |
| 1.29 | Me | Cl | H | H | Me | H | CH$_2$ | |

TABLE 1-continued

Compounds of formula (Id-1):

(Id-1) structure shown with substituents $R^1$, $R^3$, $R^7$, $R^8$, $R^9$, $R^{10}$, and A.

| Cpd | $R^1$ | $R^3$ | $R^7$ | $R^8$ | $R^9$ | $R^{10}$ | A | Physical data |
|---|---|---|---|---|---|---|---|---|
| 1.30 | Me | Cl | H | H | F | H | CH$_2$ | |
| 1.31 | Me | Cl | H | H | H | H | O | white solid |
| 1.32 | Me | Cl | H | H | Me | H | O | |
| 1.33 | Me | Cl | H | H | F | H | O | |
| 1.34 | Me | Cl | H | H | Cl | H | O | |
| 1.35 | Et | F | H | H | H | H | direct bond | |
| 1.36 | Et | F | H | H | Me | H | direct bond | |
| 1.37 | Et | F | H | H | F | H | direct bond | |
| 1.38 | Et | F | H | H | Cl | H | direct bond | |
| 1.39 | Et | F | H | H | Br | H | direct bond | |
| 1.40 | Et | Cl | H | H | H | H | direct bond | |
| 1.41 | Et | Cl | H | H | Me | H | direct bond | |
| 1.42 | Et | Cl | H | H | F | H | direct bond | |
| 1.43 | Et | Cl | H | H | Cl | H | direct bond | |
| 1.44 | Et | Cl | H | H | Br | H | direct bond | |
| 1.45 | Et | F | H | H | H | H | CH$_2$ | |
| 1.46 | Et | F | H | H | Me | H | CH$_2$ | |
| 1.47 | Et | F | H | H | F | H | CH$_2$ | |
| 1.48 | Et | F | H | H | Cl | H | CH$_2$ | |
| 1.49 | Et | F | H | H | Br | H | CH$_2$ | |
| 1.50 | Et | Cl | H | H | H | H | CH$_2$ | |
| 1.51 | Et | Cl | H | H | Me | H | CH$_2$ | |
| 1.52 | Et | Cl | H | H | F | H | CH$_2$ | |
| 1.53 | Et | Cl | H | H | Cl | H | CH$_2$ | |
| 1.54 | Et | Cl | H | H | Br | H | CH$_2$ | |
| 1.55 | Et | F | H | H | H | H | O | |
| 1.56 | Et | F | H | H | Me | H | O | |
| 1.57 | Et | F | H | H | F | H | O | |
| 1.58 | Et | F | H | H | Cl | H | O | |
| 1.59 | Et | F | H | H | Br | H | O | |
| 1.60 | Et | Cl | H | H | H | H | O | |
| 1.61 | Et | Cl | H | H | Me | H | O | |
| 1.62 | Et | Cl | H | H | F | H | O | |
| 1.63 | Et | Cl | H | H | Cl | H | O | |
| 1.64 | Et | Cl | H | H | Br | H | O | |
| 1.65 | Me | Cl | Me | H | Me | H | CH$_2$ | |
| 1.66 | Me | F | Me | Me | H | H | O | white solid |
| 1.67 | Me | F | F | H | H | H | O | solid |
| 1.68 | Me | F | H | H | Et | H | direct | solid |
| 1.69 | Me | F | H | H | OMe | H | direct | solid |

Notes to physical data in Table 1 (reference is made to the compound no. in Table 1):
Cpd. 1.1: mp 176-178° C., optical rotation +116.7°;
Cpd. 1.2: optical rotation +113.5°;
Cpd. 1.3: optical rotation +112.7°;
Cpd. 1.11: mp 151-154° C., optical rotation +111.1°;
Cpd. 1.12: mp 68-72° C., optical rotation +76.8°;
Cpd. 1.15: mp 163-165° C., optical rotation +70.1°;
Cpd. 1.20: mp 110-112° C., optical rotation +75.4°;
Cpd. 1.21: 127-130° C., optical rotation +52.3°;
Cpd. 1.24: mp 153-155° C., optical rotation +82,5°;
Cpd. 1.28: mp 140-144° C., optical rotation +79.9°;
Cpd. 1.31: mp 99-100° C., optical rotation +69.2°.
Cpd. 1.66: optical rotation +112.7°;
Cpd. 1.67: mp 88-95° C., optical rotation +66.5°;
Cpd. 1.68: mp 145-146° C., optical rotation +79.3°;
Cpd. 1.69: mp 149-150° C., optical rotation +84.0°

TABLE 2

Compounds of formula (If-1):

(If-1) structure shown with substituents $R^1$, $R^3$, $R^6$, $R^7$, $R^8$, $R^9$, $R^{10}$, and A.

| Cpd | $R^1$ | $R^3$ | $R^6$ | $R^7$ | $R^8$ | $R^9$ | $R^{10}$ | A | Physical data |
|---|---|---|---|---|---|---|---|---|---|
| 2.1 | Me | F | Me | H | H | H | H | direct bond | white solid |
| 2.2 | Me | F | Me | H | H | Me | H | direct bond | white foam |
| 2.3 | Me | F | Me | H | H | F | H | direct bond | |
| 2.4 | Me | F | Me | H | H | Cl | H | direct bond | white solid |
| 2.5 | Me | F | Me | H | H | Br | H | direct bond | |
| 2.6 | Me | F | Me | Me | H | Me | H | direct bond | |
| 2.7 | Me | F | Me | H | Me | Me | H | direct bond | |
| 2.8 | Me | F | Me | H | H | Me | Me | direct bond | |
| 2.9 | Me | F | Me | H | F | Me | H | direct bond | |
| 2.10 | Me | F | Me | H | Cl | Cl | H | direct bond | |
| 2.11 | Me | F | Me | H | H | H | H | CH$_2$ | white solid |
| 2.12 | Me | F | Me | H | H | Me | H | CH$_2$ | |
| 2.13 | Me | F | Me | H | H | F | H | CH$_2$ | |
| 2.14 | Me | F | Me | H | H | Cl | H | CH$_2$ | |
| 2.15 | Me | F | Me | Me | H | Me | H | CH$_2$ | |
| 2.16 | Me | F | Me | H | Me | Me | H | CH$_2$ | |
| 2.17 | Me | F | Me | H | H | Me | Me | CH$_2$ | |
| 2.18 | Me | F | Me | H | F | Me | H | CH$_2$ | |
| 2.19 | Me | F | Me | H | Cl | Cl | H | CH$_2$ | |
| 2.20 | Me | F | Me | H | H | H | H | O | |
| 2.21 | Me | F | Me | H | H | Me | H | O | |
| 2.22 | Me | F | Me | H | H | F | H | O | |
| 2.23 | Me | F | Me | H | H | Cl | H | O | |
| 2.24 | Me | Cl | Me | H | H | H | H | direct bond | |
| 2.25 | Me | Cl | Me | H | H | Me | H | direct bond | solid |
| 2.26 | Me | Cl | Me | H | H | F | H | direct bond | |
| 2.27 | Me | Cl | Me | H | H | Cl | H | direct bond | |
| 2.28 | Me | Cl | Me | H | H | Me | H | CH$_2$ | white solid |
| 2.29 | Me | Cl | Me | H | H | H | H | CH$_2$ | |
| 2.30 | Me | Cl | Me | H | H | Me | H | CH$_2$ | |
| 2.31 | Me | Cl | Me | H | H | F | H | CH$_2$ | |
| 2.32 | Me | Cl | Me | H | H | Cl | H | CH$_2$ | |
| 2.33 | Me | Cl | Me | H | H | H | H | O | |
| 2.34 | Me | Cl | Me | H | H | Me | H | O | |
| 2.35 | Me | Cl | Me | H | H | F | H | O | |
| 2.36 | Me | Cl | Me | H | H | Cl | H | O | |
| 2.37 | Et | F | Me | H | H | H | H | direct bond | |
| 2.38 | Et | F | Me | H | H | Me | H | direct bond | |
| 2.39 | Et | F | Me | H | H | F | H | direct bond | |
| 2.40 | Et | F | Me | H | H | Cl | H | direct bond | |
| 2.41 | Et | F | Me | H | H | Br | H | direct bond | |
| 2.42 | Et | Cl | Me | H | H | H | H | direct bond | |
| 2.43 | Et | Cl | Me | H | H | Me | H | direct bond | |
| 2.44 | Et | Cl | Me | H | H | F | H | direct bond | |
| 2.45 | Et | Cl | Me | H | H | Cl | H | direct bond | |
| 2.46 | Et | Cl | Me | H | H | Br | H | direct bond | |
| 2.47 | Et | F | Me | H | H | H | H | CH$_2$ | |
| 2.48 | Et | F | Me | H | H | Me | H | CH$_2$ | |
| 2.49 | Et | F | Me | H | H | F | H | CH$_2$ | |
| 2.50 | Et | F | Me | H | H | Cl | H | CH$_2$ | |
| 2.51 | Et | F | Me | H | H | Br | H | CH$_2$ | |
| 2.52 | Et | Cl | Me | H | H | H | H | CH$_2$ | |
| 2.53 | Et | Cl | Me | H | H | Me | H | CH$_2$ | |
| 2.54 | Et | Cl | Me | H | H | F | H | CH$_2$ | |
| 2.55 | Et | Cl | Me | H | H | Cl | H | CH$_2$ | |
| 2.56 | Et | Cl | Me | H | H | Br | H | CH$_2$ | |
| 2.57 | Et | F | Me | H | H | H | H | O | |
| 2.58 | Et | F | Me | H | H | Me | H | O | |
| 2.59 | Et | F | Me | H | H | F | H | O | |
| 2.60 | Et | F | Me | H | H | Cl | H | O | |

TABLE 2-continued

Compounds of formula (If-1):

(If-1)

| Cpd | R¹ | R³ | R⁶ | R⁷ | R⁸ | R⁹ | R¹⁰ | A | Physical data |
|---|---|---|---|---|---|---|---|---|---|
| 2.61 | Et | F | Me | H | H | Br | H | O | |
| 2.62 | Et | Cl | Me | H | H | H | H | O | |
| 2.63 | Et | Cl | Me | H | H | Me | H | O | |
| 2.64 | Et | Cl | Me | H | H | F | H | O | |
| 2.65 | Et | Cl | Me | H | H | Cl | H | O | |
| 2.66 | Et | Cl | Me | H | H | Br | H | O | |
| 2.67 | Me | F | Me | Me | Me | H | H | O | |
| 2.68 | Me | F | Me | F | H | H | H | O | |
| 2.69 | Me | F | Me | H | H | Et | H | direct | |
| 2.70 | Me | F | Me | H | H | OMe | H | direct | |

Notes to physical data in Table 2 (reference is made to the compound no. in Table 2):
Cpd. 2.1: mp 146-150° C., optical rotation +104°;
Cpd. 2.11: optical rotation +168.9°;
Cpd. 2.25: mp 68-70° C., optical rotation +140.9°.
Cpd. 2.28: mp 127-128° C., optical rotation +49.6°.

TABLE 3

Compounds of formula (Ie-1):

(Ie-1)

| Cpd | R¹ | R³ | R⁷ | R⁸ | R⁹ | R¹⁰ | A | Physical data |
|---|---|---|---|---|---|---|---|---|
| 3.1 | Me | F | H | H | H | H | direct bond | white solid |
| 3.2 | Me | F | H | H | Me | H | direct bond | white solid |
| 3.3 | Me | F | H | H | F | H | direct bond | |
| 3.4 | Me | F | H | H | Cl | H | direct bond | |
| 3.5 | Me | F | H | H | Br | H | direct bond | |
| 3.6 | Me | F | Me | H | Me | H | direct bond | |
| 3.7 | Me | F | H | Me | Me | H | direct bond | Waxy solid |
| 3.8 | Me | F | H | H | Me | Me | direct bond | |
| 3.9 | Me | F | H | F | Me | H | direct bond | |
| 3.10 | Me | F | H | Cl | Cl | H | direct bond | |
| 3.11 | Me | F | H | H | H | H | CH₂ | white solid |
| 3.12 | Me | F | H | H | Me | H | CH₂ | |
| 3.13 | Me | F | H | H | F | H | CH₂ | |
| 3.14 | Me | F | H | H | Cl | H | CH₂ | |
| 3.15 | Me | F | Me | H | Me | H | CH₂ | white solid |
| 3.16 | Me | F | H | Me | Me | H | CH₂ | |
| 3.17 | Me | F | H | H | Me | Me | CH₂ | |
| 3.18 | Me | F | H | F | Me | H | CH₂ | |
| 3.19 | Me | F | H | Cl | Cl | H | CH₂ | |
| 3.20 | Me | F | H | H | H | H | O | white solid |
| 3.21 | Me | F | H | H | Me | H | O | |
| 3.22 | Me | F | H | H | F | H | O | |
| 3.23 | Me | F | H | H | Cl | H | O | |
| 3.24 | Me | Cl | H | H | H | H | direct bond | white solid |
| 3.25 | Me | Cl | H | H | Me | H | direct bond | |
| 3.26 | Me | Cl | H | H | F | H | direct bond | |
| 3.27 | Me | Cl | H | H | Cl | H | direct bond | |
| 3.28 | Me | Cl | H | H | H | H | CH₂ | |
| 3.29 | Me | Cl | H | H | Me | H | CH₂ | |
| 3.30 | Me | Cl | H | H | F | H | CH₂ | |
| 3.31 | Me | Cl | Me | H | Me | H | CH₂ | |
| 3.32 | Me | Cl | H | H | H | H | O | |
| 3.33 | Me | Cl | H | H | Me | H | O | |
| 3.34 | Me | Cl | H | H | F | H | O | |
| 3.35 | Me | Cl | H | H | Cl | H | O | |
| 3.36 | Et | F | H | H | H | H | direct bond | |
| 3.37 | Et | F | H | H | Me | H | direct bond | |
| 3.38 | Et | F | H | H | F | H | direct bond | |
| 3.39 | Et | F | H | H | Cl | H | direct bond | |
| 3.40 | Et | F | H | H | Br | H | direct bond | |
| 3.41 | Et | Cl | H | H | H | H | direct bond | |
| 3.42 | Et | Cl | H | H | Me | H | direct bond | |
| 3.43 | Et | Cl | H | H | F | H | direct bond | |
| 3.44 | Et | Cl | H | H | Cl | H | direct bond | |
| 3.45 | Et | Cl | H | H | Br | H | direct bond | |
| 3.46 | Et | F | H | H | H | H | CH₂ | |
| 3.47 | Et | F | H | H | Me | H | CH₂ | |
| 3.48 | Et | F | H | H | F | H | CH₂ | |
| 3.49 | Et | F | H | H | Cl | H | CH₂ | |
| 3.50 | Et | F | H | H | Br | H | CH₂ | |
| 3.51 | Et | Cl | H | H | H | H | CH₂ | |
| 3.52 | Et | Cl | H | H | Me | H | CH₂ | |
| 3.53 | Et | Cl | H | H | F | H | CH₂ | |
| 3.54 | Et | Cl | H | H | Cl | H | CH₂ | |
| 3.55 | Et | Cl | H | H | Br | H | CH₂ | |
| 3.56 | Et | F | H | H | H | H | O | |
| 3.57 | Et | F | H | H | Me | H | O | |
| 3.58 | Et | F | H | H | F | H | O | |
| 3.59 | Et | F | H | H | Cl | H | O | |
| 3.60 | Et | F | H | H | Br | H | O | |
| 3.61 | Et | Cl | H | H | H | H | O | |
| 3.62 | Et | Cl | H | H | Me | H | O | |
| 3.63 | Et | Cl | H | H | F | H | O | |
| 3.64 | Et | Cl | H | H | Cl | H | O | |
| 3.65 | Et | Cl | H | H | Br | H | O | |

Notes to physical data in Table 3 (reference is made to the compound no. in Table 3):
Cpd 3.1: mp 149-150° C., optical rotation +74.4°;
Cpd 3.2: optical rotation +113.5°;
Cpd 3.11: mp 147-149° C., optical rotation +84.4°;
Cpd 3.15: mp 167-171° C., optical rotation +36.5°;
Cpd 3.20: mp 183-185° C., optical rotation +54.5°;
Cpd 3.24: mp 151-152° C., optical rotation +71.8°.

TABLE 4

Compounds of formula (Ig-1):

(Ig-1)

| Cpd | R¹ | R³ | R⁶ | R⁷ | R⁸ | R⁹ | R¹⁰ | A | Physical data |
|---|---|---|---|---|---|---|---|---|---|
| 4.1 | Me | F | Me | H | H | H | H | direct bond | white solid |
| 4.2 | Me | F | Me | H | H | Me | H | direct bond | white foam |
| 4.3 | Me | F | Me | H | H | F | H | direct bond | |
| 4.4 | Me | F | Me | H | H | Cl | H | direct bond | |
| 4.5 | Me | F | Me | H | H | Br | H | direct bond | |
| 4.6 | Me | F | Me | Me | H | Me | H | direct bond | |
| 4.7 | Me | F | Me | H | Me | Me | H | direct bond | |
| 4.8 | Me | F | Me | H | H | Me | Me | direct bond | |
| 4.9 | Me | F | Me | H | F | Me | H | direct bond | |
| 4.10 | Me | F | Me | H | Cl | Cl | H | direct bond | |
| 4.11 | Me | F | Me | H | H | H | H | CH₂ | |
| 4.12 | Me | F | Me | H | H | Me | H | CH₂ | |
| 4.13 | Me | F | Me | H | H | F | H | CH₂ | |
| 4.14 | Me | F | Me | H | H | Cl | H | CH₂ | |
| 4.15 | Me | F | Me | Me | H | Me | H | CH₂ | |
| 4.16 | Me | F | Me | H | Me | Me | H | CH₂ | |
| 4.17 | Me | F | Me | H | H | Me | Me | CH₂ | |
| 4.18 | Me | F | Me | H | F | Me | H | CH₂ | |
| 4.19 | Me | F | Me | H | Cl | Cl | H | CH₂ | |
| 4.20 | Me | F | Me | H | H | H | H | O | |
| 4.21 | Me | F | Me | H | H | Me | H | O | |
| 4.22 | Me | F | Me | H | H | F | H | O | |
| 4.23 | Me | F | Me | H | H | Cl | H | O | |
| 4.24 | Me | Cl | Me | H | H | H | H | direct bond | |
| 4.25 | Me | Cl | Me | H | H | Me | H | direct bond | |
| 4.26 | Me | Cl | Me | H | H | F | H | direct bond | |
| 4.27 | Me | Cl | Me | H | H | Cl | H | direct bond | |
| 4.28 | Me | Cl | Me | H | H | H | H | CH₂ | |
| 4.29 | Me | Cl | Me | H | H | Me | H | CH₂ | |
| 4.30 | Me | Cl | Me | H | H | F | H | CH₂ | |
| 4.31 | Me | Cl | Me | H | H | Cl | H | CH₂ | |
| 4.32 | Me | Cl | Me | H | H | H | H | O | |
| 4.33 | Me | Cl | Me | H | H | Me | H | O | |
| 4.34 | Me | Cl | Me | H | H | F | H | O | |
| 4.35 | Me | Cl | Me | H | H | Cl | H | O | |
| 4.36 | Et | F | Me | H | H | H | H | direct bond | |
| 4.37 | Et | F | Me | H | H | Me | H | direct bond | |
| 4.38 | Et | F | Me | H | H | F | H | direct bond | |
| 4.39 | Et | F | Me | H | H | Cl | H | direct bond | |
| 4.40 | Et | F | Me | H | H | Br | H | direct bond | |
| 4.41 | Et | Cl | Me | H | H | H | H | direct bond | |
| 4.42 | Et | Cl | Me | H | H | Me | H | direct bond | |
| 4.43 | Et | Cl | Me | H | H | F | H | direct bond | |
| 4.44 | Et | Cl | Me | H | H | Cl | H | direct bond | |
| 4.45 | Et | Cl | Me | H | H | Br | H | direct bond | |
| 4.46 | Et | F | Me | H | H | H | H | CH₂ | |
| 4.47 | Et | F | Me | H | H | Me | H | CH₂ | |
| 4.48 | Et | F | Me | H | H | F | H | CH₂ | |
| 4.49 | Et | F | Me | H | H | Cl | H | CH₂ | |
| 4.50 | Et | F | Me | H | H | Br | H | CH₂ | |
| 4.51 | Et | Cl | Me | H | H | H | H | CH₂ | |
| 4.52 | Et | Cl | Me | H | H | Me | H | CH₂ | |
| 4.53 | Et | Cl | Me | H | H | F | H | CH₂ | |
| 4.54 | Et | Cl | Me | H | H | Cl | H | CH₂ | |
| 4.55 | Et | Cl | Me | H | H | Br | H | CH₂ | |
| 4.56 | Et | F | Me | H | H | H | H | O | |
| 4.57 | Et | F | Me | H | H | Me | H | O | |
| 4.58 | Et | F | Me | H | H | F | H | O | |
| 4.59 | Et | F | Me | H | H | Cl | H | O | |
| 4.60 | Et | F | Me | H | H | Br | H | O | |
| 4.61 | Et | Cl | Me | H | H | H | H | O | |
| 4.62 | Et | Cl | Me | H | H | Me | H | O | |
| 4.63 | Et | Cl | Me | H | H | F | H | O | |
| 4.64 | Et | Cl | Me | H | H | Cl | H | O | |
| 4.65 | Et | Cl | Me | H | H | Br | H | O | |

Notes to physical data in Table 4 (reference is made to the compound no. in Table 4):
Cpd. 4.1: mp 146-150° C., optical rotation +77.9°.

TABLE 5

Compounds of formula (Ih-1):

(Ih-1)

| Cpd | R¹ | R³ | R⁶ | R⁷ | R⁸ | R⁹ | R¹⁰ | A | Physical data |
|---|---|---|---|---|---|---|---|---|---|
| 5.1 | Me | F | Me | H | H | H | H | direct bond | waxy |
| 5.2 | Me | F | Me | H | H | Me | H | direct bond | yellow syrup |
| 5.3 | Me | F | Me | H | H | F | H | direct bond | |
| 5.4 | Me | F | Me | H | H | Cl | H | direct bond | |
| 5.5 | Me | F | Me | H | H | Br | H | direct bond | |
| 5.6 | Me | F | Me | Me | H | Me | H | direct bond | |
| 5.7 | Me | F | Me | H | Me | Me | H | direct bond | |
| 5.8 | Me | F | Me | H | H | Me | Me | direct bond | |
| 5.9 | Me | F | Me | H | F | Me | H | direct bond | |
| 5.10 | Me | F | Me | H | Cl | Cl | H | direct bond | |
| 5.11 | Me | F | Me | H | H | H | H | CH₂ | |
| 5.12 | Me | F | Me | H | H | Me | H | CH₂ | |
| 5.13 | Me | F | Me | H | H | F | H | CH₂ | |
| 5.14 | Me | F | Me | H | H | Cl | H | CH₂ | |
| 5.15 | Me | F | Me | Me | H | Me | H | CH₂ | |
| 5.16 | Me | F | Me | H | Me | Me | H | CH₂ | |
| 5.17 | Me | F | Me | H | H | Me | Me | CH₂ | |
| 5.18 | Me | F | Me | H | F | Me | H | CH₂ | |
| 5.19 | Me | F | Me | H | Cl | Cl | H | CH₂ | |
| 5.20 | Me | F | Me | H | H | H | H | O | |
| 5.21 | Me | F | Me | H | H | Me | H | O | |
| 5.22 | Me | F | Me | H | H | F | H | O | |
| 5.23 | Me | F | Me | H | H | Cl | H | O | |
| 5.24 | Me | Cl | Me | H | H | H | H | direct bond | |
| 5.25 | Me | Cl | Me | H | H | Me | H | direct bond | |
| 5.26 | Me | Cl | Me | H | H | F | H | direct bond | |
| 5.27 | Me | Cl | Me | H | H | Cl | H | direct bond | |
| 5.28 | Me | Cl | Me | H | H | H | H | CH₂ | |

TABLE 5-continued

Compounds of formula (Ih-1):

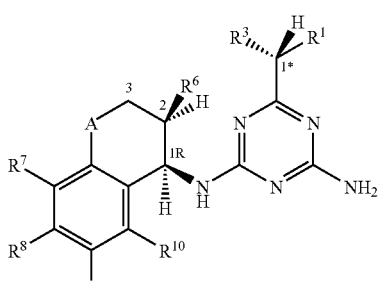

(Ih-1)

| Cpd | R¹ | R³ | R⁶ | R⁷ | R⁸ | R⁹ | R¹⁰ | A | Physical data |
|---|---|---|---|---|---|---|---|---|---|
| 5.29 | Me | Cl | Me | H | H | Me | H | CH₂ | |
| 5.30 | Me | Cl | Me | H | H | F | H | CH₂ | |
| 5.31 | Me | Cl | Me | H | H | Cl | H | CH₂ | |
| 5.32 | Me | Cl | Me | H | H | H | H | O | |
| 5.33 | Me | Cl | Me | H | H | Me | H | O | |
| 5.34 | Me | Cl | Me | H | H | F | H | O | |
| 5.35 | Me | Cl | Me | H | H | Cl | H | O | |
| 5.36 | Et | F | Me | H | H | H | H | direct bond | |
| 5.37 | Et | F | Me | H | H | Me | H | direct bond | |
| 5.38 | Et | F | Me | H | H | F | H | direct bond | |
| 5.39 | Et | F | Me | H | H | Cl | H | direct bond | |
| 5.40 | Et | F | Me | H | H | Br | H | direct bond | |
| 5.41 | Et | Cl | Me | H | H | H | H | direct bond | |
| 5.42 | Et | Cl | Me | H | H | Me | H | direct bond | |
| 5.43 | Et | Cl | Me | H | H | F | H | direct bond | |
| 5.44 | Et | Cl | Me | H | H | Cl | H | direct bond | |
| 5.45 | Et | Cl | Me | H | H | Br | H | direct bond | |
| 5.46 | Et | F | Me | H | H | H | H | CH₂ | |
| 5.47 | Et | F | Me | H | H | Me | H | CH₂ | |
| 5.48 | Et | F | Me | H | H | F | H | CH₂ | |
| 5.49 | Et | F | Me | H | H | Cl | H | CH₂ | |
| 5.50 | Et | F | Me | H | H | Br | H | CH₂ | |
| 5.51 | Et | Cl | Me | H | H | H | H | CH₂ | |
| 5.52 | Et | Cl | Me | H | H | Me | H | CH₂ | |
| 5.53 | Et | Cl | Me | H | H | F | H | CH₂ | |
| 5.54 | Et | Cl | Me | H | H | Cl | H | CH₂ | |
| 5.55 | Et | Cl | Me | H | H | Br | H | CH₂ | |
| 5.56 | Et | F | Me | H | H | H | H | O | |
| 5.57 | Et | F | Me | H | H | Me | H | O | |
| 5.58 | Et | F | Me | H | H | F | H | O | |
| 5.59 | Et | F | Me | H | H | Cl | H | O | |
| 5.60 | Et | F | Me | H | H | Br | H | O | |
| 5.61 | Et | Cl | Me | H | H | H | H | O | |
| 5.62 | Et | Cl | Me | H | H | Me | H | O | |
| 5.63 | Et | Cl | Me | H | H | F | H | O | |
| 5.64 | Et | Cl | Me | H | H | Cl | H | O | |
| 5.65 | Et | Cl | Me | H | H | Br | H | O | |

TABLE 6

Compounds of formula (Ii-1):

(Ii-1)

| Cpd | R¹ | R³ | R⁶ | R⁷ | R⁸ | R⁹ | R¹⁰ | A | Physical data |
|---|---|---|---|---|---|---|---|---|---|
| 6.1 | Me | F | Me | H | H | H | H | direct bond | wax |
| 6.2 | Me | F | Me | H | H | Me | H | direct bond | colourless syrup |
| 6.3 | Me | F | Me | H | H | F | H | direct bond | |
| 6.4 | Me | F | Me | H | H | Cl | H | direct bond | |
| 6.5 | Me | F | Me | H | H | Br | H | direct bond | |
| 6.6 | Me | F | Me | Me | H | Me | H | direct bond | |
| 6.7 | Me | F | Me | H | Me | Me | H | direct bond | |
| 6.8 | Me | F | Me | H | H | Me | Me | direct bond | |
| 6.9 | Me | F | Me | H | F | Me | H | direct bond | |
| 6.10 | Me | F | Me | H | Cl | Cl | H | direct bond | |
| 6.11 | Me | F | Me | H | H | H | H | CH₂ | |
| 6.12 | Me | F | Me | H | H | Me | H | CH₂ | |
| 6.13 | Me | F | Me | H | H | F | H | CH₂ | |
| 6.14 | Me | F | Me | H | H | Cl | H | CH₂ | |
| 6.15 | Me | F | Me | Me | H | Me | H | CH₂ | |
| 6.16 | Me | F | Me | H | Me | Me | H | CH₂ | |
| 6.17 | Me | F | Me | H | H | Me | Me | CH₂ | |
| 6.18 | Me | F | Me | H | F | Me | H | CH₂ | |
| 6.19 | Me | F | Me | H | Cl | Cl | H | CH₂ | |
| 6.20 | Me | F | Me | H | H | H | H | O | |
| 6.21 | Me | F | Me | H | H | Me | H | O | |
| 6.22 | Me | F | Me | H | H | F | H | O | |
| 6.23 | Me | F | Me | H | H | Cl | H | O | |
| 6.24 | Me | Cl | Me | H | H | H | H | direct bond | |
| 6.25 | Me | Cl | Me | H | H | Me | H | direct bond | |
| 6.26 | Me | Cl | Me | H | H | F | H | direct bond | |
| 6.27 | Me | Cl | Me | H | H | Cl | H | direct bond | |
| 6.28 | Me | Cl | Me | H | H | H | H | CH₂ | |
| 6.29 | Me | Cl | Me | H | H | Me | H | CH₂ | |
| 6.30 | Me | Cl | Me | H | H | F | H | CH₂ | |
| 6.31 | Me | Cl | Me | H | H | Cl | H | CH₂ | |
| 6.32 | Me | Cl | Me | H | H | H | H | O | |
| 6.33 | Me | Cl | Me | H | H | Me | H | O | |
| 6.34 | Me | Cl | Me | H | H | F | H | O | |
| 6.35 | Me | Cl | Me | H | H | Cl | H | O | |
| 6.36 | Et | F | Me | H | H | H | H | direct bond | |
| 6.37 | Et | F | Me | H | H | Me | H | direct bond | |
| 6.38 | Et | F | Me | H | H | F | H | direct bond | |
| 6.39 | Et | F | Me | H | H | Cl | H | direct bond | |
| 6.40 | Et | F | Me | H | H | Br | H | direct bond | |
| 6.41 | Et | Cl | Me | H | H | H | H | direct bond | |
| 6.42 | Et | Cl | Me | H | H | Me | H | direct bond | |
| 6.43 | Et | Cl | Me | H | H | F | H | direct bond | |
| 6.44 | Et | Cl | Me | H | H | Cl | H | direct bond | |
| 6.45 | Et | Cl | Me | H | H | Br | H | direct bond | |
| 6.46 | Et | F | Me | H | H | H | H | CH₂ | |
| 6.47 | Et | F | Me | H | H | Me | H | CH₂ | |
| 6.48 | Et | F | Me | H | H | F | H | CH₂ | |
| 6.49 | Et | F | Me | H | H | Cl | H | CH₂ | |
| 6.50 | Et | F | Me | H | H | Br | H | CH₂ | |
| 6.51 | Et | Cl | Me | H | H | H | H | CH₂ | |
| 6.52 | Et | Cl | Me | H | H | Me | H | CH₂ | |
| 6.53 | Et | Cl | Me | H | H | F | H | CH₂ | |
| 6.54 | Et | Cl | Me | H | H | Cl | H | CH₂ | |
| 6.55 | Et | Cl | Me | H | H | Br | H | CH₂ | |
| 6.56 | Et | F | Me | H | H | H | H | O | |
| 6.57 | Et | F | Me | H | H | Me | H | O | |
| 6.58 | Et | F | Me | H | H | F | H | O | |
| 6.59 | Et | F | Me | H | H | Cl | H | O | |

TABLE 6-continued

Compounds of formula (Ii-1):

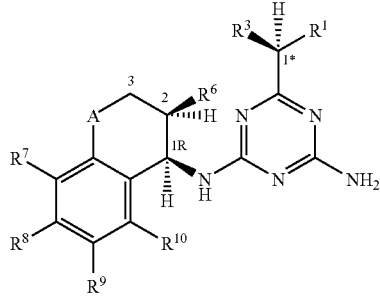

(Ii-1)

| Cpd | R¹ | R³ | R⁶ | R⁷ | R⁸ | R⁹ | R¹⁰ | A | Physical data |
|---|---|---|---|---|---|---|---|---|---|
| 6.60 | Et | F | Me | H | H | Br | H | O | |
| 6.61 | Et | Cl | Me | H | H | H | H | O | |
| 6.62 | Et | Cl | Me | H | H | Me | H | O | |
| 6.63 | Et | Cl | Me | H | H | F | H | O | |
| 6.64 | Et | Cl | Me | H | H | Cl | H | O | |
| 6.65 | Et | Cl | Me | H | H | Br | H | O | |

TABLE 7

Compounds of formula (Ij-1):

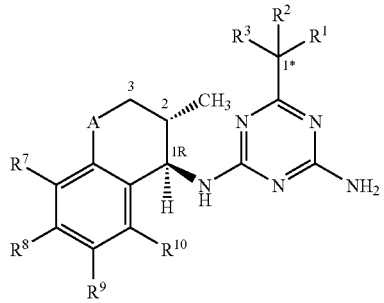

(Ij-1)

[In the compounds of formula (Ij-1) the marked 1* carbon atom is achiral]

| Cpd | R¹ | R² | R³ | R⁷ | R⁸ | R⁹ | R¹⁰ | A | Physical data |
|---|---|---|---|---|---|---|---|---|---|
| 7.1 | H | H | H | H | H | H | H | direct bond | white solid |
| 7.2 | H | H | H | H | H | Me | H | direct bond | solid |
| 7.3 | H | H | H | H | H | F | H | direct bond | waxy |
| 7.4 | H | H | H | H | H | Cl | H | direct bond | waxy |
| 7.5 | H | H | H | H | H | Br | H | direct bond | |
| 7.6 | H | H | H | H | Me | Me | H | direct bond | |
| 7.7 | H | H | H | H | Me | Me | H | direct bond | |
| 7.8 | H | H | H | H | H | Me | Me | direct bond | |
| 7.9 | H | H | H | H | F | Me | H | direct bond | |
| 7.10 | H | H | H | H | Cl | Cl | H | direct bond | |
| 7.11 | H | H | H | H | H | H | H | CH₂ | white solid |
| 7.12 | H | H | H | H | H | Me | H | CH₂ | |
| 7.13 | H | H | H | H | H | F | H | CH₂ | |
| 7.14 | H | H | H | H | H | Cl | H | CH₂ | |
| 7.15 | H | H | H | H | Me | Me | H | CH₂ | |
| 7.16 | H | H | H | H | Me | Me | H | CH₂ | |
| 7.17 | H | H | H | H | H | Me | Me | CH₂ | |
| 7.18 | H | H | H | H | F | Me | H | CH₂ | |
| 7.19 | H | H | H | H | Cl | Cl | H | CH₂ | |
| 7.20 | H | H | H | H | H | H | H | O | |
| 7.21 | H | H | H | H | H | Me | H | O | |
| 7.22 | H | H | H | H | H | F | H | O | |
| 7.23 | H | H | H | H | H | Cl | H | O | |
| 7.24 | Me | Me | H | H | H | H | H | direct bond | white |

TABLE 7-continued

Compounds of formula (Ij-1):

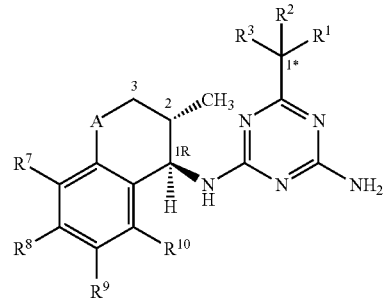

(Ij-1)

[In the compounds of formula (Ij-1) the marked 1* carbon atom is achiral]

| Cpd | R¹ | R² | R³ | R⁷ | R⁸ | R⁹ | R¹⁰ | A | Physical data |
|---|---|---|---|---|---|---|---|---|---|
| | | | | | | | | | solid |
| 7.25 | Me | Me | H | H | H | Me | H | direct bond | |
| 7.26 | Me | Me | H | H | H | F | H | direct bond | |
| 7.27 | Me | Me | H | H | H | Cl | H | direct bond | |
| 7.28 | Me | H | H | H | H | Br | H | direct bond | |
| 7.29 | Me | H | H | H | Me | H | Me | H | direct bond | |
| 7.30 | Me | H | H | H | Me | Me | H | direct bond | |
| 7.31 | Me | H | H | H | H | Me | Me | direct bond | |
| 7.32 | Me | H | H | H | F | Me | H | direct bond | |
| 7.33 | Me | H | H | H | Cl | Cl | H | direct bond | |
| 7.34 | Me | Me | H | H | H | H | H | CH₂ | |
| 7.35 | Me | Me | H | H | H | Me | H | CH₂ | |
| 7.36 | Me | Me | H | H | H | F | H | CH₂ | |
| 7.37 | Me | Me | H | H | H | Cl | H | CH₂ | |
| 7.38 | Me | H | H | Me | H | Me | H | CH₂ | |
| 7.39 | Me | H | H | H | Me | Me | H | CH₂ | |
| 7.40 | Me | H | H | H | H | Me | Me | CH₂ | |
| 7.41 | Me | H | H | H | F | Me | H | CH₂ | |
| 7.42 | Me | H | H | H | Cl | Cl | H | CH₂ | |
| 7.43 | Me | Me | H | H | H | H | H | O | |
| 7.44 | Me | Me | H | H | H | Me | H | O | |
| 7.45 | Me | Me | H | H | H | F | H | O | |
| 7.46 | Me | Me | H | H | H | Cl | H | O | |
| 7.47 | Et | H | H | H | H | H | H | direct bond | white solid |
| 7.48 | Et | H | H | H | H | Me | H | direct bond | white solid |
| 7.49 | Et | H | H | H | H | F | H | direct bond | |
| 7.50 | Et | H | H | H | H | Cl | H | direct bond | |
| 7.51 | Et | H | H | H | H | Br | H | direct bond | |
| 7.52 | Et | H | H | H | Me | H | Me | H | direct bond | |
| 7.53 | Et | H | H | H | Me | Me | H | direct bond | |
| 7.54 | Et | H | H | H | H | Me | Me | direct bond | |
| 7.55 | Et | H | H | H | F | Me | H | direct bond | |
| 7.56 | Et | H | H | H | Cl | Cl | H | direct bond | |
| 7.57 | Et | H | H | H | H | H | H | CH₂ | white solid |
| 7.58 | Et | H | H | H | H | Me | H | CH₂ | |
| 7.59 | Et | H | H | H | H | F | H | CH₂ | |
| 7.60 | Et | H | H | H | H | Cl | H | CH₂ | |
| 7.61 | Et | H | H | Me | H | Me | H | CH₂ | |
| 7.62 | Et | H | H | H | Me | Me | H | CH₂ | |
| 7.63 | Et | H | H | H | H | Me | Me | CH₂ | |
| 7.64 | Et | H | H | H | F | Me | H | CH₂ | |
| 7.65 | Et | H | H | H | Cl | Cl | H | CH₂ | |
| 7.66 | Et | H | H | H | H | H | H | O | |
| 7.67 | Et | H | H | H | H | Me | H | O | |
| 7.68 | Et | H | H | H | H | F | H | O | |
| 7.69 | Et | H | H | H | H | Cl | H | O | |
| 7.70 | OMe | H | H | H | H | H | H | direct bond | white solid |
| 7.71 | OMe | H | H | H | H | H | H | CH₂ | |
| 7.72 | OMe | H | H | H | H | Me | H | direct bond | solid |
| 7.73 | OMe | H | H | H | H | Me | H | CH₂ | |
| 7.74 | Me | H | H | H | H | H | H | direct bond | white solid |
| 7.75 | Me | H | H | H | H | Me | H | direct bond | white |

TABLE 7-continued

Compounds of formula (Ij-1):

(Ij-1)

[In the compounds of formula (Ij-1) the marked 1* carbon atom is achiral]

| Cpd | R¹ | R² | R³ | R⁷ | R⁸ | R⁹ | R¹⁰ | A | Physical data |
|---|---|---|---|---|---|---|---|---|---|
| 7.76 | Me | H | H | H | H | F | H | direct bond | solid |
| 7.77 | Me | H | H | H | H | Cl | H | direct bond | |
| 7.78 | Me | H | H | H | H | H | H | CH₂ | white solid |
| 7.79 | Me | H | H | H | H | Me | H | CH₂ | |
| 7.80 | Me | H | H | H | H | F | H | CH₂ | |
| 7.81 | Me | H | H | H | H | Cl | H | CH₂ | |
| 7.82 | Me | H | H | H | H | H | H | O | |
| 7.83 | Me | H | H | H | H | Me | H | O | |
| 7.84 | Me | H | H | H | H | F | H | O | |
| 7.85 | Me | H | H | H | H | Cl | H | O | |
| 7.86 | Cl | Me | Cl | H | H | H | H | direct bond | |
| 7.87 | Cl | Me | Cl | H | H | Me | H | direct bond | |
| 7.88 | Cl | Me | Cl | H | H | F | H | direct bond | |
| 7.89 | Cl | Me | Cl | H | H | Cl | H | direct bond | |
| 7.90 | Cl | Me | Cl | H | H | H | H | CH₂ | |
| 7.91 | Cl | Me | Cl | H | H | Me | H | CH₂ | |
| 7.92 | Cl | Me | Cl | H | H | F | H | CH₂ | |
| 7.93 | Cl | Me | Cl | H | H | Cl | H | CH₂ | |
| 7.94 | Cl | Me | Cl | H | H | H | H | O | |
| 7.95 | Cl | Me | Cl | H | H | Me | H | O | |
| 7.96 | Cl | Me | Cl | H | H | F | H | O | |
| 7.97 | Cl | Me | Cl | H | H | Cl | H | O | |
| 7.98 | H | H | F | H | H | H | H | direct bond | |
| 7.99 | H | H | F | H | H | Me | H | direct bond | |
| 7.100 | H | H | F | H | H | F | H | direct bond | |
| 7.101 | H | H | F | H | H | Cl | H | direct bond | |
| 7.102 | H | H | F | H | H | Br | H | direct bond | |
| 7.103 | H | H | F | Me | H | Me | H | direct bond | |
| 7.104 | H | H | F | H | Me | Me | H | direct bond | |
| 7.105 | H | H | F | H | H | Me | Me | direct bond | |
| 7.106 | H | H | F | H | F | Me | H | direct bond | |
| 7.107 | H | H | F | H | Cl | Cl | H | direct bond | |
| 7.108 | H | H | F | H | H | H | H | CH₂ | |
| 7.109 | H | H | F | H | H | Me | H | CH₂ | |
| 7.110 | H | H | F | H | H | F | H | CH₂ | |
| 7.111 | H | H | F | H | H | Cl | H | CH₂ | |
| 7.112 | H | H | F | Me | H | Me | H | CH₂ | |
| 7.113 | H | H | F | H | Me | Me | H | CH₂ | |
| 7.114 | H | H | F | H | H | Me | Me | CH₂ | |
| 7.115 | H | H | F | H | F | Me | H | CH₂ | |
| 7.116 | H | H | F | H | Cl | Cl | H | CH₂ | |
| 7.117 | H | H | F | H | H | H | H | O | |
| 7.118 | H | H | F | H | H | Me | H | O | |
| 7.119 | H | H | F | H | H | F | H | O | |
| 7.120 | H | H | F | H | H | Cl | H | O | |
| 7.121 | H | H | Cl | H | H | H | H | direct bond | |
| 7.122 | H | H | Cl | H | H | Me | H | direct bond | |
| 7.123 | H | H | Cl | H | H | F | H | direct bond | |
| 7.124 | H | H | Cl | H | H | Cl | H | direct bond | |
| 7.125 | H | H | Cl | H | H | H | H | CH₂ | |
| 7.126 | H | H | Cl | H | H | Me | H | CH₂ | |
| 7.127 | H | H | Cl | H | H | F | H | CH₂ | |
| 7.128 | H | H | Cl | H | H | Cl | H | CH₂ | |
| 7.129 | H | H | Cl | H | H | H | H | O | |
| 7.130 | H | H | Cl | H | H | Me | H | O | |
| 7.131 | H | H | Cl | H | H | F | H | O | |
| 7.132 | H | H | Cl | H | H | Cl | H | O | |
| 7.133 | cyclopropyl | | | H | H | H | H | direct bond | |
| 7.134 | cyclopropyl | | | H | H | Me | H | direct bond | |
| 7.135 | cyclopropyl | | | H | H | F | H | direct bond | |
| 7.136 | cyclopropyl | | | H | H | Cl | H | direct bond | |
| 7.137 | cyclopropyl | | | H | H | Br | H | direct bond | |
| 7.138 | cyclopropyl | | | Me | H | Me | H | direct bond | |
| 7.139 | cyclopropyl | | | H | Me | Me | H | direct bond | |
| 7.140 | cyclopropyl | | | H | H | Me | Me | direct bond | |
| 7.141 | cyclopropyl | | | H | F | Me | H | direct bond | |
| 7.142 | cyclopropyl | | | H | Cl | Cl | H | direct bond | |
| 7.143 | cyclopropyl | | | H | H | H | H | CH₂ | |
| 7.144 | cyclopropyl | | | H | H | Me | H | CH₂ | |
| 7.145 | cyclopropyl | | | H | H | F | H | CH₂ | |
| 7.146 | cyclopropyl | | | H | H | Cl | H | CH₂ | |
| 7.147 | cyclopropyl | | | Me | H | Me | H | CH₂ | |
| 7.148 | cyclopropyl | | | H | Me | Me | H | CH₂ | |
| 7.149 | cyclopropyl | | | H | H | Me | Me | CH₂ | |
| 7.150 | cyclopropyl | | | H | F | Me | H | CH₂ | |
| 7.151 | cyclopropyl | | | H | Cl | Cl | H | CH₂ | |
| 7.152 | cyclopropyl | | | H | H | H | H | O | |
| 7.153 | cyclopropyl | | | H | H | Me | H | O | |
| 7.154 | cyclopropyl | | | H | H | F | H | O | |
| 7.155 | cyclopropyl | | | H | H | Cl | H | O | |
| 7.156 | cyclopropyl | Me | H | H | H | H | H | direct bond | |
| 7.157 | cyclopropyl | Me | H | H | H | Me | H | direct bond | |
| 7.158 | cyclopropyl | Me | H | H | H | F | H | direct bond | |
| 7.159 | cyclopropyl | Me | H | H | H | Cl | H | direct bond | |
| 7.160 | cyclopropyl | Me | H | H | H | H | H | CH₂ | |
| 7.161 | cyclopropyl | Me | H | H | H | Me | H | CH₂ | |
| 7.162 | cyclopropyl | Me | H | H | H | F | H | CH₂ | |
| 7.163 | cyclopropyl | Me | H | H | H | Cl | H | CH₂ | |
| 7.164 | cyclopropyl | Me | H | H | H | H | H | O | |
| 7.165 | cyclopropyl | Me | H | H | H | Me | H | O | |
| 7.166 | cyclopropyl | Me | H | H | H | F | H | O | |
| 7.167 | cyclopropyl | Me | H | H | H | Cl | H | O | |
| 7.168 | cyclopropyl | F | H | H | H | H | H | direct bond | |
| 7.169 | cyclopropyl | F | H | H | H | Me | H | direct bond | |
| 7.170 | cyclopropyl | F | H | H | H | F | H | direct bond | |
| 7.171 | cyclopropyl | F | H | H | H | Cl | H | direct bond | |
| 7.172 | cyclopropyl | F | H | H | H | Br | H | direct bond | |
| 7.173 | cyclopropyl | F | H | Me | H | Me | H | direct bond | |
| 7.174 | cyclopropyl | F | H | H | Me | Me | H | direct bond | |
| 7.175 | cyclopropyl | F | H | H | H | Me | Me | direct bond | |
| 7.176 | cyclopropyl | F | H | H | F | Me | H | direct bond | |
| 7.177 | cyclopropyl | F | H | H | Cl | Cl | H | direct bond | |
| 7.178 | cyclopropyl | F | H | H | H | H | H | CH₂ | |
| 7.179 | cyclopropyl | F | H | H | H | Me | H | CH₂ | |
| 7.180 | cyclopropyl | F | H | H | H | F | H | CH₂ | |
| 7.181 | cyclopropyl | F | H | H | H | Cl | H | CH₂ | |
| 7.182 | cyclopropyl | F | H | Me | H | Me | H | CH₂ | |
| 7.183 | cyclopropyl | F | H | H | Me | Me | H | CH₂ | |
| 7.184 | cyclopropyl | F | H | H | H | Me | Me | CH₂ | |
| 7.185 | cyclopropyl | F | H | H | F | Me | H | CH₂ | |
| 7.186 | cyclopropyl | F | H | H | Cl | Cl | H | CH₂ | |
| 7.187 | cyclopropyl | F | H | H | H | H | H | O | |

TABLE 7-continued

Compounds of formula (Ij-1):

(Ij-1)

[In the compounds of formula (Ij-1) the marked 1* carbon atom is achiral]

| Cpd | R$^1$ | R$^2$ | R$^3$ | R$^7$ | R$^8$ | R$^9$ | R$^{10}$ | A | Physical data |
|---|---|---|---|---|---|---|---|---|---|
| 7.188 | cyclopropyl | F | H | H | Me | H | | O | |
| 7.189 | cyclopropyl | F | H | H | F | H | | O | |
| 7.190 | cyclopropyl | F | H | H | Cl | H | | O | |
| 7.191 | cyclopropyl | Cl | H | H | H | H | | direct bond | |
| 7.192 | cyclopropyl | Cl | H | H | Me | H | | direct bond | |
| 7.193 | cyclopropyl | Cl | H | H | F | H | | direct bond | |
| 7.194 | cyclopropyl | Cl | H | H | Cl | H | | direct bond | |
| 7.195 | cyclopropyl | Cl | H | H | H | H | | CH$_2$ | |
| 7.196 | cyclopropyl | Cl | H | H | Me | H | | CH$_2$ | |
| 7.197 | cyclopropyl | Cl | H | H | F | H | | CH$_2$ | |
| 7.198 | cyclopropyl | Cl | H | H | Cl | H | | CH$_2$ | |
| 7.199 | cyclopropyl | Cl | H | H | H | H | | O | |
| 7.200 | cyclopropyl | Cl | H | H | Me | H | | O | |
| 7.201 | cyclopropyl | Cl | H | H | F | H | | O | |
| 7.202 | cyclopropyl | Cl | H | H | Cl | H | | O | |
| 7.203 | Me | Me | F | H | H | H | H | CH$_2$ | white solid |
| 7.204 | Me | Me | F | H | H | Me | H | CH$_2$ | |
| 7.205 | Me | Me | F | H | H | F | H | CH$_2$ | |
| 7.206 | Me | Me | F | H | H | Cl | H | CH$_2$ | |
| 7.207 | Me | Me | F | H | Me | H | Me | H | CH$_2$ | |
| 7.208 | Me | Me | F | H | Me | Me | H | CH$_2$ | |
| 7.209 | Me | Me | F | H | H | Me | Me | CH$_2$ | |
| 7.210 | Me | Me | F | H | F | Me | H | CH$_2$ | |
| 7.211 | Me | Me | F | H | Cl | H | H | CH$_2$ | |
| 7.212 | Me | Me | F | H | H | H | H | O | |
| 7.213 | Me | Me | F | H | H | Me | H | O | |
| 7.214 | Me | Me | F | H | H | F | H | O | |
| 7.215 | Me | Me | F | H | H | Cl | H | O | |
| 7.216 | Me | Me | Cl | H | H | H | H | direct bond | |
| 7.217 | Me | Me | Cl | H | H | Me | H | direct bond | |
| 7.218 | Me | Me | Cl | H | H | F | H | direct bond | |
| 7.219 | Me | Me | Cl | H | H | Cl | H | direct bond | |
| 7.220 | Me | Me | Cl | H | H | H | H | CH$_2$ | |
| 7.221 | Me | Me | Cl | H | H | Me | H | CH$_2$ | |
| 7.222 | Me | Me | Cl | H | H | F | H | CH$_2$ | |
| 7.223 | Me | Me | Cl | H | H | Cl | H | CH$_2$ | |
| 7.224 | Me | Me | Cl | H | H | H | H | O | |
| 7.225 | Me | Me | Cl | H | H | Me | H | O | |
| 7.226 | Me | Me | Cl | H | H | F | H | O | |
| 7.227 | Me | Me | Cl | H | H | Cl | H | O | |
| 7.228 | Me | Me | F | H | H | H | H | direct bond | white solid |
| 7.229 | Me | Me | F | H | H | Me | H | direct bond | white solid |
| 7.230 | Me | Me | F | H | H | F | H | direct bond | |
| 7.231 | Me | Me | F | H | H | Cl | H | direct bond | |
| 7.232 | Me | Me | F | H | H | Br | H | direct bond | |
| 7.233 | Me | Me | F | Me | H | Me | H | direct bond | |
| 7.234 | Me | Me | F | H | Me | Me | H | direct bond | |
| 7.235 | Me | Me | F | H | H | Me | Me | direct bond | |
| 7.236 | Me | Me | F | H | F | Me | H | direct bond | |
| 7.237 | Me | Me | F | H | Cl | Cl | H | direct bond | |
| 7.238 | CH$_2$-SCF$_3$ | H | H | H | H | Me | H | direct bond | waxy |
| 7.239 | F | F | F | H | H | H | H | direct bond | solid |
| 7.240 | F | F | F | H | H | Me | H | direct bond | solid |
| 7.241 | CH$_2$-SCF$_3$ | H | H | H | H | H | H | direct bond | solid |
| 7.242 | CN | H | H | H | H | H | H | direct bond | white solid |
| 7.243 | CN | F | H | H | H | Me | H | direct bond | solid |
| 7.244 | F | F | H | H | H | H | H | direct bond | solid |
| 7.245 | Pr | H | H | H | H | Me | H | direct bond | white solid |

Notes to physical data in Table 7 (reference is made to the compound no. in Table 7):
Cpd. 7.1: mp 163.5° C.;
Cpd. 7.2: mp 90-92° C., optical rotation +179.4°;
Cpd. 7.72: mp 58-60° C.;
Cpd. 7.203: optical rotation +83.4°
Cpd. 7.239: mp 180-183° C., optical rotation +153.4°;
Cpd. 7.240: mp 80-83° C.;
Cpd. 7.241: mp 50-52° C., optical rotation +109.6°;
Cpd. 7.242: optical rotation +116.2°;
Cpd. 7.243: mp 64-66° C., optical rotation +135.0°;
Cpd. 7.244: mp 72-76° C.

TABLE 8

Compounds of formula (Ik):

(Ik)

[In the compounds of formula (Ij-1) the carbon atom marked 1* is achiral]

| Cpd | R$^1$ | R$^2$ | R$^3$ | R$^7$ | R$^8$ | R$^9$ | R$^{10}$ | A | Physical data |
|---|---|---|---|---|---|---|---|---|---|
| 8.1 | H | H | H | H | H | H | H | direct bond | white solid |
| 8.2 | H | H | H | H | H | Me | H | direct bond | white solid |
| 8.3 | H | H | H | H | H | F | H | direct bond | solid |
| 8.4 | H | H | H | H | H | Cl | H | direct bond | |
| 8.5 | H | H | H | H | H | Br | H | direct bond | |
| 8.6 | H | H | H | H | Me | H | Me | direct bond | |
| 8.7 | H | H | H | H | Me | Me | H | direct bond | wax |
| 8.8 | H | H | H | H | H | Me | Me | direct bond | |
| 8.9 | H | H | H | H | F | Me | H | direct bond | |

TABLE 8-continued

Compounds of formula (Ik):

[In the compounds of formula (Ij-1) the carbon atom marked 1* is achiral]

| Cpd | R$^1$ | R$^2$ | R$^3$ | R$^7$ | R$^8$ | R$^9$ | R$^{10}$ | A | Physical data |
|---|---|---|---|---|---|---|---|---|---|
| 8.10 | H | H | H | H | Cl | Cl | H | direct bond | |
| 8.11 | H | H | H | H | H | H | H | CH$_2$ | white foam |
| 8.12 | H | H | H | H | H | Me | H | CH$_2$ | solid |
| 8.13 | H | H | H | H | H | F | H | CH$_2$ | |
| 8.14 | H | H | H | H | H | Cl | H | CH$_2$ | |
| 8.15 | H | H | H | Me | H | Me | H | CH$_2$ | solid |
| 8.16 | H | H | H | H | Me | Me | H | CH$_2$ | |
| 8.17 | H | H | H | H | H | Me | Me | CH$_2$ | |
| 8.18 | H | H | H | H | F | Me | H | CH$_2$ | |
| 8.19 | H | H | H | H | Cl | Cl | H | CH$_2$ | |
| 8.20 | H | H | H | H | H | H | H | O | |
| 8.21 | H | H | H | H | H | Me | H | O | solid |
| 8.22 | H | H | H | H | H | F | H | O | |
| 8.23 | H | H | H | H | H | Cl | H | O | |
| 8.24 | Me | H | H | H | H | H | H | direct bond | solid |
| 8.25 | Me | H | H | H | H | Me | H | direct bond | yellow syrup |
| 8.26 | Me | H | H | H | H | F | H | direct bond | solid |
| 8.27 | Me | H | H | H | H | Cl | H | direct bond | |
| 8.28 | Me | H | H | H | H | Br | H | direct bond | |
| 8.29 | Me | H | H | Me | H | Me | H | direct bond | |
| 8.30 | Me | H | H | H | Me | Me | H | direct bond | |
| 8.31 | Me | H | H | H | H | Me | Me | direct bond | |
| 8.32 | Me | H | H | H | F | Me | H | direct bond | |
| 8.33 | Me | H | H | H | Cl | Cl | H | direct bond | |
| 8.34 | Me | H | H | H | H | H | H | CH$_2$ | solid foam |
| 8.35 | Me | H | H | H | H | Me | H | CH$_2$ | solid |
| 8.36 | Me | H | H | H | H | F | H | CH$_2$ | |
| 8.37 | Me | H | H | H | H | Cl | H | CH$_2$ | |
| 8.38 | Me | H | H | Me | H | Me | H | CH$_2$ | solid |
| 8.39 | Me | H | H | H | Me | Me | H | CH$_2$ | |
| 8.40 | Me | H | H | H | H | Me | Me | CH$_2$ | |
| 8.41 | Me | H | H | H | F | Me | H | CH$_2$ | |
| 8.42 | Me | H | H | H | Cl | Cl | H | CH$_2$ | |
| 8.43 | Me | H | H | H | H | H | H | O | |
| 8.44 | Me | H | H | H | H | Me | H | O | solid |
| 8.45 | Me | H | H | H | H | F | H | O | |
| 8.46 | Me | H | H | H | H | Cl | H | O | |
| 8.47 | Et | H | H | H | H | H | H | direct bond | |
| 8.48 | Et | H | H | H | H | Me | H | direct bond | colourless foam |
| 8.49 | Et | H | H | H | H | F | H | direct bond | solid |
| 8.50 | Et | H | H | H | H | Cl | H | direct bond | |
| 8.51 | Et | H | H | H | H | Br | H | direct bond | |
| 8.52 | Et | H | H | Me | H | Me | H | direct bond | |
| 8.53 | Et | H | H | H | Me | Me | H | direct bond | |
| 8.54 | Et | H | H | H | H | Me | Me | direct bond | |
| 8.55 | Et | H | H | H | F | Me | H | direct bond | |
| 8.56 | Et | H | H | H | Cl | Cl | H | direct bond | |
| 8.57 | Et | H | H | H | H | H | H | CH$_2$ | |
| 8.58 | Et | H | H | H | H | Me | H | CH$_2$ | solid |
| 8.59 | Et | H | H | H | H | F | H | CH$_2$ | |
| 8.60 | Et | H | H | H | H | Cl | H | CH$_2$ | |
| 8.61 | Et | H | H | Me | H | Me | H | CH$_2$ | solid |
| 8.62 | Et | H | H | H | Me | Me | H | CH$_2$ | |
| 8.63 | Et | H | H | H | H | Me | Me | CH$_2$ | |
| 8.64 | Et | H | H | H | F | Me | H | CH$_2$ | |
| 8.65 | Me | Me | H | Cl | H | Cl | H | O | |
| 8.66 | Me | Me | H | H | H | H | H | direct bond | |
| 8.67 | Me | Me | H | H | H | Me | H | direct bond | white solid |
| 8.68 | Me | Me | H | H | H | F | H | direct bond | solid |
| 8.69 | Me | Me | H | H | H | Cl | H | direct bond | |
| 8.70 | Me | Me | H | H | H | H | H | CH$_2$ | |
| 8.71 | Me | Me | H | H | H | Me | H | CH$_2$ | solid |
| 8.72 | Me | Me | H | H | H | F | H | CH$_2$ | |
| 8.73 | Me | Me | H | H | H | Cl | H | CH$_2$ | |
| 8.74 | Me | Me | H | H | H | H | H | O | |
| 8.75 | Me | Me | H | H | H | Me | H | O | solid |
| 8.76 | Me | Me | H | H | H | F | H | O | |
| 8.77 | Me | Me | H | H | H | Cl | H | O | |
| 8.78 | Cl | Me | Cl | H | H | H | H | direct bond | |
| 8.79 | Cl | Me | Cl | H | H | Me | H | direct bond | colourless solid |
| 8.80 | Cl | Me | Cl | H | H | F | H | direct bond | |
| 8.81 | Cl | Me | Cl | H | H | Cl | H | direct bond | |
| 8.82 | Cl | Me | Cl | H | H | H | H | CH$_2$ | |
| 8.83 | Cl | Me | Cl | H | H | Me | H | CH$_2$ | |
| 8.84 | Cl | Me | Cl | H | H | F | H | CH$_2$ | |
| 8.85 | Cl | Me | Cl | H | H | Cl | H | CH$_2$ | |
| 8.86 | Cl | Me | Cl | H | H | H | H | O | |
| 8.87 | Cl | Me | Cl | H | H | Me | H | O | |
| 8.88 | Cl | Me | Cl | H | H | F | H | O | |
| 8.89 | Cl | Me | Cl | H | H | Cl | H | O | |
| 8.90 | H | H | F | H | H | H | H | direct bond | solid |
| 8.91 | H | H | F | H | H | Me | H | direct bond | |
| 8.92 | H | H | F | H | H | F | H | direct bond | |
| 8.93 | H | H | F | H | H | Cl | H | direct bond | |
| 8.94 | H | H | F | H | H | Br | H | direct bond | |
| 8.95 | H | H | F | Me | H | Me | H | direct bond | |
| 8.96 | H | H | F | H | Me | Me | H | direct bond | |
| 8.97 | H | H | F | H | H | Me | Me | direct bond | |
| 8.98 | H | H | F | H | F | Me | H | direct bond | |
| 8.99 | H | H | F | H | Cl | Cl | H | direct bond | |
| 8.100 | H | H | F | H | H | H | H | CH$_2$ | solid |
| 8.101 | H | H | F | H | H | Me | H | CH$_2$ | |
| 8.102 | H | H | F | H | H | F | H | CH$_2$ | |
| 8.103 | H | H | F | H | H | Cl | H | CH$_2$ | |
| 8.104 | H | H | F | Me | H | Me | H | CH$_2$ | |
| 8.105 | H | H | F | H | Me | Me | H | CH$_2$ | |
| 8.106 | H | H | F | H | H | Me | Me | CH$_2$ | |
| 8.107 | H | H | F | H | F | Me | H | CH$_2$ | |
| 8.108 | H | H | F | H | Cl | Cl | H | CH$_2$ | |
| 8.109 | H | H | F | H | H | H | H | O | |
| 8.110 | H | H | F | H | H | Me | H | O | |
| 8.111 | H | H | F | H | H | F | H | O | |
| 8.112 | H | H | F | H | H | Cl | H | O | |
| 8.113 | H | H | Cl | H | H | H | H | direct bond | solid |
| 8.114 | H | H | Cl | H | H | Me | H | direct bond | |
| 8.115 | H | H | Cl | H | H | F | H | direct bond | |

TABLE 8-continued

Compounds of formula (Ik):

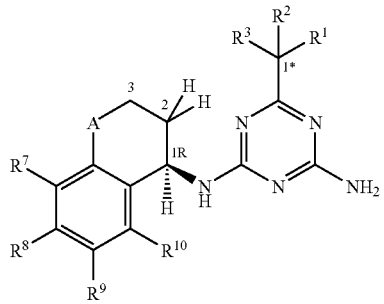

[In the compounds of formula (Ij-1) the carbon atom marked 1* is achiral]

| Cpd | R¹ | R² | R³ | R⁷ | R⁸ | R⁹ | R¹⁰ | A | Physical data |
|---|---|---|---|---|---|---|---|---|---|
| 8.116 | H | H | Cl | H | H | Cl | H | direct bond | |
| 8.117 | H | H | Cl | H | H | H | H | CH₂ | waxy |
| 8.118 | H | H | Cl | H | H | Me | H | CH₂ | |
| 8.119 | H | H | Cl | H | H | F | H | CH₂ | |
| 8.120 | H | H | Cl | H | H | Cl | H | CH₂ | |
| 8.121 | H | H | Cl | H | H | H | H | O | |
| 8.122 | H | H | Cl | H | H | Me | H | O | |
| 8.123 | H | H | Cl | H | H | F | H | O | |
| 8.124 | H | H | Cl | H | H | Cl | H | O | |
| 8.125 | cyclopropyl | H | H | H | H | H | H | direct bond | |
| 8.126 | cyclopropyl | H | H | H | H | Me | H | direct bond | |
| 8.127 | cyclopropyl | H | H | H | H | F | H | direct bond | |
| 8.128 | cyclopropyl | H | H | H | H | Cl | H | direct bond | |
| 8.129 | cyclopropyl | H | H | H | H | Br | H | direct bond | |
| 8.130 | cyclopropyl | H | Me | H | Me | H | direct bond | | |
| 8.131 | cyclopropyl | H | H | Me | Me | H | direct bond | | |
| 8.132 | cyclopropyl | H | H | H | Me | Me | direct bond | | |
| 8.133 | cyclopropyl | H | F | H | Me | H | direct bond | | |
| 8.134 | cyclopropyl | H | H | Cl | Cl | H | direct bond | | |
| 8.135 | cyclopropyl | H | H | H | H | H | H | CH₂ | |
| 8.136 | cyclopropyl | H | H | H | H | Me | H | CH₂ | |
| 8.137 | cyclopropyl | H | H | H | H | F | H | CH₂ | |
| 8.138 | cyclopropyl | H | H | H | H | Cl | H | CH₂ | |
| 8.139 | cyclopropyl | H | Me | H | Me | H | CH₂ | | |
| 8.140 | cyclopropyl | H | H | Me | Me | H | CH₂ | | |
| 8.141 | cyclopropyl | H | H | H | Me | Me | CH₂ | | |
| 8.142 | cyclopropyl | H | F | H | Me | H | CH₂ | | |
| 8.143 | cyclopropyl | H | H | Cl | Cl | H | CH₂ | | |
| 8.144 | cyclopropyl | H | H | H | H | H | H | O | |
| 8.145 | cyclopropyl | H | H | H | H | Me | H | O | |
| 8.146 | cyclopropyl | H | H | H | H | F | H | O | |
| 8.147 | cyclopropyl | H | H | H | H | Cl | H | O | |
| 8.148 | cyclopropyl | Me | H | H | H | H | H | direct bond | waxy |
| 8.149 | cyclopropyl | Me | H | H | H | Me | H | direct bond | |
| 8.150 | cyclopropyl | Me | H | H | H | F | H | direct bond | |
| 8.151 | cyclopropyl | Me | H | H | H | Cl | H | direct bond | |
| 8.152 | cyclopropyl | Me | H | H | H | H | H | CH₂ | wax |
| 8.153 | cyclopropyl | Me | H | H | H | Me | H | CH₂ | |
| 8.154 | cyclopropyl | Me | H | H | H | F | H | CH₂ | |
| 8.155 | cyclopropyl | Me | H | H | H | Cl | H | CH₂ | |
| 8.156 | cyclopropyl | Me | H | H | H | H | H | O | |
| 8.157 | cyclopropyl | Me | H | H | H | Me | H | O | |
| 8.158 | cyclopropyl | Me | H | H | H | F | H | O | |
| 8.159 | cyclopropyl | Me | H | H | H | Cl | H | O | |
| 8.160 | cyclopropyl | F | H | H | H | H | H | direct bond | solid |
| 8.161 | cyclopropyl | F | H | H | H | Me | H | direct bond | |
| 8.162 | cyclopropyl | F | H | H | H | F | H | direct bond | |
| 8.163 | cyclopropyl | F | H | H | H | Cl | H | direct bond | |
| 8.164 | cyclopropyl | F | H | H | H | Br | H | direct bond | |
| 8.165 | cyclopropyl | F | Me | H | Me | H | direct bond | | |
| 8.166 | cyclopropyl | F | H | Me | Me | H | direct bond | | |
| 8.167 | cyclopropyl | F | H | H | Me | Me | direct bond | | |
| 8.168 | cyclopropyl | F | H | F | Me | H | direct bond | | |
| 8.169 | cyclopropyl | F | H | Cl | Cl | H | direct bond | | |
| 8.170 | cyclopropyl | F | H | H | H | H | H | CH₂ | solid |
| 8.171 | cyclopropyl | F | H | H | H | Me | H | CH₂ | |
| 8.172 | cyclopropyl | F | H | H | H | F | H | CH₂ | |
| 8.173 | cyclopropyl | F | H | H | H | Cl | H | CH₂ | |
| 8.174 | cyclopropyl | F | Me | H | Me | H | CH₂ | | |
| 8.175 | cyclopropyl | F | H | Me | Me | H | CH₂ | | |
| 8.176 | cyclopropyl | F | H | H | Me | Me | CH₂ | | |
| 8.177 | cyclopropyl | F | H | F | Me | H | CH₂ | | |
| 8.178 | cyclopropyl | F | H | Cl | Cl | H | CH₂ | | |
| 8.179 | cyclopropyl | F | H | H | H | H | H | O | |
| 8.180 | cyclopropyl | F | H | H | H | Me | H | O | |
| 8.181 | cyclopropyl | F | H | H | H | F | H | O | |
| 8.182 | cyclopropyl | F | H | H | H | Cl | H | O | |
| 8.183 | cyclopropyl | Cl | H | H | H | H | H | direct bond | solid |
| 8.184 | cyclopropyl | Cl | H | H | H | Me | H | direct bond | |
| 8.185 | cyclopropyl | Cl | H | H | H | F | H | direct bond | |
| 8.186 | cyclopropyl | Cl | H | H | H | Cl | H | direct bond | |
| 8.187 | cyclopropyl | Cl | H | H | H | H | H | CH₂ | solid |
| 8.188 | cyclopropyl | Cl | H | H | H | Me | H | CH₂ | |
| 8.189 | cyclopropyl | Cl | H | H | H | F | H | CH₂ | |
| 8.190 | cyclopropyl | Cl | H | H | H | Cl | H | CH₂ | |
| 8.191 | cyclopropyl | Cl | H | H | H | H | H | O | |
| 8.192 | cyclopropyl | Cl | H | H | H | Me | H | O | |
| 8.193 | cyclopropyl | Cl | H | H | H | F | H | O | |
| 8.194 | cyclopropyl | Cl | H | H | H | Cl | H | O | |
| 8.195 | Me | Me | F | H | H | H | H | direct bond | solid |
| 8.196 | Me | Me | F | H | H | Me | H | direct bond | light brown solid |
| 8.197 | Me | Me | F | H | H | F | H | direct bond | solid |
| 8.198 | Me | Me | F | H | H | Cl | H | direct bond | |
| 8.199 | Me | Me | F | H | H | Br | H | direct bond | |
| 8.200 | Me | Me | F | Me | H | Me | H | direct bond | |
| 8.201 | Me | Me | F | H | Me | Me | H | direct bond | solid foam |
| 8.202 | Me | Me | F | H | H | Me | Me | direct bond | |
| 8.203 | Me | Me | F | H | F | Me | H | direct bond | |
| 8.204 | Me | Me | F | H | Cl | Cl | H | direct bond | |
| 8.205 | Me | Me | F | H | H | H | H | CH₂ | beige solid |
| 8.206 | Me | Me | F | H | H | Me | H | CH₂ | solid |
| 8.207 | Me | Me | F | H | H | F | H | CH₂ | |
| 8.208 | Me | Me | F | H | H | Cl | H | CH₂ | |
| 8.209 | Me | Me | F | Me | H | Me | H | CH₂ | solid |
| 8.210 | Me | Me | F | H | Me | Me | H | CH₂ | |
| 8.211 | Me | Me | F | H | H | Me | Me | CH₂ | |
| 8.212 | Me | Me | F | H | F | Me | H | CH₂ | |
| 8.213 | Me | Me | F | H | Cl | Cl | H | CH₂ | |
| 8.214 | Me | Me | F | H | H | H | H | O | |
| 8.215 | Me | Me | F | H | H | Me | H | O | solid |
| 8.216 | Me | Me | F | H | H | F | H | O | |
| 8.217 | Me | Me | F | H | H | Cl | H | O | |

TABLE 8-continued

Compounds of formula (Ik):

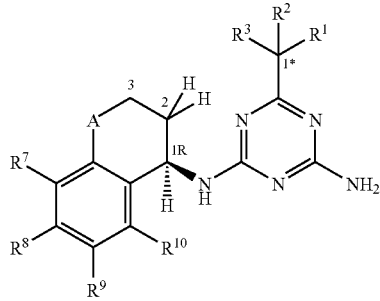

[In the compounds of formula (Ij-1) the carbon atom marked 1* is achiral]

| Cpd | R¹ | R² | R³ | R⁷ | R⁸ | R⁹ | R¹⁰ | A | Physical data |
|---|---|---|---|---|---|---|---|---|---|
| 8.218 | Me | Me | Cl | H | H | H | H | direct bond | |
| 8.219 | Me | Me | Cl | H | H | Me | H | direct bond | colorless solid |
| 8.220 | Me | Me | Cl | H | H | F | H | direct bond | |
| 8.221 | Me | Me | Cl | H | H | Cl | H | direct bond | |
| 8.222 | Me | Me | Cl | H | H | H | H | CH₂ | |
| 8.223 | Me | Me | Cl | H | H | Me | H | CH₂ | |
| 8.224 | Me | Me | Cl | H | H | F | H | CH₂ | |
| 8.225 | Me | Me | Cl | H | H | Cl | H | CH₂ | |
| 8.226 | Me | Me | Cl | H | H | H | H | O | |
| 8.227 | Me | Me | Cl | H | H | Me | H | O | |
| 8.228 | Me | Me | Cl | H | H | F | H | O | |
| 8.229 | Et | H | H | H | Cl | Cl | H | CH₂ | |
| 8.230 | Et | H | H | H | H | H | H | O | |
| 8.231 | Et | H | H | H | H | Me | H | O | solid |
| 8.232 | Et | H | H | H | H | F | H | O | |
| 8.233 | OMe | H | H | H | H | H | H | direct bond | solid |
| 8.234 | OMe | H | H | H | H | H | H | CH₂ | solid |
| 8.235 | OMe | H | H | H | H | Me | H | direct bond | |
| 8.236 | OMe | H | H | H | H | Me | H | CH₂ | |
| 8.237 | Me | Me | F | F | H | H | H | O | solid |
| 8.238 | H | H | H | F | H | H | H | O | white solid |
| 8.239 | Me | H | H | F | H | H | H | O | white solid |
| 8.240 | Et | H | H | F | H | H | H | O | solid |
| 8.241 | Me | Me | F | Me | Me | H | H | O | waxy |
| 8.242 | Me | H | H | Me | Me | H | H | O | waxy |
| 8.243 | Me | Me | F | H | H | OMe | H | direct bond | waxy |
| 8.244 | Me | H | H | H | H | OMe | H | direct bond | waxy |
| 8.245 | Me | Me | F | H | H | Et | H | direct bond | solid |
| 8.246 | H | H | H | H | H | Et | H | direct bond | solid |
| 8.247 | Me | Me | H | H | H | Et | H | direct bond | solid |
| 8.248 | Me | H | H | H | H | Et | H | direct bond | solid |
| 8.249 | Et | H | H | H | H | Et | H | direct bond | solid |
| 8.250 | CH₂-SCF₃ | H | H | H | H | Et | H | direct bond | waxy |
| 8.251 | CH₂-SCF₃ | H | H | H | H | Me | H | CH₂ | waxy |
| 8.252 | Me | Me | H | Me | H | Me | H | CH₂ | solid |
| 8.253 | OMe | H | H | Me | H | Me | H | CH₂ | white solid |
| 8.254 | F | F | F | H | H | H | H | CH₂ | solid |
| 8.255 | CN | H | H | H | H | H | H | CH₂ | white solid |
| 8.256 | F | F | H | H | H | H | H | CH₂ | solid |
| 8.257 | Pr | H | H | H | H | Et | H | CH₂ | solid |

Notes to physical data in Table 8 (reference is made to the compound no. in Table 8):
Cpd. 8.1: mp 94-96° C., optical rotation +87.4°;
Cpd. 8.2: mp 100-102° C.;
Cpd. 8.3: mp 87-89° C., optical rotation +97.2°;
Cpd. 8.11: optical rotation +78.7°;
Cpd. 8.12: mp 95-98° C., optical rotation +73.5°;
Cpd. 8.15: mp 100-103° C., optical rotation +92.1°;
Cpd. 8.21: mp 95-97° C., optical rotation +44.3°;
Cpd. 8.24: mp 65-70° C., optical rotation +95.7°;
Cpd. 8.26: mp 77-78° C., optical rotation +80.0°;
Cpd. 8.34: optical rotation +98.5°;
Cpd. 8.35: mp 77-80° C., optical rotation +79.3°;
Cpd. 8.38: mp 172-174° C.;
Cpd. 8.44: mp 75-79° C., optical rotation +56.3°;
Cpd. 8.49: mp 138-139° C., optical rotation +122.1°;
Cpd. 8.58: mp 135-138° C., optical rotation +69.0°;
Cpd. 8.61: mp 178-180° C.;
Cpd. 8.67: mp 83-84° C.;
Cpd. 8.68: mp 67-68° C., optical rotation +74.2°;
Cpd. 8.71: mp 73-75° C., optical rotation +77.7°;
Cpd. 8.75: mp 75-78° C., optical rotation +59.4°;
Cpd. 8.79: mp 149-151° C.;
Cpd. 8.90: mp 163-165° C., optical rotation +91.6°;
Cpd. 8.100: mp 114-117° C., optical rotation +94.1°;
Cpd. 8.113: mp 63-68° C., optical rotation +77.6°;
Cpd. 8.117: optical rotation +64.0°;
Cpd. 8.152: optical rotation +75.3°;
Cpd. 8.160: mp 70-75° C., optical rotation +75.0°;
Cpd. 8.195: mp 125-126° C., optical rotation +87.7°;
Cpd. 8.196: mp 87-89° C.
Cpd. 8.197: mp 87-89° C., optical rotation +68.8°;
Cpd. 8.205: mp 165-167° C.;
Cpd. 8.206: mp 87-90° C., optical rotation +60.5°;
Cpd. 8.209: mp 90-93° C.;
Cpd. 8.215: mp 100-108° C., optical rotation +42.0°;
Cpd. 8.219: mp 136-138° C.;
Cpd. 8.231: mp 70-75° C., optical rotation +49.3°;
Cpd. 8.233: mp 148-155° C., optical rotation +86.9°;
Cpd. 8.234: mp 135-140° C., optical rotation +81.8°;
Cpd. 8.237: mp 87-95° C., optical rotation +68.0°;
Cpd. 8.239: optical rotation +52.7°;
Cpd. 8.240: mp 87-88° C., optical rotation +55.5°;
Cpd. 8.243: optical rotation +63.0°;
Cpd. 8.245: mp 136-139° C., optical rotation +66.7°;
Cpd. 8.246: mp 73-75° C., optical rotation +75.0°;
Cpd. 8.247: mp 63-70° C., optical rotation +75.0°;
Cpd. 8.248: mp 63-70° C., optical rotation +71.2°;
Cpd. 8.252: mp 70-75° C.;
Cpd. 8.254: mp 170-173° C., optical rotation +109.6°;
Cpd. 8.256: mp 72-76° C.
Cpd. 8.257: mp 63-65° C.

In the following Tables 9 to 14 where the stereochemistry of one or more chiral centres is specified, it is understood that the optical purity at the 1R position is at least 90% in the Table examples.

TABLE 9

Compounds of formula (IL) wherein the stereochemical configuration at the carbon atom marked 1* is chiral but racemic i.e. (1* R,S):

(IL)

| Cpd | R$^1$ | R$^2$ | R$^3$ | R$^6$ | R$^7$ | R$^8$ | R$^9$ | R$^{10}$ | A | Physical data |
|---|---|---|---|---|---|---|---|---|---|---|
| 9.1 | Me | H | F | Me | H | H | H | H | direct bond | |
| 9.2 | Me | H | F | Me | H | H | Me | H | direct bond | |
| 9.3 | Me | H | F | Me | H | F | H | H | direct bond | |
| 9.4 | Me | H | F | Me | H | Cl | H | H | direct bond | |
| 9.5 | Me | H | F | Me | H | Br | H | H | direct bond | |
| 9.6 | Me | H | F | Me | Me | H | Me | H | direct bond | |
| 9.7 | Me | H | F | Me | H | Me | Me | H | direct bond | |
| 9.8 | Me | H | F | Me | H | H | Me | Me | direct bond | |
| 9.9 | Me | H | F | Me | H | F | Me | H | direct bond | |
| 9.10 | Me | H | F | Me | H | Cl | Cl | H | direct bond | |
| 9.11 | Me | H | F | Me | H | H | H | H | CH$_2$ | |
| 9.12 | Me | H | F | Me | H | H | Me | H | CH$_2$ | |
| 9.13 | Me | H | F | Me | H | F | H | H | CH$_2$ | |
| 9.14 | Me | H | F | Me | H | Cl | H | H | CH$_2$ | |
| 9.15 | Me | H | F | Me | Me | H | Me | H | CH$_2$ | |
| 9.16 | Me | H | F | Me | H | Me | Me | H | CH$_2$ | |
| 9.17 | Me | H | F | Me | H | H | Me | Me | CH$_2$ | |
| 9.18 | Me | H | F | Me | H | F | Me | H | CH$_2$ | |
| 9.19 | Me | H | F | Me | H | Cl | Cl | H | CH$_2$ | |
| 9.20 | Me | H | F | Me | H | H | H | H | O | |
| 9.21 | Me | H | F | Me | H | H | Me | H | O | |
| 9.22 | Me | H | F | Me | H | F | H | H | O | |
| 9.23 | Me | H | F | Me | H | Cl | H | H | O | |
| 9.24 | Me | H | Cl | Me | H | H | H | H | direct bond | |
| 9.25 | Me | H | Cl | Me | H | H | Me | H | direct bond | |
| 9.26 | Me | H | Cl | Me | H | F | H | H | direct bond | |
| 9.27 | Me | H | Cl | Me | H | Cl | H | H | direct bond | |
| 9.28 | Me | H | Cl | Me | H | H | H | H | CH$_2$ | |
| 9.29 | Me | H | Cl | Me | H | H | Me | H | CH$_2$ | |
| 9.30 | Me | H | Cl | Me | H | F | H | H | CH$_2$ | |
| 9.31 | Me | H | Cl | Me | H | Cl | H | H | CH$_2$ | |
| 9.32 | Me | H | Cl | Me | H | H | H | H | O | |
| 9.33 | Me | H | Cl | Me | H | H | Me | H | O | |
| 9.34 | Me | H | Cl | Me | H | F | H | H | O | |
| 9.35 | Me | H | Cl | Me | H | Cl | H | H | O | |
| 9.36 | Et | H | F | Me | H | H | H | H | direct bond | white solid |
| 9.37 | Et | H | F | Me | H | H | Me | H | direct bond | white solid |
| 9.38 | Et | H | F | Me | H | F | H | H | direct bond | |
| 9.39 | Et | H | F | Me | H | Cl | H | H | direct bond | |
| 9.40 | Et | H | F | Me | H | Br | H | H | direct bond | |
| 9.41 | Et | H | Cl | Me | H | H | H | H | direct bond | |
| 9.42 | Et | H | Cl | Me | H | H | Me | H | direct bond | |
| 9.43 | Et | H | Cl | Me | H | F | H | H | direct bond | |
| 9.44 | Et | H | Cl | Me | H | Cl | H | H | direct bond | |
| 9.45 | Et | H | Cl | Me | H | Br | H | H | direct bond | |
| 9.46 | Et | H | F | Me | H | H | H | H | CH$_2$ | |
| 9.47 | Et | H | F | Me | H | H | Me | H | CH$_2$ | |
| 9.48 | Et | H | F | Me | H | F | H | H | CH$_2$ | |
| 9.49 | Et | H | F | Me | H | Cl | H | H | CH$_2$ | |
| 9.50 | Et | H | F | Me | H | H | Br | H | CH$_2$ | |
| 9.51 | Et | H | Cl | Me | H | H | H | H | CH$_2$ | |
| 9.52 | Et | H | Cl | Me | H | H | Me | H | CH$_2$ | |
| 9.53 | Et | H | Cl | Me | H | F | H | H | CH$_2$ | |
| 9.54 | Et | H | Cl | Me | H | Cl | H | H | CH$_2$ | |
| 9.55 | Et | H | Cl | Me | H | Br | H | H | CH$_2$ | |
| 9.56 | Et | H | F | Me | H | H | H | H | O | |
| 9.57 | Et | H | F | Me | H | H | Me | H | O | |
| 9.58 | Et | H | F | Me | H | F | H | H | O | |
| 9.59 | Et | H | F | Me | H | Cl | H | H | O | |
| 9.60 | Et | H | F | Me | H | Br | H | H | O | |
| 9.61 | Et | H | Cl | Me | H | H | H | H | O | |
| 9.62 | Et | H | Cl | Me | H | H | Me | H | O | |
| 9.63 | Et | H | Cl | Me | H | F | H | H | O | |
| 9.64 | Et | H | Cl | Me | H | Cl | H | H | O | |
| 9.65 | Et | H | Cl | Me | H | Br | H | H | O | |
| 9.66 | Pr | H | H | Me | H | H | Me | H | direct bond | white solid |

TABLE 10

Compounds of formula (Ia-1) which have a chiral centre at the carbon atom marked 1*, wherein the stereochemical configuration at the carbon atom marked 1* is racemic i.e. (1*RS):

(Ia-1)

| Cpd | R$^1$ | R$^2$ | R$^3$ | R$^7$ | R$^8$ | R$^9$ | R$^{10}$ | A | Physical data |
|---|---|---|---|---|---|---|---|---|---|
| 10.1 | Me | H | F | H | H | H | H | direct bond | white solid |
| 10.2 | Me | H | F | H | H | Me | H | direct bond | white solid |
| 10.3 | Me | H | F | H | F | H | H | direct bond | |
| 10.4 | Me | H | F | H | H | Cl | H | direct bond | |
| 10.5 | Me | H | F | H | H | Br | H | direct bond | |
| 10.6 | Me | H | F | Me | H | Me | H | direct bond | |
| 10.7 | Me | H | F | H | Me | Me | H | direct bond | |
| 10.8 | Me | H | F | H | H | Me | Me | direct bond | |
| 10.9 | Me | H | F | H | F | Me | H | direct bond | |
| 10.10 | Me | H | F | H | Cl | Cl | H | direct bond | |
| 10.11 | Me | H | F | H | H | H | H | CH$_2$ | |
| 10.12 | Me | H | F | H | H | Me | H | CH$_2$ | |

TABLE 10-continued

Compounds of formula (Ia-1) which have a chiral centre at the carbon atom marked 1*, wherein the stereochemical configuration at the carbon atom marked 1* is racemic i.e. (1*RS):

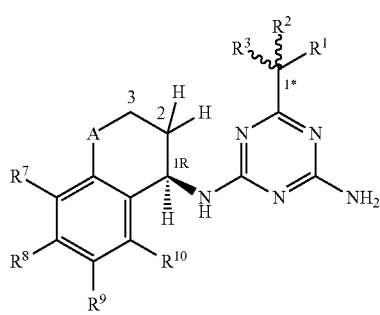

(Ia-1)

| Cpd | R¹ | R² | R³ | R⁷ | R⁸ | R⁹ | R¹⁰ | A | Physical data |
|---|---|---|---|---|---|---|---|---|---|
| 10.13 | Me | H | F | H | H | F | H | CH₂ | |
| 10.14 | Me | H | F | H | H | Cl | H | CH₂ | |
| 10.15 | Me | H | F | Me | H | Me | H | CH₂ | |
| 10.16 | Me | H | F | H | Me | Me | H | CH₂ | |
| 10.17 | Me | H | F | H | H | Me | Me | CH₂ | |
| 10.18 | Me | H | F | H | F | Me | H | CH₂ | |
| 10.19 | Me | H | F | H | Cl | Cl | H | CH₂ | |
| 10.20 | Me | H | F | H | H | H | H | O | |
| 10.21 | Me | H | F | H | H | Me | H | O | |
| 10.22 | Me | H | F | H | H | F | H | O | |
| 10.23 | Me | H | F | H | H | Cl | H | O | |
| 10.24 | Me | H | Cl | H | H | H | H | direct bond | |
| 10.25 | Me | H | Cl | H | H | Me | H | direct bond | |
| 10.26 | Me | H | Cl | H | H | F | H | direct bond | |
| 10.27 | Me | H | Cl | H | H | Cl | H | direct bond | |
| 10.28 | Me | H | Cl | H | H | H | H | CH₂ | |
| 10.29 | Me | H | Cl | H | H | Me | H | CH₂ | |
| 10.30 | Me | H | Cl | H | H | F | H | CH₂ | |
| 10.31 | Me | H | Cl | Me | H | Me | H | CH₂ | |
| 10.32 | Me | H | Cl | H | H | H | H | O | |
| 10.33 | Me | H | Cl | H | H | Me | H | O | |
| 10.34 | Me | H | Cl | H | H | F | H | O | |
| 10.35 | Me | H | Cl | H | H | Cl | H | O | |
| 10.36 | Et | H | F | H | H | H | H | direct bond | |
| 10.37 | Et | H | F | H | H | Me | H | direct bond | white solid (c) |
| 10.38 | Et | H | F | H | H | F | H | direct bond | solid |
| 10.39 | Et | H | F | H | H | Cl | H | direct bond | |
| 10.40 | Et | H | F | H | H | Br | H | direct bond | |
| 10.41 | Et | H | Cl | H | H | H | H | direct bond | |
| 10.42 | Et | H | Cl | H | H | Me | H | direct bond | |
| 10.43 | Et | H | Cl | H | H | F | H | direct bond | |
| 10.44 | Et | H | Cl | H | H | Cl | H | direct bond | |
| 10.45 | Et | H | Cl | H | H | Br | H | direct bond | |
| 10.46 | Et | H | F | H | H | H | H | CH₂ | |
| 10.47 | Et | H | F | H | H | Me | H | CH₂ | solid |
| 10.48 | Et | H | F | H | H | F | H | CH₂ | |
| 10.49 | Et | H | F | H | H | Cl | H | CH₂ | |
| 10.50 | Et | H | F | H | H | Br | H | CH₂ | |
| 10.51 | Et | H | Cl | H | H | H | H | CH₂ | |
| 10.52 | Et | H | Cl | H | H | Me | H | CH₂ | |
| 10.53 | Et | H | Cl | H | H | F | H | CH₂ | |
| 10.54 | Et | H | Cl | H | H | Cl | H | CH₂ | |
| 10.55 | Et | H | Cl | H | H | Br | H | CH₂ | |
| 10.56 | Et | H | F | H | H | H | H | O | |
| 10.57 | Et | H | F | H | H | Me | H | O | solid |
| 10.58 | Et | H | F | H | H | F | H | O | |
| 10.59 | Et | H | F | H | H | Cl | H | O | |
| 10.60 | Et | H | F | H | H | Br | H | O | |
| 10.61 | Et | H | Cl | H | H | H | H | O | |
| 10.62 | Et | H | Cl | H | H | Me | H | O | |
| 10.63 | Et | H | Cl | H | H | F | H | O | |
| 10.64 | Et | H | Cl | H | H | Cl | H | O | |
| 10.65 | Et | H | Cl | H | H | Br | H | O | |
| 10.66 | Pr | H | F | H | H | Me | H | CH₂ | white solid |
| 10.67 | Pr | H | F | Me | H | Me | H | O | solid |
| 10.68 | Et | H | F | Me | H | Me | H | CH₂ | solid |

Notes to physical data in Table 10 (reference is made to the compound no. in Table 10):
Cpd 10.1: mp 147-151° C., optical rotation +91.5°;
Cpd 10.2: mp 92-94° C.;
Cpd 10.37: mp 82-84° C.
Cpd 10.38: mp 76-77° C.;
Cpd 10.47: mp 85-88° C.;
Cpd 10.57: mp 90-93° C.;
Cpd 10.67: mp 80-85° C.;
Cpd 10.68: mp 90-93° C., optical rotation +77.0

TABLE 11

Compounds of formula (Im) wherein the stereochemical configuration at the carbon atom marked 1* is racemic i.e. (1*RS):

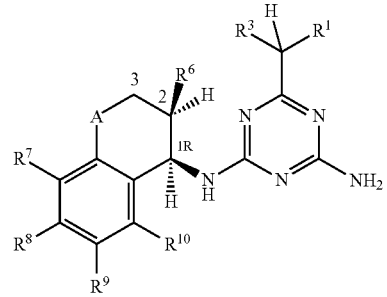

(Im)

| Cpd | R¹ | R³ | R⁶ | R⁷ | R⁸ | R⁹ | R¹⁰ | A | Physical data mp/opt. rot./ appearance |
|---|---|---|---|---|---|---|---|---|---|
| 11.1 | Me | F | Me | H | H | H | H | direct bond | |
| 11.2 | Me | F | Me | H | H | Me | H | direct bond | |
| 11.3 | Me | F | Me | H | H | F | H | direct bond | |
| 11.4 | Me | F | Me | H | H | Cl | H | direct bond | |
| 11.5 | Me | F | Me | H | H | Br | H | direct bond | |
| 11.6 | Me | F | Me | Me | H | Me | H | direct bond | |
| 11.7 | Me | F | Me | H | Me | Me | H | direct bond | |
| 11.8 | Me | F | Me | H | H | Me | Me | direct bond | |
| 11.9 | Me | F | Me | H | F | Me | H | direct bond | |
| 11.10 | Me | F | Me | H | Cl | Cl | H | direct bond | |
| 11.11 | Me | F | Me | H | H | H | H | CH₂ | |
| 11.12 | Me | F | Me | H | H | Me | H | CH₂ | |
| 11.13 | Me | F | Me | H | H | F | H | CH₂ | |
| 11.14 | Me | F | Me | H | H | Cl | H | CH₂ | |
| 11.15 | Me | F | Me | Me | H | Me | H | CH₂ | |
| 11.16 | Me | F | Me | H | Me | Me | H | CH₂ | |
| 11.17 | Me | F | Me | H | H | Me | Me | CH₂ | |

TABLE 11-continued

Compounds of formula (Im) wherein the stereochemical configuration at the carbon atom marked 1* is racemic i.e. (1*RS):

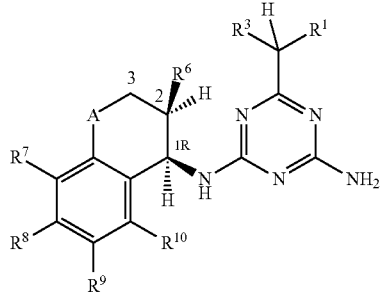

(Im)

| Cpd | R¹ | R³ | R⁶ | R⁷ | R⁸ | R⁹ | R¹⁰ | A | Physical data mp/opt. rot./ appearance |
|---|---|---|---|---|---|---|---|---|---|
| 11.18 | Me | F | Me | H | F | Me | H | CH₂ | |
| 11.19 | Me | F | Me | H | Cl | Cl | H | CH₂ | |
| 11.20 | Me | F | Me | H | H | H | H | O | |
| 11.21 | Me | F | Me | H | H | Me | H | O | |
| 11.22 | Me | F | Me | H | H | F | H | O | |
| 11.23 | Me | F | Me | H | H | Cl | H | O | |
| 11.24 | Me | Cl | Me | H | H | H | H | direct bond | |
| 11.25 | Me | Cl | Me | H | H | Me | H | direct bond | |
| 11.26 | Me | Cl | Me | H | H | F | H | direct bond | |
| 11.27 | Me | Cl | Me | H | H | Cl | H | direct bond | |
| 11.28 | Me | Cl | Me | H | H | H | H | CH₂ | |
| 11.29 | Me | Cl | Me | H | H | Me | H | CH₂ | |
| 11.30 | Me | Cl | Me | H | H | F | H | CH₂ | |
| 11.31 | Me | Cl | Me | H | H | Cl | H | CH₂ | |
| 11.32 | Me | Cl | Me | H | H | H | H | O | |
| 11.33 | Me | Cl | Me | H | H | Me | H | O | |
| 11.34 | Me | Cl | Me | H | H | F | H | O | |
| 11.35 | Me | Cl | Me | H | H | Cl | H | O | |
| 11.36 | Et | F | Me | H | H | H | H | direct bond | |
| 11.37 | Et | F | Me | H | H | Me | H | direct bond | |
| 11.38 | Et | F | Me | H | H | F | H | direct bond | |
| 11.39 | Et | F | Me | H | H | Cl | H | direct bond | |
| 11.40 | Et | F | Me | H | H | Br | H | direct bond | |
| 11.41 | Et | Cl | Me | H | H | H | H | direct bond | |
| 11.42 | Et | Cl | Me | H | H | Me | H | direct bond | |
| 11.43 | Et | Cl | Me | H | H | F | H | direct bond | |
| 11.44 | Et | Cl | Me | H | H | Cl | H | direct bond | |
| 11.45 | Et | Cl | Me | H | H | Br | H | direct bond | |
| 11.46 | Et | F | Me | H | H | H | H | CH₂ | |
| 11.47 | Et | F | Me | H | H | Me | H | CH₂ | |
| 11.48 | Et | F | Me | H | H | F | H | CH₂ | |
| 11.49 | Et | F | Me | H | H | Cl | H | CH₂ | |
| 11.50 | Et | F | Me | H | H | Br | H | CH₂ | |
| 11.51 | Et | Cl | Me | H | H | H | H | CH₂ | |
| 11.52 | Et | Cl | Me | H | H | Me | H | CH₂ | |
| 11.53 | Et | Cl | Me | H | H | F | H | CH₂ | |
| 11.54 | Et | Cl | Me | H | H | Cl | H | CH₂ | |
| 11.55 | Et | Cl | Me | H | H | Br | H | CH₂ | |
| 11.56 | Et | F | Me | H | H | H | H | O | |
| 11.57 | Et | F | Me | H | H | Me | H | O | |
| 11.58 | Et | F | Me | H | H | F | H | O | |
| 11.59 | Et | F | Me | H | H | Cl | H | O | |
| 11.60 | Et | F | Me | H | H | Br | H | O | |
| 11.61 | Et | Cl | Me | H | H | H | H | O | |
| 11.62 | Et | Cl | Me | H | H | Me | H | O | |
| 11.63 | Et | Cl | Me | H | H | F | H | O | |
| 11.64 | Et | Cl | Me | H | H | Cl | H | O | |
| 11.65 | Et | Cl | Me | H | H | Br | H | O | |

TABLE 12

Compounds of formula (In) wherein the stereochemical configuration at the carbon atom marked 2 is racemic i.e. (2RS):

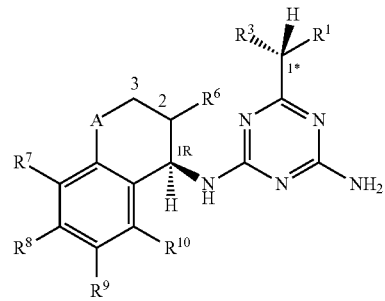

(In)

| Cpd | R¹ | R³ | R⁶ | R⁷ | R⁸ | R⁹ | R¹⁰ | A | Physical data mp/opt. rot./ appearance |
|---|---|---|---|---|---|---|---|---|---|
| 12.1 | Me | F | Me | H | H | H | H | direct bond | |
| 12.2 | Me | F | Me | H | H | Me | H | direct bond | |
| 12.3 | Me | F | Me | H | H | F | H | direct bond | |
| 12.4 | Me | F | Me | H | H | Cl | H | direct bond | |
| 12.5 | Me | F | Me | H | H | Br | H | direct bond | |
| 12.6 | Me | F | Me | Me | H | Me | H | direct bond | |
| 12.7 | Me | F | Me | H | Me | Me | H | direct bond | |
| 12.8 | Me | F | Me | H | H | Me | Me | direct bond | |
| 12.9 | Me | F | Me | H | F | Me | H | direct bond | |
| 12.10 | Me | F | Me | H | Cl | Cl | H | direct bond | |
| 12.11 | Me | F | Me | H | H | H | H | CH₂ | |
| 12.12 | Me | F | Me | H | H | Me | H | CH₂ | |
| 12.13 | Me | F | Me | H | H | F | H | CH₂ | |
| 12.14 | Me | F | Me | H | H | Cl | H | CH₂ | |
| 12.15 | Me | F | Me | Me | H | Me | H | CH₂ | |
| 12.16 | Me | F | Me | H | Me | Me | H | CH₂ | |
| 12.17 | Me | F | Me | H | H | Me | Me | CH₂ | |
| 12.18 | Me | F | Me | H | F | Me | H | CH₂ | |
| 12.19 | Me | F | Me | H | Cl | Cl | H | CH₂ | |
| 12.20 | Me | F | Me | H | H | H | H | O | |
| 12.21 | Me | F | Me | H | H | Me | H | O | |
| 12.22 | Me | F | Me | H | H | F | H | O | |
| 12.23 | Me | F | Me | H | H | Cl | H | O | |
| 12.24 | Me | Cl | Me | H | H | H | H | direct bond | |
| 12.25 | Me | Cl | Me | H | H | Me | H | direct bond | |
| 12.26 | Me | Cl | Me | H | H | F | H | direct bond | |
| 12.27 | Me | Cl | Me | H | H | Cl | H | direct bond | |
| 12.28 | Me | Cl | Me | H | H | H | H | CH₂ | |
| 12.29 | Me | Cl | Me | H | H | Me | H | CH₂ | |
| 12.30 | Me | Cl | Me | H | H | F | H | CH₂ | |
| 12.31 | Me | Cl | Me | H | H | Cl | H | CH₂ | |
| 12.32 | Me | Cl | Me | H | H | H | H | O | |
| 12.33 | Me | Cl | Me | H | H | Me | H | O | |
| 12.34 | Me | Cl | Me | H | H | F | H | O | |
| 12.35 | Me | Cl | Me | H | H | Cl | H | O | |
| 12.36 | Et | F | Me | H | H | H | H | direct bond | |
| 12.37 | Et | F | Me | H | H | Me | H | direct bond | |
| 12.38 | Et | F | Me | H | H | F | H | direct bond | |
| 12.39 | Et | F | Me | H | H | Cl | H | direct bond | |
| 12.40 | Et | F | Me | H | H | Br | H | direct bond | |
| 12.41 | Et | Cl | Me | H | H | H | H | direct bond | |
| 12.42 | Et | Cl | Me | H | H | Me | H | direct bond | |
| 12.43 | Et | Cl | Me | H | H | F | H | direct bond | |
| 12.44 | Et | Cl | Me | H | H | Cl | H | direct bond | |
| 12.45 | Et | Cl | Me | H | H | Br | H | direct bond | |
| 12.46 | Et | F | Me | H | H | H | H | CH₂ | |
| 12.47 | Et | F | Me | H | H | Me | H | CH₂ | |
| 12.48 | Et | F | Me | H | H | F | H | CH₂ | |
| 12.49 | Et | F | Me | H | H | Cl | H | CH₂ | |
| 12.50 | Et | F | Me | H | H | Br | H | CH₂ | |
| 12.51 | Et | Cl | Me | H | H | H | H | CH₂ | |
| 12.52 | Et | Cl | Me | H | H | Me | H | CH₂ | |
| 12.53 | Et | Cl | Me | H | H | F | H | CH₂ | |
| 12.54 | Et | Cl | Me | H | H | Cl | H | CH₂ | |
| 12.55 | Et | Cl | Me | H | H | Br | H | CH₂ | |
| 12.56 | Et | F | Me | H | H | H | H | O | |
| 12.57 | Et | F | Me | H | H | Me | H | O | |

TABLE 12-continued

Compounds of formula (In) wherein the stereochemical configuration at the carbon atom marked 2 is racemic i.e. (2RS):

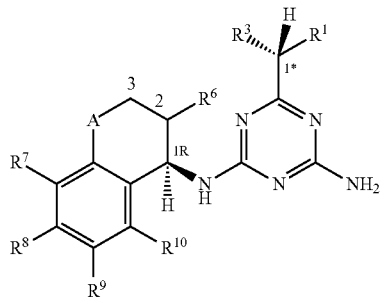

(In)

| Cpd | $R^1$ | $R^3$ | $R^6$ | $R^7$ | $R^8$ | $R^9$ | $R^{10}$ | A | Physical data mp/opt. rot./ appearance |
|---|---|---|---|---|---|---|---|---|---|
| 12.58 | Et | F | Me | H | H | F | H | O | |
| 12.59 | Et | F | Me | H | H | Cl | H | O | |
| 12.60 | Et | F | Me | H | H | Br | H | O | |
| 12.61 | Et | Cl | Me | H | H | H | H | O | |
| 12.62 | Et | Cl | Me | H | H | Me | H | O | |
| 12.63 | Et | Cl | Me | H | H | F | H | O | |
| 12.64 | Et | Cl | Me | H | H | Cl | H | O | |
| 12.65 | Et | Cl | Me | H | H | Br | H | O | |

Table 13: Compounds of formula (Ip) wherein the stereochemical configuration at the carbon atom marked 2 is racemic i.e. (2RS):

TABLE 13

Compounds of formula (Ip) wherein the stereochemical configuration at the carbon atom marked 2 is racemic i.e. (2RS):

(Ip)

| Cpd | $R^1$ | $R^3$ | $R^6$ | $R^7$ | $R^8$ | $R^9$ | $R^{10}$ | A | Physical data mp/opt. rot./ appearance |
|---|---|---|---|---|---|---|---|---|---|
| 13.1 | Me | F | Me | H | H | H | H | direct bond | |
| 13.2 | Me | F | Me | H | H | Me | H | direct bond | |
| 13.3 | Me | F | Me | H | H | F | H | direct bond | |
| 13.4 | Me | F | Me | H | H | Cl | H | direct bond | |
| 13.5 | Me | F | Me | H | H | Br | H | direct bond | |
| 13.6 | Me | F | Me | Me | H | Me | H | direct bond | |
| 13.7 | Me | F | Me | H | Me | Me | H | direct bond | |
| 13.8 | Me | F | Me | H | H | Me | Me | direct bond | |
| 13.9 | Me | F | Me | H | F | Me | H | direct bond | |
| 13.10 | Me | F | Me | H | Cl | Cl | H | direct bond | |
| 13.11 | Me | F | Me | H | H | H | H | $CH_2$ | |
| 13.12 | Me | F | Me | H | H | Me | H | $CH_2$ | |
| 13.13 | Me | F | Me | H | H | F | H | $CH_2$ | |
| 13.14 | Me | F | Me | H | H | Cl | H | $CH_2$ | |
| 13.15 | Me | F | Me | Me | H | Me | H | $CH_2$ | |
| 13.16 | Me | F | Me | H | Me | Me | H | $CH_2$ | |
| 13.17 | Me | F | Me | H | H | Me | Me | $CH_2$ | |
| 13.18 | Me | F | Me | H | F | Me | H | $CH_2$ | |
| 13.19 | Me | F | Me | H | Cl | Cl | H | $CH_2$ | |
| 13.20 | Me | F | Me | H | H | H | H | O | |
| 13.21 | Me | F | Me | H | H | Me | H | O | |
| 13.22 | Me | F | Me | H | H | F | H | O | |
| 13.23 | Me | F | Me | H | H | Cl | H | O | |
| 13.24 | Me | Cl | Me | H | H | H | H | direct bond | |
| 13.25 | Me | Cl | Me | H | H | Me | H | direct bond | |
| 13.26 | Me | Cl | Me | H | H | F | H | direct bond | |
| 13.27 | Me | Cl | Me | H | H | Cl | H | direct bond | |
| 13.28 | Me | Cl | Me | H | H | H | H | $CH_2$ | |
| 13.29 | Me | Cl | Me | H | H | Me | H | $CH_2$ | |
| 13.30 | Me | Cl | Me | H | H | F | H | $CH_2$ | |
| 13.31 | Me | Cl | Me | H | H | Cl | H | $CH_2$ | |
| 13.32 | Me | Cl | Me | H | H | H | H | O | |
| 13.33 | Me | Cl | Me | H | H | Me | H | O | |
| 13.34 | Me | Cl | Me | H | H | F | H | O | |
| 13.35 | Me | Cl | Me | H | H | Cl | H | O | |
| 13.36 | Et | F | Me | H | H | H | H | direct bond | |
| 13.37 | Et | F | Me | H | H | Me | H | direct bond | |
| 13.38 | Et | F | Me | H | H | F | H | direct bond | |
| 13.39 | Et | F | Me | H | H | Cl | H | direct bond | |
| 13.40 | Et | F | Me | H | H | Br | H | direct bond | |
| 13.41 | Et | Cl | Me | H | H | H | H | direct bond | |
| 13.42 | Et | Cl | Me | H | H | Me | H | direct bond | |
| 13.43 | Et | Cl | Me | H | H | F | H | direct bond | |
| 13.44 | Et | Cl | Me | H | H | Cl | H | direct bond | |
| 13.45 | Et | Cl | Me | H | H | Br | H | direct bond | |
| 13.46 | Et | F | Me | H | H | H | H | $CH_2$ | |
| 13.47 | Et | F | Me | H | H | Me | H | $CH_2$ | |
| 13.48 | Et | F | Me | H | H | F | H | $CH_2$ | |
| 13.49 | Et | F | Me | H | H | Cl | H | $CH_2$ | |
| 13.50 | Et | F | Me | H | H | Br | H | $CH_2$ | |
| 13.51 | Et | Cl | Me | H | H | H | H | $CH_2$ | |
| 13.52 | Et | Cl | Me | H | H | Me | H | $CH_2$ | |
| 13.53 | Et | Cl | Me | H | H | F | H | $CH_2$ | |
| 13.54 | Et | Cl | Me | H | H | Cl | H | $CH_2$ | |
| 13.55 | Et | Cl | Me | H | H | Br | H | $CH_2$ | |
| 13.56 | Et | F | Me | H | H | H | H | O | |
| 13.57 | Et | F | Me | H | H | Me | H | O | |
| 13.58 | Et | F | Me | H | H | F | H | O | |
| 13.59 | Et | F | Me | H | H | Cl | H | O | |
| 13.60 | Et | F | Me | H | H | Br | H | O | |
| 13.61 | Et | Cl | Me | H | H | H | H | O | |
| 13.62 | Et | Cl | Me | H | H | Me | H | O | |
| 13.63 | Et | Cl | Me | H | H | F | H | O | |
| 13.64 | Et | Cl | Me | H | H | Cl | H | O | |
| 13.65 | Et | Cl | Me | H | H | Br | H | O | |

TABLE 14

Compounds of formula (Ic-1) wherein the stereochemical configurations at the carbon atoms marked 2 and 1* are racemic i.e. (1*RS, 2RS):

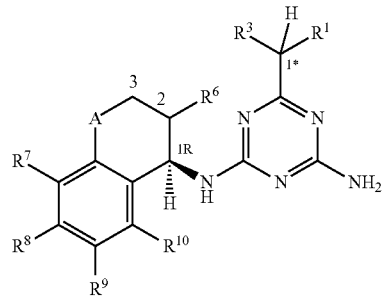

(Ic-1)

| Cpd | $R^1$ | $R^3$ | $R^6$ | $R^7$ | $R^8$ | $R^9$ | $R^{10}$ | A | Physical data mp/opt. rot./ appearance |
|---|---|---|---|---|---|---|---|---|---|
| 14.1 | Me | F | Me | H | H | H | H | direct bond | |
| 14.2 | Me | F | Me | H | H | Me | H | direct bond | |
| 14.3 | Me | F | Me | H | H | F | H | direct bond | |
| 14.4 | Me | F | Me | H | H | Cl | H | direct bond | |
| 14.5 | Me | F | Me | H | H | Br | H | direct bond | |
| 14.6 | Me | F | Me | Me | H | Me | H | direct bond | |
| 14.7 | Me | F | Me | H | Me | Me | H | direct bond | |
| 14.8 | Me | F | Me | H | H | Me | Me | direct bond | |
| 14.9 | Me | F | Me | H | F | Me | H | direct bond | |
| 14.10 | Me | F | Me | H | Cl | Cl | H | direct bond | |
| 14.11 | Me | F | Me | H | H | H | H | $CH_2$ | |
| 14.12 | Me | F | Me | H | H | Me | H | $CH_2$ | |
| 14.13 | Me | F | Me | H | H | F | H | $CH_2$ | |
| 14.14 | Me | F | Me | H | H | Cl | H | $CH_2$ | |
| 14.15 | Me | F | Me | Me | H | Me | H | $CH_2$ | |
| 14.16 | Me | F | Me | H | Me | Me | H | $CH_2$ | |
| 14.17 | Me | F | Me | H | H | Me | Me | $CH_2$ | |
| 14.18 | Me | F | Me | H | F | Me | H | $CH_2$ | |
| 14.19 | Me | F | Me | H | Cl | Cl | H | $CH_2$ | |
| 14.20 | Me | F | Me | H | H | H | H | O | |
| 14.21 | Me | F | Me | H | H | Me | H | O | |
| 14.22 | Me | F | Me | H | H | F | H | O | |
| 14.23 | Me | F | Me | H | H | Cl | H | O | |
| 14.24 | Me | Cl | Me | H | H | H | H | direct bond | |
| 14.25 | Me | Cl | Me | H | H | Me | H | direct bond | |
| 14.26 | Me | Cl | Me | H | H | F | H | direct bond | |
| 14.27 | Me | Cl | Me | H | H | Cl | H | direct bond | |
| 14.28 | Me | Cl | Me | H | H | H | H | $CH_2$ | |
| 14.29 | Me | Cl | Me | H | H | Me | H | $CH_2$ | |
| 14.30 | Me | Cl | Me | H | H | F | H | $CH_2$ | |
| 14.31 | Me | Cl | Me | H | H | Cl | H | $CH_2$ | |
| 14.32 | Me | Cl | Me | H | H | H | H | O | |
| 14.33 | Me | Cl | Me | H | H | Me | H | O | |
| 14.34 | Me | Cl | Me | H | H | F | H | O | |
| 14.35 | Me | Cl | Me | H | H | Cl | H | O | |
| 14.36 | Et | F | Me | H | H | H | H | direct bond | |
| 14.37 | Et | F | Me | H | H | Me | H | direct bond | |
| 14.38 | Et | F | Me | H | H | F | H | direct bond | |
| 14.39 | Et | F | Me | H | H | Cl | H | direct bond | |
| 14.40 | Et | F | Me | H | H | Br | H | direct bond | |
| 14.41 | Et | Cl | Me | H | H | H | H | direct bond | |
| 14.42 | Et | Cl | Me | H | H | Me | H | direct bond | |
| 14.43 | Et | Cl | Me | H | H | F | H | direct bond | |
| 14.44 | Et | Cl | Me | H | H | Cl | H | direct bond | |
| 14.45 | Et | Cl | Me | H | H | Br | H | direct bond | |
| 14.46 | Et | F | Me | H | H | H | H | $CH_2$ | |
| 14.47 | Et | F | Me | H | H | Me | H | $CH_2$ | |
| 14.48 | Et | F | Me | H | H | F | H | $CH_2$ | |
| 14.49 | Et | F | Me | H | H | Cl | H | $CH_2$ | |
| 14.50 | Et | F | Me | H | H | Br | H | $CH_2$ | |
| 14.51 | Et | Cl | Me | H | H | H | H | $CH_2$ | |
| 14.52 | Et | Cl | Me | H | H | Me | H | $CH_2$ | |
| 14.53 | Et | Cl | Me | H | H | F | H | $CH_2$ | |
| 14.54 | Et | Cl | Me | H | H | Cl | H | $CH_2$ | |
| 14.55 | Et | Cl | Me | H | H | Br | H | $CH_2$ | |
| 14.56 | Et | F | Me | H | H | H | H | O | |
| 14.57 | Et | F | Me | H | H | Me | H | O | |
| 14.58 | Et | F | Me | H | H | F | H | O | |
| 14.59 | Et | F | Me | H | H | Cl | H | O | |
| 14.60 | Et | F | Me | H | H | Br | H | O | |
| 14.61 | Et | Cl | Me | H | H | H | H | O | |
| 14.62 | Et | Cl | Me | H | H | Me | H | O | |
| 14.63 | Et | Cl | Me | H | H | F | H | O | |
| 14.64 | Et | Cl | Me | H | H | Cl | H | O | |
| 14.65 | Et | Cl | Me | H | H | Br | H | O | |

The following Table 15 illustrates the intermediate amines of general formula (V) which are used to prepare the above compounds of formula (Ia), (Ia-1), (Ib), (Ic), (Ic-1), (Id), (Id-1), (Ie), (Ie-1), (Ik), (In) and (Ip). For compounds in which $R^6$ is methyl, the configuration at the carbon atom marked 2 is racemic i.e. (2RS).

TABLE 15

| Cpd | $R^6$ | $R^7$ | $R^8$ | $R^9$ | $R^{10}$ | A | Physical data mp/opt. rot./ appearance |
|---|---|---|---|---|---|---|---|
| 15.1 | H | H | H | H | H | direct bond | |
| 15.2 | H | H | H | Me | H | direct bond | HCl salt solid |
| 15.3 | H | H | H | F | H | direct bond | HCl salt solid (a) |
| 15.4 | H | H | H | Cl | H | direct bond | |
| 15.5 | H | H | H | Br | H | direct bond | |
| 15.6 | H | Me | H | Me | H | direct bond | |
| 15.7 | H | H | Me | Me | H | direct bond | (b) |
| 15.8 | H | H | H | Me | Me | direct bond | (c) |
| 15.9 | H | H | F | Me | H | direct bond | (d) |
| 15.10 | H | H | Cl | Cl | H | direct bond | |
| 15.11 | H | H | H | H | H | $CH_2$ | |
| 15.12 | H | H | H | Me | H | $CH_2$ | HCl salt solid mp >260° C. (e) |
| 15.13 | H | H | H | F | H | $CH_2$ | |
| 15.14 | H | H | H | Cl | H | $CH_2$ | |
| 15.15 | H | H | H | Br | H | $CH_2$ | |
| 15.16 | H | Me | H | Me | H | $CH_2$ | HCl salt solid mp 254-268° C. (f) |
| 15.17 | H | H | Me | Me | H | $CH_2$ | |
| 15.18 | H | H | H | Me | Me | $CH_2$ | |
| 15.19 | H | H | F | Me | H | $CH_2$ | |
| 15.20 | H | H | Cl | Cl | H | $CH_2$ | |
| 15.21 | H | H | H | H | H | O | |
| 15.22 | H | H | H | Me | H | O | HCl salt solid mp >260° C. (g) |
| 15.23 | H | H | H | F | H | O | |
| 15.24 | H | H | H | Cl | H | O | |
| 15.25 | H | H | H | Br | H | O | |
| 15.26 | H | Me | H | Me | H | O | |
| 15.27 | H | H | Me | Me | H | O | |

TABLE 15-continued

| Cpd | $R^6$ | $R^7$ | $R^8$ | $R^9$ | $R^{10}$ | A | Physical data mp/opt. rot./ appearance |
|---|---|---|---|---|---|---|---|
| 15.28 | H | H | H | Me | Me | O | |
| 15.29 | H | H | F | Me | H | O | |
| 15.30 | H | H | Cl | Cl | H | O | |
| 15.31 | Me | H | H | H | H | direct bond | |
| 15.32 | Me | H | H | Me | H | direct bond | |
| 15.33 | Me | H | H | F | H | direct bond | |
| 15.34 | Me | H | H | Cl | H | direct bond | |
| 15.35 | Me | H | H | Br | H | direct bond | |
| 15.36 | Me | Me | H | Me | H | direct bond | |
| 15.37 | Me | H | Me | Me | H | direct bond | |
| 15.38 | Me | H | H | Me | Me | direct bond | |
| 15.39 | Me | H | F | Me | H | direct bond | |
| 15.40 | Me | H | Cl | Cl | H | direct bond | |
| 15.41 | Me | H | H | H | H | $CH_2$ | |
| 15.42 | Me | H | H | Me | H | $CH_2$ | |
| 15.43 | Me | H | H | F | H | $CH_2$ | |
| 15.44 | Me | H | H | Cl | H | $CH_2$ | |
| 15.45 | Me | H | H | Br | H | $CH_2$ | |
| 15.46 | Me | Me | H | Me | H | $CH_2$ | |
| 15.47 | Me | H | Me | Me | H | $CH_2$ | |
| 15.48 | Me | H | H | Me | Me | $CH_2$ | |
| 15.49 | Me | H | F | Me | H | $CH_2$ | |
| 15.50 | Me | H | Cl | Cl | H | $CH_2$ | |
| 15.51 | Me | H | H | H | H | O | |
| 15.52 | Me | H | H | Me | H | O | |
| 15.53 | Me | H | H | F | H | O | |
| 15.54 | Me | H | H | Cl | H | O | |
| 15.55 | Me | H | H | Br | H | O | |
| 15.56 | Me | Me | H | Me | H | O | |
| 15.57 | Me | H | Me | Me | H | O | |
| 15.58 | Me | H | H | Me | Me | O | |
| 15.59 | Me | H | F | Me | H | O | |
| 15.60 | Me | H | Cl | Cl | H | O | |
| 15.61 | H | H | H | Et | H | direct bond | HCl salt solid mp >260° C. (h) |
| 15.62 | H | F | H | H | H | O | HCl salt solid (i) |
| 15.63 | H | Me | Me | H | H | O | HCl salt solid mp 241-245° C. (j) |
| 15.64 | H | H | H | OMe | H | direct bond | HCl salt solid |

Notes to references (a) to (k) in Table 15:
(a) 1H-NMR (DMSO) 8.8 (br, 3H), 7.5 (m, 1H), 7.3 (m, 1H), 7.1 (m, 1H), 4.7 (m, 1H), 3.0 (m, 1H), 2.8 (m, 1H), 2.5 (m, 1H), 2.0 (m, 1H);
(b) 7.14 (s, 1H), 6.98 (s, 1H), 4.30 (t, 1H), 2.87 (ddd, 1H), 2.72 (m, 1H), 2.45 (m, 1H), 2.25 (s, 3H), 2.24 (s, 3H), 1.62 (m, 1H);
(c) 7.03 (d, 1H), 6.99 (d, 1H), 4.50 (dd, 1H), 3.12 (m, 1H), 2.79 (ddd, 1H), 2.38 (m, 1H), 2.30 (s, 3H), 2.25 (s, 3H), 1.88 (m, 1H);
(d) 7.12 (d, 1H), 6.83 (d, 1H), 4.30 (t, 1H), 2.90 (ddd, 1H), 2.75 (m, 1H), 2.50 (m, 1H), 2.24 (s, 3H), 1.64 (m, 1H);
(e) (DMSO) 8.5 (br, 3H), 7.4 (s, 1H), 7.1 (m, 2H), 4.3 (t, 1H), 2.7 (m, 2H), 2.25 (s, 3H), 2.1-1.6 (m, 4H);
(f) (DMSO) 8.4 (br, 3H), 7.15 (s, 1H), 6.95 (s, 1H), 4.3 (br, 1H), 2.5 (m, 2H), 2.25 (s, 3H), 2.15 (s, 3H), 2.0-1.6 (m, 4H);
(g) (DMSO) 8.8 (br, 3H), 7.4 (d, 1H), 7.05 (dd, 1H), 6.75 (d, 1H), 4.4 (br, 1H), 4.2 (m, 2H), 2.25 (s, 3H), 2.3-2.0 (m, 2H);
(h) (DMSO) 8.6 (br, 3H), 7.5 (s, 1H), 7.2 (dd, 2H), 4.7 (t, 1H), 3.0 (m, 1H), 2.8 (m, 1H), 2.6 (q, 2H), 2.5 (m, 1H), 2.0 (m, 1H), 1.2 (t, 3H);
(i) (DMSO) 8.9 (br, 3H), 7.4 (d, 1H), 7.2 (m, 1H), 6.95 (m, 1H), 4.5 (t, 1H), 4.3 (m, 2H), 2.4-2.1 (m, 2H);
(j) (DMSO) 8.7 (br, 3H), 7.3 (d, 1H), 6.75 (d, 1H), 4.4 (t, 1H), 4.3 (m, 2H), 2.2 (s, 3H), 2.3-2.1 (m, 2H), 2.0 (s, 3H).

The following Table 16 illustrates the intermediate amines of the above general formula (Va) which are used to prepare the above compounds of formula (If), (If-1), (Ig), (Ig-1), (Ij), (Ij-1) and (IL).

TABLE 16

| Cpd | $R^6$ | $R^7$ | $R^8$ | $R^9$ | $R^{10}$ | A | Physical data |
|---|---|---|---|---|---|---|---|
| 16.1 | Me | H | H | H | H | direct bond | HCl salt solid (a) |
| 16.2 | Me | H | H | Me | H | direct bond | HCl salt solid (b) |
| 16.3 | Me | H | H | F | H | direct bond | |
| 16.4 | Me | H | H | Cl | H | direct bond | |
| 16.5 | Me | H | H | Br | H | direct bond | |
| 16.6 | Me | Me | H | Me | H | direct bond | |
| 16.7 | Me | H | Me | Me | H | direct bond | |
| 16.8 | Me | H | H | Me | Me | direct bond | |
| 16.9 | Me | H | F | Me | H | direct bond | |
| 16.10 | Me | H | Cl | Cl | H | direct bond | |
| 16.11 | Me | H | H | H | H | $CH_2$ | HCl salt solid mp 246-247° C. (c) |
| 16.12 | Me | H | H | Me | H | $CH_2$ | |
| 16.13 | Me | H | H | F | H | $CH_2$ | |
| 16.14 | Me | H | H | Cl | H | $CH_2$ | |
| 16.15 | Me | H | H | Br | H | $CH_2$ | |
| 16.16 | Me | Me | H | Me | H | $CH_2$ | |
| 16.17 | Me | H | Me | Me | H | $CH_2$ | |
| 16.18 | Me | H | H | Me | Me | $CH_2$ | |
| 16.19 | Me | H | F | Me | H | $CH_2$ | |
| 16.20 | Me | H | Cl | Cl | H | $CH_2$ | |
| 16.21 | Me | H | H | H | H | O | HCl salt solid |
| 16.22 | Me | H | H | Me | H | O | |
| 16.23 | Me | H | H | F | H | O | |
| 16.24 | Me | H | H | Cl | H | O | |
| 16.25 | Me | H | H | Br | H | O | |
| 16.26 | Me | Me | H | Me | H | O | |
| 16.27 | Me | H | Me | Me | H | O | |
| 16.28 | Me | H | H | Me | Me | O | |
| 16.29 | Me | H | F | Me | H | O | |
| 16.30 | Me | H | Cl | Cl | H | O | |

Notes to references (a) to (c) in Table 16:
(a) (DMSO) 8.8 (br, 3H), 7.7 (d, 1H), 7.3 (m, 3H), 4.3 (br, 1H), 3.2 (m, 1H), 2.5 (m, 2H), 1.2 (d, 3H);
(b) (DMSO) 8.8 (br, 3H), 7.4 (s, 1H), 7.15 (m, 2H), 4.2 (br, 1H), 3.2 (m, 1H), 2.5 (m, 2H), 2.3 (s, 3H), 1.2 (d, 3H);
(c) (DMSO) 8.5 (br, 3H), 7.6 (dd, 1H), 7.2 (m, 3H), 4.1 (br, 1H), 2.8 (m, 1H), 2.2 (m, 1H), 2.0 (m, 1H), 1.5 (m, 1H), 1.1 (d, 3H).

The following Table 17 illustrates the intermediate amines of the above general formula (Vb) which are used to prepare the above compounds of formula (Ih), (Ih-1), (Ii), (Ii-1) and (Im).

TABLE 17

| Cpd | $R^6$ | $R^7$ | $R^8$ | $R^9$ | $R^{10}$ | A | Physical data |
|---|---|---|---|---|---|---|---|
| 17.1 | Me | H | H | H | H | direct bond | HCl salt solid mp 245-260° C. |
| 17.2 | Me | H | H | Me | H | direct bond | |
| 17.3 | Me | H | H | F | H | direct bond | |
| 17.4 | Me | H | H | Cl | H | direct bond | |
| 17.5 | Me | H | H | Br | H | direct bond | |
| 17.6 | Me | Me | H | Me | H | direct bond | |
| 17.7 | Me | H | Me | Me | H | direct bond | |
| 17.8 | Me | H | H | Me | Me | direct bond | |
| 17.9 | Me | H | F | Me | H | direct bond | |
| 17.10 | Me | H | Cl | Cl | H | direct bond | |
| 17.11 | Me | H | H | H | H | $CH_2$ | |
| 17.12 | Me | H | H | Me | H | $CH_2$ | |
| 17.13 | Me | H | H | F | H | $CH_2$ | |
| 17.14 | Me | H | H | Cl | H | $CH_2$ | |
| 17.15 | Me | H | H | Br | H | $CH_2$ | |
| 17.16 | Me | Me | H | Me | H | $CH_2$ | |
| 17.17 | Me | H | Me | Me | H | $CH_2$ | |
| 17.18 | Me | H | H | Me | Me | $CH_2$ | |
| 17.19 | Me | H | F | Me | H | $CH_2$ | |
| 17.20 | Me | H | Cl | Cl | H | $CH_2$ | |
| 17.21 | Me | H | H | H | H | O | |
| 17.22 | Me | H | H | Me | H | O | |
| 17.23 | Me | H | H | F | H | O | |
| 17.24 | Me | H | H | Cl | H | O | |
| 17.25 | Me | H | H | Br | H | O | |
| 17.26 | Me | Me | H | Me | H | O | |
| 17.27 | Me | H | Me | Me | H | O | |
| 17.28 | Me | H | H | Me | Me | O | |
| 17.29 | Me | H | F | Me | H | O | |
| 17.30 | Me | H | Cl | Cl | H | O | |

Tables 18 and 19: Compounds of Formula (XIII)

TABLES 18 and 19

Compounds of formula (XIII)

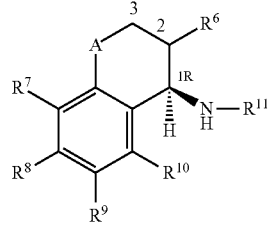

(XIII)

in which $R^{11}$ is chloroacetyl [compounds no. 18.1 to 18.63] or methoxyacetyl [compounds no. 19.1 to 19.63] and in case of compounds in which $R^6$ is methyl, the configuration at the carbon atom marked 2 is racemic i.e. (2RS).

| Cpd | Cpd | $R^6$ | $R^7$ | $R^8$ | $R^9$ | $R^{10}$ | A | Physical data mp/opt. rot./ appearance |
|---|---|---|---|---|---|---|---|---|
| 18.1 | 19.1 | H | H | H | H | H | direct bond | |
| 18.2 | 19.2 | H | H | H | Me | H | direct bond | |
| 18.3 | 19.3 | H | H | H | F | H | direct bond | |
| 18.4 | 19.4 | H | H | H | Cl | H | direct bond | |
| 18.5 | 19.5 | H | H | H | Br | H | direct bond | |
| 18.6 | 19.6 | H | Me | H | Me | H | direct bond | |
| 18.7 | 19.7 | H | H | Me | Me | H | direct bond | |
| 18.8 | 19.8 | H | H | H | Me | Me | direct bond | |
| 18.9 | 19.9 | H | H | F | Me | H | direct bond | |
| 18.10 | 19.10 | H | H | Cl | Cl | H | direct bond | |
| 18.11 | 19.11 | H | H | H | H | H | $CH_2$ | |
| 18.12 | 19.12 | H | H | H | Me | H | $CH_2$ | |
| 18.13 | 19.13 | H | H | H | F | H | $CH_2$ | |
| 18.14 | 19.14 | H | H | H | Cl | H | $CH_2$ | |
| 18.15 | 19.15 | H | H | H | Br | H | $CH_2$ | |
| 18.16 | 19.16 | H | Me | H | Me | H | $CH_2$ | |
| 18.17 | 19.17 | H | H | Me | Me | H | $CH_2$ | |
| 18.18 | 19.18 | H | H | H | Me | Me | $CH_2$ | |
| 18.19 | 19.19 | H | H | F | Me | H | $CH_2$ | |
| 18.20 | 19.20 | H | H | Cl | Cl | H | $CH_2$ | |
| 18.21 | 19.21 | H | H | H | H | H | O | |
| 18.22 | 19.22 | H | H | H | Me | H | O | |
| 18.23 | 19.23 | H | H | H | F | H | O | |
| 18.24 | 19.24 | H | H | H | Cl | H | O | |
| 18.25 | 19.25 | H | H | H | Br | H | O | |
| 18.26 | 19.26 | H | Me | H | Me | H | O | |
| 18.27 | 19.27 | H | H | Me | Me | H | O | |
| 18.28 | 19.28 | H | H | H | Me | Me | O | |
| 18.29 | 19.29 | H | H | F | Me | H | O | |
| 18.30 | 19.30 | H | H | Cl | Cl | H | O | |
| 18.31 | 19.31 | Me | H | H | H | H | direct bond | |
| 18.32 | 19.32 | Me | H | H | Me | H | direct bond | |
| 18.33 | 19.33 | Me | H | H | F | H | direct bond | |
| 18.34 | 19.34 | Me | H | H | Cl | H | direct bond | |
| 18.35 | 19.35 | Me | H | H | Br | H | direct bond | |
| 18.36 | 19.36 | Me | Me | H | Me | H | direct bond | |
| 18.37 | 19.37 | Me | H | Me | Me | H | direct bond | |
| 18.38 | 19.38 | Me | H | H | Me | Me | direct bond | |
| 18.39 | 19.39 | Me | H | F | Me | H | direct bond | |
| 18.40 | 19.40 | Me | H | Cl | Cl | H | direct bond | |
| 18.41 | 19.41 | Me | H | H | H | H | $CH_2$ | |
| 18.42 | 19.42 | Me | H | H | Me | H | $CH_2$ | |
| 18.43 | 19.43 | Me | H | H | F | H | $CH_2$ | |
| 18.44 | 19.44 | Me | H | H | Cl | H | $CH_2$ | |
| 18.45 | 19.45 | Me | H | H | Br | H | $CH_2$ | |
| 18.46 | 19.46 | Me | Me | H | Me | H | $CH_2$ | |
| 18.47 | 19.47 | Me | H | Me | Me | H | $CH_2$ | |
| 18.48 | 19.48 | Me | H | H | Me | Me | $CH_2$ | |
| 18.49 | 19.49 | Me | H | F | Me | H | $CH_2$ | |
| 18.50 | 19.50 | Me | H | Cl | Cl | H | $CH_2$ | |
| 18.51 | 19.51 | Me | H | H | H | H | O | |
| 18.52 | 19.52 | Me | H | H | Me | H | O | |
| 18.53 | 19.53 | Me | H | H | F | H | O | |
| 18.54 | 19.54 | Me | H | H | Cl | H | O | |
| 18.55 | 19.55 | Me | H | H | Br | H | O | |
| 18.56 | 19.56 | Me | Me | H | Me | H | O | |
| 18.57 | 19.57 | Me | H | Me | Me | H | O | |
| 18.58 | 19.58 | Me | H | H | Me | Me | O | |
| 18.59 | 19.59 | Me | H | F | Me | H | O | |
| 18.60 | 19.60 | Me | H | Cl | Cl | H | O | |
| 18.61 | 19.61 | H | H | H | Et | H | direct bond | |
| 18.62 | 19.62 | H | F | H | H | H | O | |
| 18.63 | 19.63 | H | Me | Me | H | H | O | |

TABLES 18 and 19-continued

Compounds of formula (XIII)

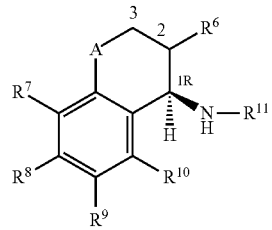

(XIII)

in which $R^{11}$ is chloroacetyl [compounds no. 18.1 to 18.63] or methoxyacetyl [compounds no. 19.1 to 19.63] and in case of compounds in which $R^6$ is methyl, the configuration at the carbon atom marked 2 is racemic i.e. (2RS).

Tables 20 and 21: Compounds of Formula (XIIIa)

TABLES 20 and 21

Compounds of formula (XIIIa)

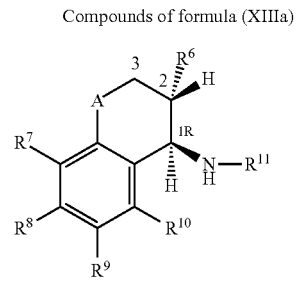

(XIIIa)

in which $R^{11}$ is chloroacetyl [compounds no. 20.1 to 20.30] or methoxyacetyl [compounds no. 21.1 to 21.30]

| Cpd | Cpd | $R^6$ | $R^7$ | $R^8$ | $R^9$ | $R^{10}$ | A | Physical data |
|---|---|---|---|---|---|---|---|---|
| 20.1 | 21.1 | Me | H | H | H | H | direct bond | |
| 20.2 | 21.2 | Me | H | H | Me | H | direct bond | |
| 20.3 | 21.3 | Me | H | H | F | H | direct bond | |
| 20.4 | 21.4 | Me | H | H | Cl | H | direct bond | |
| 20.5 | 21.5 | Me | H | H | Br | H | direct bond | |
| 20.6 | 21.6 | Me | Me | H | Me | H | direct bond | |
| 20.7 | 21.7 | Me | H | Me | Me | H | direct bond | |
| 20.8 | 21.8 | Me | H | H | Me | Me | direct bond | |
| 20.9 | 21.9 | Me | H | F | Me | H | direct bond | |
| 20.10 | 21.10 | Me | H | Cl | Cl | H | direct bond | |
| 20.11 | 21.11 | Me | H | H | H | H | $CH_2$ | |
| 20.12 | 21.12 | Me | H | H | Me | H | $CH_2$ | |
| 20.13 | 21.13 | Me | H | H | F | H | $CH_2$ | |
| 20.14 | 21.14 | Me | H | H | Cl | H | $CH_2$ | |
| 20.15 | 21.15 | Me | H | H | Br | H | $CH_2$ | |
| 20.16 | 21.16 | Me | Me | H | Me | H | $CH_2$ | |
| 20.17 | 21.17 | Me | H | Me | Me | H | $CH_2$ | |
| 20.18 | 21.18 | Me | H | H | Me | Me | $CH_2$ | |
| 20.19 | 21.19 | Me | H | F | Me | H | $CH_2$ | |
| 20.20 | 21.20 | Me | H | Cl | Cl | H | $CH_2$ | |
| 20.21 | 21.21 | Me | H | H | H | H | O | |
| 20.22 | 21.22 | Me | H | H | Me | H | O | |

TABLES 20 and 21-continued

Compounds of formula (XIIIa)

in which $R^{11}$ is chloroacetyl [compounds no. 20.1 to 20.30] or methoxyacetyl [compounds no. 21.1 to 21.30]

| Cpd | Cpd | $R^6$ | $R^7$ | $R^8$ | $R^9$ | $R^{10}$ | A | Physical data |
|---|---|---|---|---|---|---|---|---|
| 20.23 | 21.23 | Me | H | H | F | H | O | |
| 20.24 | 21.24 | Me | H | H | Cl | H | O | |
| 20.25 | 21.25 | Me | H | H | Br | H | O | |
| 20.26 | 21.26 | Me | Me | H | Me | H | O | |
| 20.27 | 21.27 | Me | H | Me | Me | H | O | |
| 20.28 | 21.28 | Me | H | H | Me | Me | O | |
| 20.29 | 21.29 | Me | H | F | Me | H | O | |
| 20.30 | 21.30 | Me | H | Cl | Cl | H | O | |

Tables 22 and 23: Compounds of Formula (XIIIb)

TABLES 22 and 23

Compounds of formula (XIIIb)

in which $R^{11}$ is chloroacetyl [compounds no. 22.1 to 22.30] or methoxyacetyl [compounds no. 23.1 to 23.30]

| Cpd | Cpd | $R^6$ | $R^7$ | $R^8$ | $R^9$ | $R^{10}$ | A | Physical data |
|---|---|---|---|---|---|---|---|---|
| 22.1 | 23.1 | Me | H | H | H | H | direct bond | |
| 22.2 | 23.2 | Me | H | H | Me | H | direct bond | |
| 22.3 | 23.3 | Me | H | H | F | H | direct bond | |
| 22.4 | 23.4 | Me | H | H | Cl | H | direct bond | |
| 22.5 | 23.5 | Me | H | H | Br | H | direct bond | |
| 22.6 | 23.6 | Me | Me | H | Me | H | direct bond | |
| 22.7 | 23.7 | Me | H | Me | Me | H | direct bond | |
| 22.8 | 23.8 | Me | H | H | Me | Me | direct bond | |
| 22.9 | 23.9 | Me | H | F | Me | H | direct bond | |
| 22.10 | 23.10 | Me | H | Cl | Cl | H | direct bond | |
| 22.11 | 23.11 | Me | H | H | H | H | $CH_2$ | |
| 22.12 | 23.12 | Me | H | H | Me | H | $CH_2$ | |
| 22.13 | 23.13 | Me | H | H | F | H | $CH_2$ | |
| 22.14 | 23.14 | Me | H | H | Cl | H | $CH_2$ | |
| 22.15 | 23.15 | Me | H | H | Br | H | $CH_2$ | |
| 22.16 | 23.16 | Me | Me | H | Me | H | $CH_2$ | |
| 22.17 | 23.17 | Me | H | Me | Me | H | $CH_2$ | |
| 22.18 | 23.18 | Me | H | H | Me | Me | $CH_2$ | |
| 22.19 | 23.19 | Me | H | F | Me | H | $CH_2$ | |
| 22.20 | 23.20 | Me | H | Cl | Cl | H | $CH_2$ | |
| 22.21 | 23.21 | Me | H | H | H | H | O | |
| 22.22 | 23.22 | Me | H | H | Me | H | O | |
| 22.23 | 23.23 | Me | H | H | F | H | O | |
| 22.24 | 23.24 | Me | H | H | Cl | H | O | |
| 22.25 | 23.25 | Me | H | H | Br | H | O | |
| 22.26 | 23.26 | Me | Me | H | Me | H | O | |
| 22.27 | 23.27 | Me | H | Me | Me | H | O | |
| 22.28 | 23.28 | Me | H | H | Me | Me | O | |
| 22.29 | 23.29 | Me | H | F | Me | H | O | |
| 20.30 | 23.30 | Me | H | Cl | Cl | H | O | |

According to a further feature of the present invention, there is provided the use as a herbicide or plant growth regulator characterised in that the compound of formula (I) or a salt thereof is applied in an effective amount for the control of weeds or for regulating the growth of plants at a plant locus. For this purpose, the said compound is normally used in the form of a herbicidal composition (i.e. in association with compatible diluents or carriers and/or surface active agents suitable for use in herbicidal compositions), for example as hereinafter described.

By application to the 'plant locus' is meant application, for example to the plant growing medium, such as soil, as well as to the seeds, emerging seedlings, roots, stems, leaves or other plant parts.

The compounds of the formula (I) and their salts, all termed hereinbelow as compounds of formula (I), have an excellent herbicidal activity against a broad range of economically important monocotyledonous and dicotyledonous harmful plants. The compounds of formula (I) also act efficiently on perennial weeds which produce shoots from rhizomes, root stocks or other perennial organs and which are difficult to control. In this context, the substances can be applied preplanting, pre-emergence or post-emergence.

Specifically, examples may be mentioned of some representatives of the monocotyledonous and dicotyledonous weed flora which can be controlled by the compounds of formula (I), without the enumeration being a restriction to certain species.

Amongst the monocotyledonous weed species, those on which the active substances act efficiently are, for example, Agrostis, Alopecurus, Apera, Avena, Brachicaria, Bromus, Dactyloctenium, Digitaria, Echinochloa, Eleocharis, Eleusine, Festuca, Fimbristylis, Ischaemum, Lolium, Monochoria, Panicum, Paspalum, Phalaris, Phleum, Poa, Sagittaria, Scirpus, Setaria, Sphenoclea and Cyperus species from the annual group and, amongst the perennial species, Agropyron, Cynodon, Imperata and Sorghum and also perennial Cyperus species.

In the case of dicotyledonous weed species, the spectrum of action extends to species such as, for example, Galium, Viola, Veronica, Lamium, Stellaria, Amaranthus, Sinapis, Ipomoea, Matricaria, Abutilon and Sida amongst the annuals and Convolvulus, Cirsium, Rumex and Artemisia in the case of the perennial weeds.

Herbicidal action is also achieved in the case of dicotyledonous harmful plants such as Ambrosia, Anthemis, Carduus, Centaurea, Chenopodium, Datura, Emex, Galeopsis, Galinsoga, Kochia, Lepidium, Lindernia, Papaver, Portlaca, Polygonum, Ranunculus, Rorippa, Rotala, Seneceio, Sesbania, Solanum, Sonchus, Taraxacum, Trifolium, Urtica and Xanthium.

Harmful plants occurring under the specific cultivation conditions of rice, such as, for example, Sagittaria, Alisma, Eleocharis, Scirpus and Cyperus, are also well controlled by the active substances according to the invention.

If the compounds according to the invention are applied to the soil surface before germination (pre-emergence of the weeds), then the weed seedlings are either prevented completely from emerging or the weeds grow until they have reached the cotyledon stage, but then their growth stops and they finally die completely after three to four weeks have elapsed.

When the active substances are applied post-emergence to the green parts of the plants, growth stops equally drastically a very short time after treatment and the weed plants remain at the stage of growth at the time of application, or they die completely after a certain time, so that in this manner competition by the weeds, which is harmful to the crop plants, is eliminated at a very early stage and in a sustained manner.

Although the compounds according to the invention have an excellent herbicidal activity against mono- and dicotyledonous weeds, some crop plants of economically important crops such as, for example, wheat, barley, rye, triticale, rice, maize, sugar beet, cotton or soybeans (particularly wheat, barley, rice or maize) are damaged only to an insignificant extent or not at all, if an appropriate dosage is applied. For these reasons, the present compounds are in some cases suitable for the selective control of undesired vegetation in stands of agriculturally useful plants or in stands of ornamental plants.

The activity allows to employ the compounds as effective herbicidal active ingredients pre- and post-emergence for controlling broad-leaved weeds and grass weeds at relatively low dosage as a selective herbicide in some crops (preferably pre-emergence of the weeds in many cases). Alternatively the compounds can be used effectively at some higher dosage for the control of a broad range of dicotyledonous weeds and monocotyledonous weeds in plantation crops and on uncultivated land and, by means of specific application techniques, also for inter-row treatment in agricultural row crops such as maize, cotton and the like.

The compositions according to the invention can be used to selectively control annual and perennial harmful plants in plantation crops such as oil palm, coconut palm, India-rubber tree, citrus, pineapples, pome, cotton, coffee, cocoa and the like, as well as in fruit production and viticulture. Equally, the combinations according to the invention can be employed in arable crop production using the no-till or zero-till method.

Another object of the invention is thus the selective weed control in plantation crops by applying the compounds according to the invention as herbicides.

Alternatively, they can be used as very effective herbicides in a non-selective manner on paths, open spaces and industrial sites and the like to keep these areas free from undesirable vegetation.

The herbicidal compositions according to the invention are distinguished by a long-term herbicidal action with a rapid onset.

It is also possible to use the compounds (I) in combination with other pesticidally active substances or nutrients, such as, for example, insecticides, acaricides, herbicides, fungicides, safeners, fertilizers and/or growth regulators.

The invention thus also relates to a method of controlling undesirable vegetation which comprises applying one or more type A herbicides together with one or more type B herbicides and a type C surfactant to the harmful plants, parts of these plants or the area under cultivation. Type A herbicides are the compounds of formula (I) or their salts; type B herbicides are other herbicides useful to be combined with compounds (I) for the purpose of broadening weed spectrum to be controlled, or increasing herbicidal effect (some possible type B herbicides are mentioned further below).

In addition, the substances according to the invention have outstanding growth-regulatory properties in crop plants. They engage in the plants' metabolism in a regulatory fashion and can thus be employed for influencing plant constituents in a targeted fashion and for facilitating harvesting, such as, for example, by triggering desiccation and stunted growth. Moreover, they are also suitable for generally controlling and inhibiting undesired vegetative growth without simultaneously killing the plants. Inhibiting vegetative growth plays an important role in many monocotyledonous and dicotyledonous crops since lodging can be reduced, or prevented completely, hereby.

Due to their herbicidal and plant-growth regulatory properties, the compounds of formula (I) can also be employed for controlling harmful plants in crops of known genetically modified plants, or genetically modified plants yet to be developed. As a rule, the transgenic plants are distinguished by particular advantageous properties, for example by resistances to certain pesticides, mainly certain herbicides, resistances to plant diseases or pathogens of plant diseases, such as certain insects or microorganisms such as fungi, bacteria or viruses. Other particular properties relate, for example, to the harvested material with regard to quantity, quality, storage properties, composition and specific constituents. Thus, transgenic plants are known where the starch content is increased or the starch quality is altered or those where the harvested material has a different fatty acid spectrum.

The compounds of formula (I) are preferably employed in economically important transgenic crops of useful plants and ornamentals, for example cereals such as wheat, barley, rye, oats, sorghum and millet, rice, cassava and maize, or else crops of sugar beet, cotton, soya, oil seed rape, potatoes, tomatoes, peas and other vegetables. The compounds of formula (I) can preferably be employed as herbicides in crops of useful plants which are resistant to the phytotoxic effects of the herbicides or have been rendered thus by means of genetic engineering.

Traditional ways of generating novel plants which have modified characteristics in comparison with existing plants consist, for example, in traditional breeding methods and the generation of mutants. However, it is also possible to generate novel plants with altered characteristics with the aid of genetic engineering methods (see, for example, EP-A-0221044, EP-A-0131624). For example, several cases have been described of genetic engineering modifications of crop plants with the purpose of modifying the starch synthesized in the plants (for example WO 92/11376, WO 92/14827, WO 91/19806), transgenic crop plants which are resistant to certain herbicides of the glufosinate type (cf., for example, EP-A-0242236, EP-A-242246) or the glyphosate type (WO 92/00377) or the sulfonylurea type (EP-A-0257993, U.S. Pat. No. 5,013,659), transgenic crop plants, for example cotton, which are capable of producing *Bacillus thuringiensis* toxins (Bt toxins) which make the plants resistant to specific pests (EP-A-0142924, EP-A-0193259), transgenic crop plants whose fatty acid spectrum is modified (WO 91/13972).

A large number of techniques in molecular biology by means of which novel transgenic plants with altered characteristics can be generated are known in principle; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Klone" [Genes and Clones], VCH Weinheim 2nd Edition 1996, or Christou, "Trends in Plant Science" 1 (1996) 423-431).

In order to perform such genetic engineering manipulations, nucleic acid molecules may be introduced into plasmids which allow mutagenesis or a sequence change by means of recombination of DNA sequences. It is possible, for example, with the aid of the abovementioned standard methods to perform base exchanges, to remove subsequences or to add natural or synthetic sequences. To connect the DNA fragments to each other, adaptors or linkers may be attached to the fragments.

For example, plant cells with a reduced activity of a gene product can be generated by expressing at least one corresponding antisense RNA, a sense RNA to achieve a cosuppressory effect or by expressing at least one ribozyme of suitable construction which specifically cleaves transcripts of the abovementioned gene product.

To this end it is possible to make use of, on the one hand, DNA molecules which encompass the entire coding sequence of a gene product inclusive of any flanking sequences which may be present, on the other hand DNA molecules which only encompass parts of the coding sequence, but these parts must be long enough in order to effect, in the cells, an antisense effect. Use may also be made of DNA sequences which show a high degree of homology to the coding sequences of a gene product, but which are not completely identical.

When nucleic acid molecules are expressed in plants, the protein which has been synthesized may be located in any desired compartment of the plant cell. However, to achieve localization in a particular compartment, it is possible, for example, to link the coding region with DNA sequences which guarantee localization in a particular compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells may be regenerated by known techniques to give complete plants. In principle, the transgenic plants can be plants of any desired plant species, that is to say monocotyledonous and also dicotyledonous plants.

This allows transgenic plants to be obtained which exhibit altered characteristics by means of overexpression, suppression or inhibition of homologous (=natural) genes or gene sequences or by means of expression of heterologous (=foreign) genes or gene sequences.

The compounds of formula (I) can preferably be employed in transgenic crops which are resistant to herbicides from the group of the sulfonylureas, glufosinate-ammonium or glyphosate-isopropylammonium and analogous active substances.

When the compounds of formula (I) are used in transgenic crops, effects other than the herbicidal effects to be observed in other crops are frequently found which are specific for application in the particular transgenic crop, for example an altered or specifically widened weed spectrum which can be controlled, altered application rates which may be employed for application, preferably good combining ability with the herbicides to which the transgenic crop is resistant, and an effect on growth and yield of the transgenic crop plants.

The invention therefore also relates to the use of the compounds of formula (I) as herbicides for controlling harmful plants in transgenic crop plants.

The use according to the invention for controlling harmful plants or for regulating the growth of plants also includes the case where the compounds of formula (I) are only formed in the plant or the soil from a precursor ("prodrug") after its application to the plant.

The compounds of formula (I) can be employed in the conventional preparations as wettable powders, emulsifiable concentrates, sprayable solutions, dusts or granules. The invention therefore also relates to herbicidal and plant-growth-regulating compositions which comprise compounds of formula (I).

According to a further feature of the present invention, there is provided a herbicidal or plant growth regulating composition comprising an effective amount of a compound of formula (I) as defined above or an agriculturally acceptable salt thereof, in association with, and preferably homogeneously dispersed in, one or more compatible agriculturally-acceptable diluents or carriers and/or surface active agents [i.e. diluents or carriers and/or surface active agents of the type generally accepted in the art as being suitable for use in herbicidal compositions and which are compatible with compounds of the invention]. The term "homogeneously dispersed" is used to include compositions in which the compounds of formula (I) are dissolved in other components. The term "herbicidal compositions" is used in a broad sense to include not only compositions which are ready for use as herbicides but also concentrates which must be diluted before use (including tank mixtures).

The compounds of formula (I) can be formulated in various ways, depending on the prevailing biological and/or chemico-physical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and described, for example, in: Winnacker-Küchler, "Chemische Technologie" [Chemical Technology], Volume 7, C. Hauser Verlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag, Munich, 4th Ed. 1986.

Based on these formulations, it is also possible to prepare combinations with other pesticidally active substances such as, for example, insecticides, acaricides, herbicides, fungicides, and with safeners, fertilizers and/or growth regulators, for example in the form of a readymix or a tank mix.

Wettable powders are preparations which are uniformly dispersible in water and which, besides the compounds of formula (I), also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the compounds of formula (I) are, for example, ground finely in conventional apparatuses such as hammer mills, blower mills and air-jet mills and mixed with the formulation auxiliaries, either concomitantly or thereafter.

Emulsifiable concentrates are prepared, for example, by dissolving the compounds of formula (I) in an organic solvent, for example butanol, cyclohexanone, dimethylformamide, xylene or else higher-boiling aromatics or hydrocarbons or mixtures of these, with addition of one or more ionic and/or nonionic surfactants (emulsifiers). Emulsifiers which can be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters or polyoxyethylene sorbitan esters such as polyoxyethylene sorbitan fatty acid esters.

Dusts are obtained by grinding the active substance with finely divided solid substances, for example talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as they have already been mentioned above for example in the case of the other formulation types.

Granules can be prepared either by spraying the compounds of formula (I) onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57.

For further details on the formulation of crop protection products, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations comprise 0.1 to 99% by weight, in particular 0.1 to 95% by weight, of compounds of formula (I).

The concentration of compounds of formula (I) in wettable powders is, for example, approximately 10 to 90% by weight, the remainder to 100% by weight being composed of customary formulation components. In the case of emulsifiable concentrates, the concentration of compounds of formula (I) can amount to approximately 1 to 90, preferably 5 to 80% by weight. Formulations in the form of dusts usually comprise 1 to 30% by weight of compounds of formula (I), preferably in most cases 5 to 20% by weight of compounds of formula (I), while sprayable solutions comprise approximately 0.05 to 80, preferably 2 to 50% by weight of compounds of formula (I). In the case of water-dispersible granules, the content of compounds of formula (I) depends partly on whether the compounds of formula (I) are in liquid or solid form and on which granulation auxiliaries, fillers and the like are being used. The water-dispersible granules, for example, comprise between 1 and 95% by weight of active substance, preferably between 10 and 80% by weight.

In addition, the formulations of compounds of formula (I) mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

The compounds of the formula (I) or their salts can be employed as such or in the form of their preparations (formulations) as combinations with other pesticidally active substances, such as, for example, insecticides, acaricides, nematicides, herbicides, fungicides, safeners, fertilizers and/or growth regulators, for example as a premix or as tank mixes.

Components which may be employed for the active substances according to the invention in mixed formulations or in tank mix are, for example, known active compounds which are based on an inhibition of, for example, acetolactate synthase, acetyl-coenzyme A carboxylase, PS I, PS II, HPPDO, phytoene desaturase, protoporphyrinogen oxidase, glutamine synthetase, cellulose biosynthesis, 5-enolpyruvylshikimate-3-phosphate synthetase. Such compounds, and also other compounds which can be employed, whose mechanism of action is to a degree unknown or different, are described, for example, in Weed Research 26, 441-445 (1986), or "The Pesticide Manual", 12th Edition 2000 (hereinbelow also abbreviated to "PM"), The British Crop Protection Council and the Royal Soc. of Chemistry (editors), including the e-Pesticide Manual Version 2.2 (2002), and literature cited therein. Herbicides which are known from the literature and which can be mentioned, which can be combined with the compounds of the formula (I), are, for example, the following active substances (Note: the compounds are either designated by the common name according to the International Organization for Standardization (ISO) or using the chemical name, if appropriate together with a customary code number); compounds having common names are also referred to in the "Compendium of Pesticide Common Names" available from the Internet, and the literature cited therein: acetochlor; acifluorfen(-sodium); aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim(-sodium); ametryn; amicarbazone, amidochlor, amidosulfuron; amitrol; AMS, i.e. ammonium sulfamate; anilofos; asulam; atrazine; azafenidin; azimsulfuron (DPX-A8947); aziprotryn; barban; BAS 516H, i.e. 5-fluoro-2-phenyl-4H-3,1-benzoxazin-4-one; beflubutamid; benazolin(-ethyl); benfluralin; benfuresate; bensulfuron(-methyl); bensulide; bentazone(-sodium); benzobicyclone; benzofenap; benzofluor; benzoylprop(-ethyl); benzthiazuron; bialaphos (bilanafos); bifenox; bispyribac(-sodium); bromacil; bromobutide; bromofenoxim; bromoxynil; bromuron; buminafos; busoxinone; butachlor; butafenacil; butamifos; butenachlor; buthidazole; butralin; butroxydim; butylate; cafenstrole (CH-900); carbetamide; carfentrazone(-ethyl); caloxydim, CDAA, i.e. 2-chloro-N,N-di-2-propenylacetamide; CDEC, i.e. 2-chloroallyl diethyldithiocarbamate; chlomethoxyfen; chloramben; chlorazifop-butyl; chlorbromuron; chlorbufam; chlorfenac; chlorflurenol-methyl; chloridazon; chlorimuron(-ethyl); chlornitrofen; chlorotoluron; chloroxuron; chlorpropham; chlorsulfuron; chlorthal-dimethyl; chlorthiamid; chlortoluron, cinidon(-methyl or -ethyl), cinmethylin; cinosulfuron; clethodim; clefoxydim, clodinafop and its ester derivatives (for example clodinafop-propargyl); clomazone; clomeprop; cloproxydim; clopyralid; clopyrasulfuron(-methyl); cloransulam(-methyl); cumyluron (JC 940); cyanazine; cycloate; cyclosulfamuron (AC 104); cycloxydim; cycluron; cyhalofop and its ester derivatives (for example butyl-ester, DEH-112); cyperquat; cyprazine; cyprazole; daimuron; 2,4-D; 2,4-DB; dalapon; dazomet, desmedipham; desmetryn; di-allate; dicamba; dichlobenil; dichlorprop(-P); diclofop and its esters such as diclofop-methyl; diclosulam, diethatyl(-ethyl); difenoxuron; difenzoquat; diflufenican; diflufenzopyr; dimefuron; dimepiperate; dimethachlor; dimethametryn; dimethenamid (SAN-582H); dimethenamid(-P); dimethazone, dimethipin; dimexyflam, dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; epoprodan, EPTC; esprocarb; ethalfluralin; ethametsulfuron-methyl; ethidimuron; ethiozin; ethofumesate; ethoxyfen and its esters (for example ethyl ester, HC-252), ethoxysulfuron, etobenzanid (HW 52); F5231, i.e. N-[2-chloro-4-fluoro-5-[4-(3-fluoropropyl)-4,5-dihydro-5-oxo-1H-tetrazol-1-yl]-phenyl] ethanesulfonamide; fenoprop; fenoxan, fenoxaprop and fenoxaprop-P and their esters, for example fenoxaprop-P-ethyl and fenoxaprop-ethyl; fenoxydim; fentrazamide; fenuron; flamprop(-methyl or -isopropyl or -isopropyl-L); flazasulfuron; florasulam; fluazifop and fluazifop-P and their esters, for example fluazifop-butyl and fluazifop-P-butyl; fluazolate, flucarbazone(-sodium); fluchloralin; flufenacet (FOE 5043), flufenpyr, flumetsulam; flumeturon; flumiclorac(-pentyl); flumioxazin (S-482); flumipropyn; fluometuron; fluorochloridone, fluorodifen; fluoroglycofen(-ethyl); flupoxam (KNW-739); flupropacil (UBIC-4243); fluproanate, flupyrsulfuron(-methyl, or -sodium); flurenol(-butyl); fluridone; flurochloridone; fluroxypyr(-meptyl); flurprimidol, flurtamone; fluthiacet(-methyl); fluthiamide (also known as flufenacet); fomesafen; foramsulfuron; fosamine; furilazole (MON 13900), furyloxyfen; glufosinate(-ammonium); glyphosate(-isopropylammonium); halosafen; halosulfuron(-methyl) and its esters (for example the methyl ester, NC-319); haloxyfop and its esters; haloxyfop-P (=R-haloxyfop) and its esters; HC-252 (diphenylether), hexazinone; imazamethabenz(-methyl); imazamethapyr; imazamox; imazapic, imazapyr; imazaquin and salts such as the ammonium salts; imazethamethapyr; imazethapyr, imazosulfuron; indanofan; iodosulfuron-(methyl)-(sodium), ioxynil; isocarbamid; isopropalin; isoproturon; isouron; isoxaben; isoxachlortole; isoxaflutole; isoxapyrifop; karbutilate; lactofen; lenacil; linuron; MCPA; MCPB; mecoprop; mefenacet; mefluidid; mesosulfuron(-methyl); mesotrione; metam, metamifop, metamitron; metazachlor; methabenzthiazuron; methazole; methoxyphenone; methyldymron; metobenzuron, metobromuron; (S-)metolachlor; metosulam (XRD 511); metoxuron; metribuzin; metsulfuron-methyl; MK-616; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethylyphenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen, norflurazon; orbencarb; oryzalin; oxadiargyl (RP-020630); oxadiazone; oxasulfuron; oxaziclomefone; oxyfluorfen; paraquat; pebulate; pelargonic acid; pendimethalin; penoxulam; pentanochlor, pentoxazone; perfluidone; pethoxamid, phenisopham; phenmedipham; picloram; picolinafen; piperophos; piributicarb; pirifenop-butyl; pretilachlor; primisulfuron(-methyl); procarbazone(-sodium); procyazine; prodiamine; profluazole, profluralin; proglinazine(-ethyl); prometon; prometryn; propachlor; propanil; propaquizafop; propazine; propham; propisochlor; propoxycarbazone(-sodium), propyzamide; prosulfalin; prosulfocarb; prosulfuron (CGA-152005); prynachlor; pyraclonil, pyraflufen(-ethyl); pyrazolinate; pyrazon; pyrazosulfuron(-ethyl); pyrazoxyfen; pyribenzoxim; pyributicarb; pyridafol; pyridate; pyriftalid, pyrimidobac(-methyl); pyrithiobac(-sodium) (K1H-2031); pyroxofop and its esters (for example propargyl ester); quinclorac; quinmerac; quinoclamine, quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulcotrione; sulfentrazone (FMC-97285, F-6285); sulfazuron; sulfometuron(-methyl); sulfosate (ICI-A0224); sulfosulfuron; TCA; tebutam (GCP-5544); tebuthiuron; tepraloxydim; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiafluamide; thiazafluron; thiazopyr (Mon-13200); thidiazimin (SN-24085); thifensulfuron(-methyl); thiobencarb; tiocarbazil; tralkoxydim; tri-allate; triasulfuron; triaziflam; triazofenamide; tribenuron(-methyl); 2,3,6-trichlorobenzoic acid (2,3,6-TBA), triclopyr; tridiphane; trietazine; trifloxysulfuron(sodium), trifluralin; triflusulfuron and esters (e.g. methyl ester, DPX-66037); trimeturon; tritosulfuron; tsitodef; vemolate; WL 110547, i.e. 5-phenoxy-1-[3-(trifluoromethyl)phenyl]-1H-tetrazole; UBH-509; D489; LS 82-556; KPP-300; NC-324; NC-330; KH-218; DPX—N8189; SC-0774; DOWCO-535; DK-8910; V-53482; PP-600; MBH-001; K1H-9201; ET-751; K1H-6127; K1H-2023 and KIH5996.

Controlling harmful plants selectively is of particular interest in crops of useful plants and ornamentals. Even though the compounds (I) already exhibit very good to sufficient selectivity in many crops, it is possible, in principle, that symptoms of phytotoxicity occur on the cultivated plants in some crops and especially also in the case of mixtures with other herbicides which are less selective. In this respect, combinations of compounds (I) according to the invention which are of particular interest are those which contain the compounds (I) or their combinations with other herbicides or pesticides and safeners. The safeners, which are employed in such an amount that they act as antidote, reduce the phytotoxic side effects of the herbicides/pesticides employed, for example in economically important crops such as cereals (wheat, barley, rye, maize, rice, sorghum and millet), sugar beet, sugar cane, oilseed rape, cotton and soybeans, preferably cereals. The following groups of compounds are examples of suitable safeners for the compounds (I) and their combinations with further pesticides:

a) compounds of the dichlorophenylpyrazoline-3-carboxylic acid type, preferably compounds such as ethyl 1-(2,4-dichlorophenyl)-5-(ethoxycarbonyl)-5-methyl-2-pyrazoline-3-carboxylate (S1-1) ("Mefenpyr-diethyl", PM, pp. 594-595) and related compounds as they are described in WO 91/07874;

b) dichlorophenylpyrazolecarboxylic acid derivatives, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4), ethyl 1-(2,4-dichlorophenyl)-5-phenylpyrazole-3-carboxylate (S 1-5) and related compounds as they are described in EP-A-333 131 and EP-A-269 806;

c) compounds of the triazolecarboxylic acids type, preferably compounds such as fenchlorazol (and its ethyl ester), i.e. ethyl 1-(2,4-dichlorophenyl)-5-trichloromethyl-(1H)-1,2,4-triazole-3-carboxylate (S1-6), and related compounds (see EP-A-174 562 and EP-A-346 620);

d) compounds of the 5-benzyl- or 5-phenyl-2-isoxazoline-3-carboxylic acid type or the 5,5-diphenyl-2-isoxazoline-3-carboxylic acid, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds as they are described in WO 91/08202, or ethyl 5,5-diphenyl-2-isoxazolinecarboxylate (S1-9) ("isoxadifen-ethyl") or n-propyl 5,5-diphenyl-2-isoxazolinecarboxylate (S1-10) or ethyl 5-(4-fluorophenyl)-5-phenyl-2-isoxazoline-3-carboxylate (S1-11), as they are described in German Patent Application (WO-A-95/07897);

e) compounds of the 8-quinolinoxyacetic acid type (S2), preferably 1-methylhex-1-yl (5-chloro-8-quinolinoxy)acetate (common name "cloquintocet-mexyl") (S2-1) (see PM, pp. 195-196)
1,3-dimethylbut-1-yl(5-chloro-8-quinolinoxy)acetate (S2-2),
4-allyloxybutyl(5-chloro-8-quinolinoxy)acetate (S2-3),
1-allyloxyprop-2-yl(5-chloro-8-quinolinoxy)acetate (S2-4),
ethyl(5-chloro-8-quinolinoxy)acetate (S2-5),
methyl(5-chloro-8-quinolinoxy)acetate (S2-6),
allyl(5-chloro-8-quinolinoxy)acetate (S2-7),
2-(2-propylideneiminooxy)-1-ethyl(5-chloro-8-quinolinoxy)acetate (S2-8),
2-oxoprop-1-yl(5-chloro-8-quinolinoxy)acetate (S2-9),
and related compounds as are described in EP-A-86 750, EP-A-94 349 and EP-A-191 736 or EP-A-0 492 366;

f) compounds of the (5-chloro-8-quinolinoxy)malonic acid type, preferably compounds such as diethyl(5-chloro-8-quinolinoxy)malonate, diallyl (5-chloro-8-quinolinoxy) malonate, methylethyl(5-chloro-8-quinolinoxy)malonate and related compounds as are described in EP-A-0 582 198;

g) active substances of the phenoxyacetic or phenoxypropionic acid derivatives type or of the aromatic carboxylic acids type, such as, for example, 2,4-dichlorophenoxyacetic acids (and its esters) (2,4-D), 4-chloro-2-methylphenoxypropionic esters (mecoprop), MCPA or 3,6-dichloro-2-methoxybenzoic acid (and its esters) (dicamba);

h) active substances of the pyrimidines type which are employed in rice as soil-acting safeners, such as, for example,
"fenclorim" (PM, pp. 386-387) (=4,6-dichloro-2-phenylpyrimidine), which is also known as safener for pretilachlor in seeded rice;

i) active substances of the dichloroacetamides type, which are frequently employed as pre-emergence safeners (soil-acting safeners), such as, for example,
"dichlormid" (PM, pp. 270-271) (=N,N-diallyl-2,2-dichloroacetamide),
"R-29148" (=3-dichloroacetyl-2,2,5-trimethyl-1,3-oxazolidine, by Stauffer),
"benoxacor" (PM, pp. 74-75) (=4-dichloroacetyl-3,4-dihydro-3-methyl-2H-1,4-benzoxazine),
"PPG-1292" (=N-allyl-N-[(1,3-dioxolan-2-yl)methyl] dichloroacetamide by PPG Industries),
"DK-24" (=N-allyl-N-[(allylaminocarbonyl)methyl] dichloroacetamide by Sagro-Chem),
"AD-67" or "MON 4660" (=3-dichloroacetyl-1-oxa-3-azaspiro[4,5]decane by Nitrokemia and Monsanto, respectively),
"diclonon" or "BAS145138" or "LAB145138" (=3-dichloroacetyl-2,5,5-trimethyl-1,3-diazabicyclo[4.3.0] nonane by BASF) and
"furilazol" or "MON 13900" (see PM, 482483) (=(RS)-3-dichloroacetyl-5-(2-furyl)-2,2-dimethyloxazolidine);

j) active substances of the dichloroacetone derivatives type, such as, for example, "MG 191" (CAS Reg. No. 96420-72-3) (=2-dichloromethyl-2-methyl-1,3-dioxolane by Nitrokemia), which is known as safener for maize;

k) active substances of the oxyimino compounds type, which are known as seed treatment products, such as, for example,
"oxabetrinil" (PM, pp. 689) (=(Z)-1,3-dioxolan-2-ylmethoxyimino(phenyl)-acetonitrile), which is known as seed-treatment safener for sorghum and millet against metolachlor damage,
"fluxofenim" (PM, pp. 467468) (=1-(4-chlorophenyl)-2,2,2-trifluoro-1-ethanone O-(1,3-dioxolan-2-ylmethyl) oxime, which is known as seed-dressing safener for sorghum and millet against metolachlor damage, and
"cyometrinil" or "-CGA-43089" (PM, p. 1170) (=(Z)-cyanomethoxy-imino(phenyl)acetonitrile), which is known as seed-treatment safener for sorghum and millet against metolachlor damage;

l) active substances of the thiazolecarboxylic ester type, which are known as seed treatment products, such as, for example,
"flurazole" (PM, pp. 450-451) (=benzyl 2-chloro-4-trifluoromethyl-1,3-thiazole-5-carboxylate), which is known as seed-treatment safener for sorghum and millet against alachlor and metolachlor damage;

m) active substances of the naphthalenedicarboxylic acid derivatives type, which are known as seed treatment products, such as, for example,
"naphthalic anhydride" (PM, p. 1009-1010) (=1,8-naphthalenedicarboxylic anhydride), which is known as seed-treatment safener for maize against thiocarbamate herbicide damage;

n) active substances of the chromanacetic acid derivatives type, such as, for example,
  "CL 304415" (CAS Reg. No. 31541-57-8) (=2-(4-carboxychroman-4-yl)acetic acid by American Cyanamid), which is known as safener for maize against damage by imidazolinones;
o) active substances which, in addition to a herbicidal action against harmful plants, also exhibit a safener action in connection with crop plants such as rice, such as, for example,
  "dimepiperate" or "MY-93" (PM, pp. 302-303) (=S-1-methyl-1-phenylethyl piperidine-1-carbothioate), which is known as safener for rice against damage by the herbicide molinate,
  "daimuron" or "SK 23" (PM, p. 247) (=1-(1-methyl-1-phenylethyl)-3-p-tolylurea), which is known as safener for rice against damage by the herbicide imazosulfuron,
  "cumyluron"="JC-940" (=3-(2-chlorophenylmethyl)-1-(1-methyl-1-phenylethyl)urea, see JP-A-60087254), which is known as safener for rice against damage by several herbicides,
  "methoxyphenone" or "NK 049" (=3,3'-dimethyl-4-methoxybenzophenone), which is known as safener for rice against damage by several herbicides,
  "CSB" (=1-bromo-4-(chloromethylsulfonyl)benzene) (CAS Reg. No. 54091-064, by Kumiai), which is known as safener in rice against damage by several herbicides;
p) N-acylsulfonamides of the formula (S3) and their salts

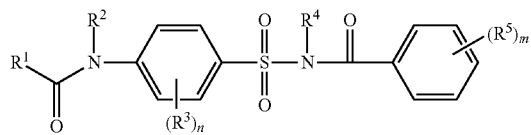

(S3)

as are described in WO-A-97/45016;
q) acylsulfamoylbenzamides of the formula (S4), if appropriate also in salt form,

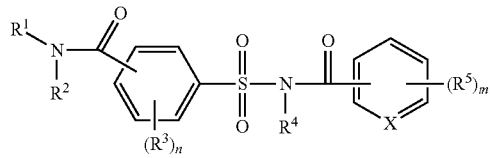

(S4)

as are described in International Application No. PCT/EP98/06097; and
r) compounds of the formula (S5),

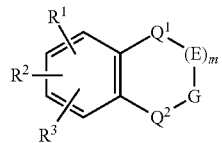

(S5)

as are described in WO-A 98/13361,
including the stereoisomers and the salts conventionally used in agriculture.

Amongst the safeners mentioned, those which are of particular interest are (S1-1) and (S1-9) and (S2-1), in particular (S1-1) and (S1-9).

Some of the safeners are already known as herbicides and therefore simultaneously also display a protective action in connection with the crop plants in addition to the herbicidal action in connection with harmful plants.

The weight ratio of herbicide (mixture) to safener generally depends on the application rate of herbicide and the efficacy of the safener in question; it can vary within wide limits, for example in the range of from 200:1 to 1:200, preferably from 100:1 to 1:100, in particular 20:1 to 1:20. The safeners can be formulated with further herbicides/pesticides, analogously to the compounds (I) or their mixtures, and provided and used as readymix or tank mix together with the herbicides.

For use, the herbicide or herbicide safener formulations, which are present in a customary commercial form, are, if appropriate, diluted in the customary fashion, for example using water in the case of wettable powders, emulsifiable concentrates, dispersions and water-dispersible granules. Preparations in the form of dusts, soil granules, granules for spreading, and sprayable solutions, are usually not diluted further with other inert materials prior to use.

The application rate required of the compounds of the formula (I) varies with, inter alia, the external conditions such as temperature, humidity and the type of the herbicide used. It can vary within wide limits, for example between 0.001 and 10.0 kg/ha or more of active substance, but it is preferably between 0.002 and 3 kg/ha, in particular 0.005 and 1 kg/ha.

B. FORMULATION EXAMPLES a) A dust is obtained by mixing 10 parts by weight of a compound of formula (I) and 90 parts by weight of talc as inert material and grinding the mixture in a hammer mill.

b) A wettable powder which is readily dispersible in water is obtained by mixing 25 parts by weight of a compound of formula (I), 64 parts by weight of kaolin-containing quartz as inert material, 10 parts by weight of potassium lignosulfonate and 1 part by weight of sodium oleoylmethyltaurinate as wetter and dispersant and grinding the mixture in a pinned-disk mill.

c) A dispersion concentrate which is readily dispersible in water is obtained by mixing 20 parts by weight of a compound of formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.) and grinding the mixture in a ball mill to a fineness of below 5 microns.

d) An emulsifiable concentrate is obtained from 15 parts by weight of a compound of formula (I), 75 parts by weight of cyclohexanone as solvent and 10 parts by weight of oxethylated nonylphenol as emulsifier.

e) Water-dispersible granules are obtained by mixing
75 parts by weight of a compound of formula (I),
10 parts by weight of calcium ligno-sulfonate,
5 parts by weight of sodium laurylsulfate,
3 parts by weight of polyvinyl alcohol and
7 parts by weight of kaolin,
grinding the mixture in a pinned disk mill and granulating the powder in a fluidized bed by spraying on water as granulation liquid.

f) Alternatively, water-dispersible granules are obtained by homogenizing and precomminuting, on a colloid mill,
25 parts by weight of a compound of formula (I),
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water,
subsequently grinding the mixture on a bead mill and atomizing and drying the resulting suspension in a spray tower by means of a single-substance nozzle.

C. BIOLOGICAL EXAMPLES

Biological Example 1

Pre-Emergence Effect on Weeds

Seeds or rhizome pieces of monocotyledonous and dicotyledonous weed plants were placed in sandy loam in plastic pots and covered with soil. The compounds according to the invention, which were formulated in the form of wettable powders or emulsion concentrates, were then applied to the surface of the soil cover as aqueous suspension or emulsion at various dosages with an application rate of 600 to 800 l of water per ha (converted).

After the treatment, the pots were placed into a greenhouse and kept under good growth conditions for the weeds. The plant or emergence damage was scored visually after the test plants have emerged after an experimental time of 3 to 4 weeks by comparison with untreated controls.

Compound numbers 1.1, 1.2, 1.3, 1.7, 1.11, 1.12, 1.15, 1.20, 1.21, 1.24, 1.28, 1.31, 1.66, 1.67, 1.68, 1.69, 2.1, 2.2, 2.4, 2.11, 2.25, 2.28, 3.1, 3.2, 3.7, 3.11, 3.15, 3.20, 3.24, 4.1, 4.2, 5.1, 5.2, 6.1, 6.2, 7.1, 7.2, 7.3, 7.4, 7.11, 7.24, 7.47, 7.48, 7.57, 7.70, 7.72, 7.74, 7.75, 7.78, 7.203, 7.228, 7.229, 7.238, 7.239, 7.240, 7.241, 7.242, 7.243, 7.244, 7.245, 8.1, 8.2, 8.3, 8.7, 8.11, 8.12, 8.15, 8.21, 8.24, 8.25, 8.26, 8.34, 8.35, 8.38, 8.44, 8.48, 8.49, 8.58, 8.61, 8.67, 8.68, 8.71, 8.75, 8.79, 8.90, 8.100, 8.113, 8.117, 8.148, 8.152, 8.160, 8.170, 8.183, 8.187, 8.195, 8.196, 8.197, 8.201, 8.205, 8.206, 8.209, 8.215, 8.219, 8.231, 8.233, 8.234, 8.237, 8.238, 8.239, 8.240, 8.241, 8.242, 8.243, 8.244, 8.245, 8.246, 8.247, 8.248, 8.249, 8.250, 8.251, 8.252, 8.253, 8.254, 8.255, 8.256, 8.257, 9.36, 9.37, 9.66, 10.1, 10.2, 10.37, 10.38, 10.47, 10.57, 10.66, 10.67 and 10.68 according to the invention show a very good pre-emergence control of harmful plants such as *Stellaria media*, *Lolium multiforum*, *Amaranthus retroflexus*, *Sinapis alba*, *Avena sativa* and *Setaria viridis* when applied at an application rate of 1 kg or less of active ingredient per hectare.

Biological Example 2

Post-Emergence Effect on Weeds

Seeds or rhizome pieces of monocotyledonous and dicotyledonous weeds were placed in sandy loam in plastic pots, covered with soil and grown in the greenhouse under good growth conditions. Three weeks after sowing, the test plants were treated in the three-leaf stage. Various dosages of the compounds according to the invention, which were formulated as wettable powders or emulsion concentrates, were sprayed to the green plant parts at an application rate of 600 to 800 l of water per ha (converted). After the test plants have been left to stand in the greenhouse for approx. 3 to 4 weeks under optimal growth conditions, the effect of the preparations was scored visually by comparison with untreated controls. Compound numbers 1.1, 1.2, 1.3, 1.7, 1.11, 1.12, 1.15, 1.20, 1.21, 1.24, 1.28, 1.31, 1.66, 1.67, 1.68, 1.69, 2.1, 2.2, 2.4, 2.11, 2.25, 2.28, 3.1, 3.2, 3.7, 3.11, 3.15, 3.20, 3.24, 4.1, 4.2, 5.1, 5.2, 6.1, 6.2, 7.1, 7.2, 7.3, 7.4, 7.11, 7.24, 7.47, 7.48, 7.57, 7.70, 7.72, 7.74, 7.75, 7.78, 7.203, 7.228, 7.229, 7.238, 7.239, 7.240, 7.241, 7.242, 7.243, 7.244, 7.245, 8.1, 8.2, 8.3, 8.7, 8.11, 8.12, 8.15, 8.21, 8.24, 8.25, 8.26, 8.34, 8.35, 8.38, 8.44, 8.48, 8.49, 8.58, 8.61, 8.67, 8.68, 8.71, 8.75, 8.79, 8.90, 8.100, 8.113, 8.117, 8.148, 8.152, 8.160, 8.170, 8.183, 8.187, 8.195, 8.196, 8.197, 8.201, 8.205, 8.206, 8.209, 8.215, 8.219, 8.231, 8.233, 8.234, 8.237, 8.238, 8.239, 8.240, 8.241, 8.242, 8.243, 8.244, 8.245, 8.246, 8.247, 8.248, 8.249, 8.250, 8.251, 8.252, 8.253, 8.254, 8.255, 8.256, 8.257, 9.36, 9.37, 9.66, 10.1, 10.2, 10.37, 10.38, 10.47, 10.57, 10.66, 10.67 and 10.68 according to the invention show a very good herbicidal post-emergence activity against against harmful plants such as *Sinapis alba*, *Echinochloa crus-galli*, *Lolium multiflorum*, *Stellaria media*, *Cyperus iria*, *Amaranthus retroflexus*, *Setaria viridis*, *Avena sativa*, *Lamium purpureum*, *Matricaria inodora*, *Papaver rhoeas*, *Veronica persica*, *Viola trocolor*, *Kochia* spp and *Chenopodium album* when applied at an application rate of 2 kg or less of active ingredient per hectare.

Biological Example 3

Weed Control in Plantation Crops

In further field trials plantation crops were grown under conditions of natural weed infestation and sprayed with various dosages of the substances of formula (I) according to the invention. At various time intervals after the application it is found by means of visual assessment that the compounds according to the invention leave the plantation crops such as, for example, oil palm, coconut palm, India-rubber tree, citrus, pineapples, cotton, coffee, cocoa and vines unharmed, even at high rates of active substance. The compounds of formula (I) show an improved degree of selectivity compared to the prior art, and are therefore suitable for controlling undesired vegetation in plantation crops. Additionally the weeds are very well controlled especially when applied pre-emergence of the weeds.

The invention claimed is:
1. An optically active compound of formula (I),

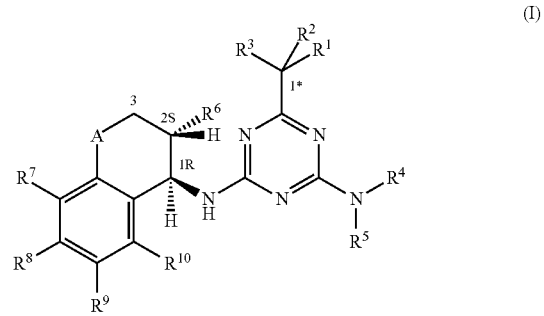

in which:
$R^1$ is H, halogen, $(C_1-C_6)$alkyl, $(C_1-C_6)$haloalkyl, $[(C_1-C_4)$alkoxy]$(C_1-C_6)$alkyl, $(C_3-C_6)$cycloalkyl which is unsubstituted or substituted by one or more radicals selected from the group consisting of halogen, $(C_1-C_4)$alkyl and $(C_1-C_4)$haloalkyl, or is $(C_2-C_6)$alkenyl, $(C_2$-

77

$C_6$)alkynyl, $(C_2-C_6)$haloalkenyl, $(C_4-C_6)$cycloalkenyl, $(C_4-C_6)$halocycloalkenyl, $(C_1-C_6)$alkoxy or $(C_1-C_6)$haloalkoxy;

$R^2$ is H, halogen, $(C_1-C_6)$alkyl or $(C_1-C_4)$alkoxy; or $R^1$ and $R^2$ can together with the attached carbon atom form a $(C_3-C_6)$cycloalkyl or $(C_4-C_6)$cycloalkenyl ring;

$R^3$ is H, $(C_1-C_6)$alkyl, $(C_1-C_4)$alkoxy or halogen;

$R^4$ and $R^5$ are each independently H, $(C_1-C_4)$alkyl, $(C_1-C_4)$haloalkyl, $(C_3-C_4)$alkenyl, $(C_3-C_4)$haloalkenyl, $(C_3-C_4)$alkynyl, $(C_3-C_4)$haloalkynyl or an acyl radical;

$R^6$ is $(C_1-C_6)$alkyl;

$R^7$, $R^8$, $R^9$ and $R^{10}$ are each independently H, $(C_1-C_4)$alkyl, $(C_1-C_3)$haloalkyl, halogen, $(C_1-C_3)$alkoxy, $(C_1-C_3)$haloalkoxy or CN;

A is $CH_2$, O or a direct bond; and the stereochemical configuration at the marked 1R position has a stereochemical purity of from 60 to 100% (R), the stereochemical configuration at the marked 2S position has a stereochemical purity of from 60 to 100% (S), provided that $R^1$, $R^2$ and $R^3$ are structurally different or provided that at least two of $R^1$, $R^2$ and $R^3$ are structurally identical, or an agriculturally acceptable salt thereof.

2. A compound or an agriculturally acceptable salt thereof as claimed in claim 1, wherein:

$R^1$ is H, halogen, $(C_1-C_4)$alkyl, $(C_1-C_4)$haloalkyl, $[(C_1-C_4)$alkoxy$](C_1-C_4)$alkyl, $(C_3-C_6)$cycloalkyl which is unsubstituted or substituted by one or two $(C_1-C_4)$alkyl groups, or is $(C_3-C_4)$halocycloalkyl, $(C_2-C_4)$alkenyl, $(C_2-C_4)$haloalkenyl, $(C_2-C_4)$alkynyl, $(C_1-C_4)$alkoxy or $(C_1-C_4)$haloalkoxy;

$R^2$ is H or $(C_1-C_4)$alkyl; or $R^1$ and $R^2$ together with the attached carbon atom form a $(C_3-C_6)$cycloalkyl ring;

$R^3$ is H, $(C_1-C_4)$alkyl, $(C_1-C_2)$alkoxy or halogen;

$R^4$ is H, $(C_1-C_4)$alkyl, $(C_1-C_4)$haloalkyl, $(C_3-C_4)$alkenyl, $(C_3-C_4)$alkynyl or an acyl radical having 1 to 12 carbon atoms;

$R^5$ is H, $(C_1-C_4)$alkyl or $(C_1-C_4)$haloalkyl;

$R^6$ is $(C_1-C_3)$alkyl;

$R^7$, $R^8$, $R^9$ and $R^{10}$ are each independently H, $(C_1-C_3)$alkyl, halogen or $(C_1-C_3)$alkoxy; and A is $CH_2$, O or a direct bond.

3. A compound or an agriculturally acceptable salt thereof as claimed in claim 1, wherein:

$R^1$ is H or $(C_1-C_3)$alkyl;

$R^2$ is H or $(C_1-C_3)$alkyl; or $R^1$ and $R^2$ together with the attached carbon atom form a $(C_3-C_4)$cycloalkyl ring;

$R^3$ is H, $(C_1-C_2)$alkyl, methoxy, Cl or F;

$R^4$ is H, $(C_1-C_3)$alkyl, $(C_1-C_3)$haloalkyl, allyl, propargyl, CHO, —CO$(C_1-C_3)$alkyl or —CO$(C_1-C_3)$haloalkyl;

$R^5$ is H or $(C_1-C_2)$alkyl;

$R^6$ is $(C_1-C_3)$alkyl;

$R^7$, $R^8$, $R^9$ and $R^{10}$ are each independently H, methyl, F and Cl; and A is $CH_2$, O or a direct bond.

4. A process for the preparation of a compound of the formula (I) or an agriculturally acceptable salt thereof as defined in claim 1, which process comprises:

78 a) reacting a compound of formula (II):

(II)

$$R^3 \underset{Z}{\overset{R^2}{\underset{|}{-}}} R^1$$

wherein $R^1$, $R^2$ and $R^3$ are as defined in formula (I), and

Z is a functional group selected from the group consisting of carboxylic ester, carboxylic orthoester, carboxylic acid chloride, carboxamide, cyano, carboxylic anhydride or trichloromethyl, with a biguanidine compound of formula (III) or an acid addition salt thereof:

(III)

wherein $R^4$, $R^5$, $R^6$, $R^7$, $R^8$, $R^9$, $R^{10}$ and A and the configuration at the marked 1R and 2S positions are as defined in formula (I); or b) reacting a compound of formula (IV):

(IV)

wherein $R^1$, $R^2$, $R^3$, $R^4$ and $R^5$ and the configuration at the marked 1* position are as defined in formula (I), and $L^1$ is a leaving group, with an amine of formula (V) or an acid addition salt thereof:

(V)

wherein $R^6$, $R^7$, $R^8$, $R^9$, $R^{10}$ and A and the configuration at the marked 1R and 2S positions are as defined in formula (I); or c) where one of $R^4$ or $R^5$ in formula (I) is $(C_1-C_4)$alkyl, $(C_1-C_4)$haloalkyl, $(C_3-C_4)$alkenyl, $(C_3-C_4)$haloalkenyl, $(C_3-C_4)$alkynyl or $(C_3-C_4)$haloalkynyl, reacting the corresponding compound of formula (I) wherein said $R^4$ or $R^5$ respectively is H, and the other radicals and the configurations are as defined in formula (I), with an alkylating agent of formula (VI) or (VII) respectively: $R^4$-$L^2$ (VI) $R^5$-$L^2$ (VI) wherein $L^2$ is a leaving group; or d) where one of $R^4$ or $R^5$ is an acyl radical in formula (I), reacting the corresponding compound of formula (I) wherein said $R^4$ or $R^5$ respectively is H, and the other radicals and the configurations are as defined in formula (I), with an acylating agent of formula (VIII) or (IX) respectively: $R^4$-$L^3$ (VIII) $R^5$-$L^3$ (IX) wherein $R^4$ and $R^5$ are each an acyl radical as defined in formula (I) and $L^3$ is a leaving group; or e) resolving a compound of formula (I) by using in the above-described processes one or more intermediates (II), (III), (IV) or (V) whose configuration differs from the configuration as defined in the compound of formula (I) to be prepared, and resolving the mixture obtained according to known methods of resolution.

5. A herbicidal or plant growth regulating composition, which comprises one or more compounds of the formula (I) or their agriculturally acceptable salts as claimed in claim 1 and formulation auxiliaries applicable in crop protection.

6. A method of controlling harmful plants or for regulating the growth of plants, which comprises applying an active amount of one or more compounds of the formula (I) or their agriculturally acceptable salts as claimed in claim 1 to the plants, plant seeds or the area under cultivation.

7. A compound or a salt thereof as claimed in claim 1, characterized in that it is a compound of the formula (Ib) or a salt thereof,

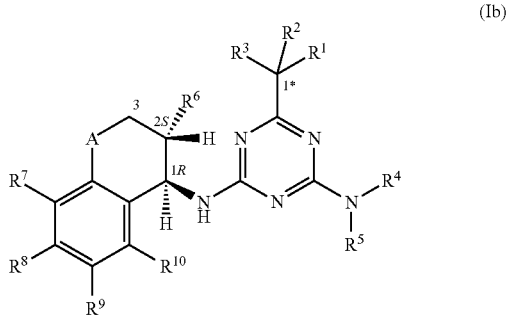

(Ib)

wherein:
$R^1$ is H, $(C_1-C_6)$alkyl or $(C_1-C_6)$alkoxy;
$R^2$ is H or $(C_1-C_4)$alkyl; or
$R^1$ and $R^2$ can together with the attached carbon atom form a $(C_3-C_6)$cycloalkyl ring;
$R^3$ is H, $(C_1-C_4)$alkyl or halogen;
$R^4$ and $R^5$ are each H;
$R^6$ is $(C_1-C_6)$alkyl;
$R^7$, $R^8$, $R^9$ and $R^{10}$ are each independently H, $(C_1-C_6)$alkyl or halogen; and
A is $CH_2$, O or a direct bond,
provided that the stereochemical configurations at positions 1R and 2S are defined as in formula (I) and provided that at least two of $R^1$, $R^2$ and $R^3$ are structurally identical.

8. A compound or a salt thereof as claimed in claim 7, characterized in that
$R^1$ is H, methyl or ethyl;
$R^2$ is H;
$R^3$ is H, F, Cl, methyl or ethyl;
$R^4$ and $R^5$ are each H;
$R^6$ is $(C_1-C_4)$alkyl;
$R^7$, $R^8$, $R^9$ and $R^{10}$ are each independently selected from the group consisting of H, methyl, Br, Cl or F; and
A is $CH_2$, O or a direct bond,
provided that at least two of $R^1$, $R^2$ and $R^3$ are structurally identical.

9. A compound or a salt thereof as claimed in claim 1, characterized in that it is a compound of the formula (Ic) or a salt thereof,

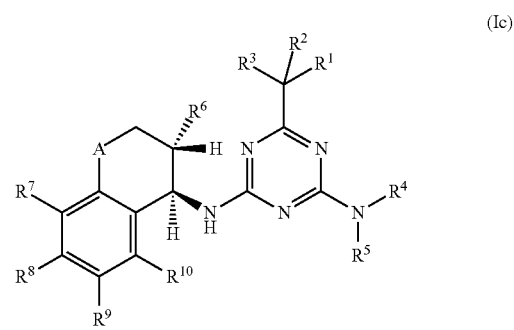

(Ic)

wherein $R^1$ to $R^{10}$ and A and the stereochemical configurations at positions 1 and 2 are defined as in formula (I) and provided that $R^1$, $R^2$ and $R^3$, are structurally different.

10. A compound or a salt thereof as claimed in claim 9, characterized in that it is a compound of the formula (If) or a salt thereof,

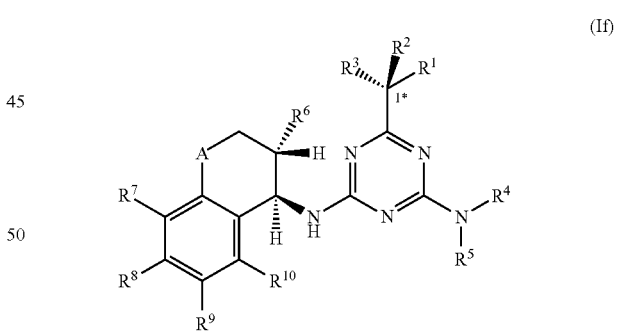

(If)

wherein:
$R^1$ is $(C_1-C_6)$alkyl, $(C_1-C_6)$haloalkyl or $(C_3-C_6)$cycloalkyl;
$R^2$ is H;
$R^3$ is $(C_1-C_4)$alkyl or halogen;
$R^6$ is $(C_1-C_6)$alkyl; and
$R^4$, $R^5$, $R^7$ to $R^{10}$ and A and the stereochemical configurations at positions 1 and 2 are defined as in formula (Ic),
provided that $R^1$, $R^2$ and $R^3$ are structurally different and the stereochemical configuration at the marked 1* position is having a stereochemical purity of from 60 to 100%.

11. A compound or a salt thereof as claimed in claim 10, characterized in that $R^1$ is methyl or ethyl;
$R^2$ is H;
$R^3$ is methyl, ethyl, F or Cl;
$R^4$ and $R^5$ are each H;
$R^6$ is methyl or ethyl; and
$R^7$, $R^8$, $R^9$ and $R^{10}$ are each independently H, methyl, Br, Cl or F,
provided that $R^1$, $R^2$ and $R^3$ are structurally different.

12. A compound or a salt thereof as claimed in claim 1, characterized in that the stereochemical configuration at the marked 1R position has a stereochemical purity of from 80 to 100% (R), and the stereochemical configuration at the marked 2S position has a stereochemical purity of from 80 to 100% (S).

13. A compound or a salt thereof as claimed in claim 11, characterized in that the stereochemical configuration at the marked 1R position has a stereochemical purity of from 80 to 100% (R), and the stereochemical configuration at the marked 2S position has a stereochemical purity of from 80 to 100% (S).

* * * * *